United States Patent
Nel et al.

(10) Patent No.: US 11,208,330 B2
(45) Date of Patent: Dec. 28, 2021

(54) IDENTIFICATION AND OPTIMIZATION OF CARBON RADICALS ON HYDRATED GRAPHENE OXIDE FOR UBIQUITOUS ANTIBACTERIAL COATINGS

(71) Applicants: The Regents of the University of California, Oakland, CA (US); Northwestern University, Evanston, IL (US)

(72) Inventors: Andre E. Nel, Sherman Oaks, CA (US); Tian Xia, Los Angeles, CA (US); Ruibin Li, Los Angeles, CA (US); Mark C. Hersam, Wilmette, IL (US); Nikhita D. Mansukhani, Allston, MA (US); Linda Guiney, Chicago, IL (US)

(73) Assignees: The Regents of the University of California, Oakland, CA (US); Northwestern University, Evanston, IL (US)

( * ) Notice: Subject to any disclaimer, the term of this patent is extended or adjusted under 35 U.S.C. 154(b) by 45 days.

(21) Appl. No.: 16/348,862

(22) PCT Filed: Nov. 15, 2017

(86) PCT No.: PCT/US2017/061863
§ 371 (c)(1),
(2) Date: May 9, 2019

(87) PCT Pub. No.: WO2018/093943
PCT Pub. Date: May 24, 2018

(65) Prior Publication Data
US 2020/0270134 A1 Aug. 27, 2020

Related U.S. Application Data

(60) Provisional application No. 62/423,181, filed on Nov. 16, 2016.

(51) Int. Cl.
*C01B 32/198* (2017.01)
*A01N 43/90* (2006.01)
(Continued)

(52) U.S. Cl.
CPC ............ *C01B 32/198* (2017.08); *A01N 43/90* (2013.01); *A01N 59/00* (2013.01); *A61L 27/08* (2013.01)

(58) Field of Classification Search
None
See application file for complete search history.

(56) References Cited

U.S. PATENT DOCUMENTS

| 8,865,107 B2 | 10/2014 | Hersan et al. |
| 2006/0134096 A1 | 6/2006 | Petrik |

(Continued)

OTHER PUBLICATIONS

Tao Wu, Lei Zhang, Jianping Gao, Yu Liu, Chunjuan Gao and Jing Yan. "Fabrication of graphene oxide decorated with Au—Ag alloy nanoparticles and its superior catalytic performance for the reduction of 4-nitrophenol." Journal of Materials Chemistry A, vol. 1, 2013, pp. 7384-7390. (Year: 2013).*

(Continued)

*Primary Examiner* — Isaac Shomer
(74) *Attorney, Agent, or Firm* — Tom Hunter; Weaver Austin Villeneuve & Sampson LLP

(57) ABSTRACT

In various embodiments functionalized graphene oxide(s) are provided that demonstrate improved antimicrobial activity, where the graphene oxide(s) are functionalized to increase carbon radical (.C) density.

19 Claims, 49 Drawing Sheets

(51) Int. Cl.
A01N 59/00 (2006.01)
A61L 27/08 (2006.01)

(56) References Cited

U.S. PATENT DOCUMENTS

| | | | |
|---|---|---|---|
| 2008/0050412 A1* | 2/2008 | Jones | A61L 27/54 |
| | | | 424/423 |
| 2008/0226728 A1* | 9/2008 | Domb | A01N 37/12 |
| | | | 424/489 |
| 2012/0164433 A1 | 6/2012 | Advincula | |
| 2013/0065034 A1 | 3/2013 | Muramatsu | |
| 2013/0266628 A1 | 10/2013 | Thalappil et al. | |
| 2013/0313523 A1 | 11/2013 | Yun et al. | |
| 2013/0330833 A1 | 12/2013 | Ruiz et al. | |
| 2014/0144541 A1 | 5/2014 | Moreira et al. | |
| 2014/0193575 A1 | 7/2014 | Hosmane et al. | |
| 2014/0199777 A2 | 7/2014 | Ruiz et al. | |
| 2014/0316466 A1* | 10/2014 | Dinville | A61B 17/7071 |
| | | | 606/249 |
| 2015/0004055 A1 | 1/2015 | Ling et al. | |
| 2015/0065601 A1* | 3/2015 | Alsharaeh | C08K 3/042 |
| | | | 522/81 |
| 2015/0099848 A1* | 4/2015 | Fish | B29C 70/34 |
| | | | 524/588 |
| 2015/0110998 A1 | 4/2015 | Borrelli et al. | |
| 2015/0125533 A1 | 5/2015 | Sallam et al. | |
| 2015/0137077 A1 | 5/2015 | Yun et al. | |
| 2015/0198886 A1 | 7/2015 | Lai et al. | |
| 2015/0232343 A1 | 8/2015 | Liu et al. | |
| 2015/0258506 A1 | 9/2015 | Mi et al. | |
| 2016/0022827 A1 | 1/2016 | Chan et al. | |
| 2016/0176714 A1 | 6/2016 | Do et al. | |
| 2016/0200581 A1 | 7/2016 | Lee et al. | |
| 2016/0270403 A1 | 9/2016 | Ling et al. | |
| 2016/0272583 A1 | 9/2016 | Lee et al. | |

OTHER PUBLICATIONS

Supporting Information for B. Rezania, Nikolai Severin, Alexandr V. Talyzin, and Jürgen P. Rabe. "Hydration of Bilayered Graphene Oxide." Nano Letters, vol. 14, 2014, 4 printed pages of supporting information. (Year: 2014).*

B. Rezania, Nikolai Severin, Alexandr V. Talyzin, and Jurgen P. Rabe. "Hydration of Bilayered Graphene Oxide." Nano Letters, vol. 14, 2014, pp. 3993-3998. (Year: 2014).*

Elmar R. Altwicker. "The Chemistry of Stable Phenoxy Radicals." Chemical Reviews, vol. 67, No. 5, Sep. 1967, pp. 475-531. (Year: 1967).*

Shaobin Liu, Tingying Helen Zeng, Mario Hofmann, Ehdi Burcombe, Jun Wei, Rongrong Jiang, Jing Kong and Yuan Chen." Antibacterial Activity of Graphite, Graphite Oxide, Graphene Oxide, and Reduced Graphene Oxide: Membrane and Oxidative Stress ." ACS Nano, vol. 5 No. 9, pp. 6971-6980. (Year: 2011).*

Panagiota Stathi, Dimitrios Gournis, Yiannis Deligiannakis, and Petra Rudolf. "Stabilization of Phenolic Radicals on Graphene Oxide: An XPS and EPR Study." Langmuir, vol. 31, 2015, pp. 10508-10516. (Year: 2015).*

Andreia F. de Faria, François Perreault, Evyatar Shaulsky, Laura H. Arias Chavez, and Menachem Elimelech. "Antimicrobial Electrospun Biopolymer Nanofiber Mats Functionalized with Graphene Oxide—Silver Nanocomposites." ACS Applied Materials and Interfaces, vol. 7, pp. 12751-12759. (Year: 2015).*

Francois Perreault, Andreia Fonseca de Faria, Siamak Nejati, and Menachem Elimelech. "Antimicrobial Properties of Graphene Oxide Nanosheets: Why Size Matters." vol. 9 No. 7, 2015, pp. 7226-7236. (Year: 2015).*

Liang Yang, Ruilong Zhang, Bianhua Liu, Jianping Wang, Suhua Wang, Ming-Yong Han, and Zhongping Zhang. "p-Conjugated Carbon Radicals at Graphene Oxide to Initiate Ultrastrong Chemiluminescence." Andewandte Chemie International Edition, vol. 53, 2014, pp. 10109-10113. (Year: 2014).*

PCT International Search Report and Written Opinion dated Feb. 1, 2018 issued in PCT/US2017/061863.

PCT International Preliminary Report on Patentability dated May 21, 2019 issued in PCT/US2017/061863.

EP Extended European Search Report dated Apr. 15, 2020 issued in EP17871124.8.

Akhavan et al. (2010) "Toxicity of Graphene and Graphene oxide Nanowalls Against Bacteria" *ACS Nano* 4(10): 5731-5736.

Ji et al. (2016) "Antibacterial applications of graphene-based nanomaterials: Recent achievements and challenges" *Advanced Drug Delivery Reviews* 105: 176-189.

Li et al. (2016) "Identification and Optimization of Carbon Radicals on Hydrated Graphene Oxide for Ubiquitous Antibacterial Coatings" *ACS Nano* 10(12): 10966-10980 DOI: 10.1021/acsnano.6b05692.

Liu et al. (2011) "Antibacterial Activity of Graphite, Graphite Oxide, Graphene Oxide, and Reduced Graphene Oxide: Membrane and Oxidative Stress," *ACS Nano* 5(9): 6971-6980.

Ma et al. (2015) "Copper-Assisted Direct Growth of Vertical Graphene Nanosheets on Glass Substrates by Low-Temperature Plasma-Enhanced Chemical Vapour Deposition Process" *Nanoscale Research Letters* 10: 308 (8 pages).

Tu et al. (2013) "Destructive extraction of phospholipids from *Escherichia coli* membranes by graphene nanosheets" *Nature Nanotechnology* 8(8): 594-601.

Yang et al. (2014) "π-Conjugated Carbon Radicals at Graphene Oxide to Initiate Ultrastrong Chemiluminescence" *Angew. Chem. Int.* 53(38): 10109-10113.

Jahnert et al. (2014) "Application of phenolic radicals for antioxidants, as active materials in batteries, magnetic materials and ligands for metal-complexes." *Journal of Materials Chemistry A*, 2: 15234-15251.

Lu et al. (2017) "Enhanced antibacterial activity through the controlled alignment of graphene oxide nanosheets" *PNAS*, E9793-E9801; Published online Oct. 26, 2017 www.pnas.org/cgi/doi/10.1073/pnas.1710996114.

* cited by examiner

SEM of *E. coli* (AR) on hGO coated catheter

Covalent hGO-2 coating on silicon wafer

AFM image

Raman spectra

IDENTIFICATION AND OPTIMIZATION OF CARBON RADICALS ON HYDRATED GRAPHENE OXIDE FOR UBIQUITOUS ANTIBACTERIAL COATINGS

CROSS-REFERENCE TO RELATED APPLICATIONS

This application is a U.S. 371 National Phase of PCT/US2017/061863, filed Nov. 15, 2017, which claims benefit of and priority to U.S. Ser. No. 62/423,181, filed on Nov. 16, 2016, both of which are incorporated herein by reference in their entirety for all purposes.

STATEMENT OF GOVERNMENTAL SUPPORT

This invention was made with government support under Grant No. ES022698 awarded by the National Institutes of Health, and by Grant No: DBI1266377 awarded by the National Science Foundation. The Government has certain rights in this invention.

BACKGROUND

Chemically modified graphene has been widely studied for various applications, such as polymer composites, energy-related materials, and catalysis (Georgakilas et al. (2012) *Chem. Rev.* 112(11): 6156-6214; Sun et al. (2011) *J. Phys. Chem. Lett.* 2(19): 2425-2432). Of particular interest is graphene oxide (GO), an oxygenated form of graphene decorated with abundant functional groups. GO is widely used due to its wide availability, facile synthesis, and outstanding electronic, optical, and chemical properties (Chen et al. (2012) *Chem. Rev.* 112(11): 6027-6053; Compton et al. (2010) *Small*, 6(6): 711-723; Zhao (2015) *Sci. Bull.* 60(22): 1962-1963). A major use for this material is in biomedical applications for drug delivery, biosensors, and tissue engineering due to its high dispersibility, two-dimensional (2D) planar structure, large surface area and surface functionalities (Chung et al. (2013) *Accounts Chem. Res.* 46(10): 2211-2224). In addition, GO has broad-based antibacterial effects that require detailed structure-activity relationships (SARs) to be established (Chen et al. (2014) *Nanoscale*, 6(3): 1879-1889; Li et al. (2013) *Proc. Natl. Acad. Sci. USA*, 110(30): 12295-12300; Tu et al. (2013) *Nat. Nanotechnol.* 8(8): 594-601).

There are two major schools of thought on the mechanism of GO-induced bactericidal effects. One is relying on the physical interaction between the unique GO structure and bacterial membranes, including direct physical puncturing of bacteria membrane (Li et al. (2013) *Proc. Natl. Acad. Sci. USA*, 110(30): 12295-12300), or destructive extraction of lipid molecules from bacterial membrane (Tu et al. (2013) *Nat. Nanotechnol.* 8(8): 594-601). However, this hypothesis is mostly premised on computer simulation, and there is a paucity of experimental evidence regarding the details of damage to the bacterial surface. Another mechanistic explanation, with supportive experimental data, is oxidative damage to the bacterial membrane by the generation of reactive oxygen species and charge transfer (Efremova et al. (2015) *Biomed. Res. Int.* 2015: 869361; Sun et al. (2014) *ACS Nano*, 8(6): 6202-6210; Zou et al. (2016) *J. Am. Chem. Soc.* 138(7): 2064-2077). While surface functional groups are assumed to play a critical role in mediating GO oxidative damage, the complex chemistry related to this material has made it difficult to discern the exact surface functional groups that may be involved in this outcome.

As-prepared GO has different oxidation levels and surface functional groups such as the presence of epoxy (—COC—), hydroxyl (—OH), and carboxyl (—COOH) moieties at different densities and combinations (Liu et al. (2011) *ACS Nano*, 5(9): 6971-6980). In addition, isolated electrons in the carbon p orbitals are often conjugated by $\pi$ bonding, which could form carbon radicals (.C) at discrete sites on the material surface (Yang et al. (2014) *Angew. Chem.-Int. Edit.* 53(38): 10109-10113). Although attempts have been made to explore the role of oxidation level (Liu et al. (2011) *ACS Nano*, 5(9): 6971-6980; Akhavan et al. (2010) *ACS Nano*, 4(10): 5731-5736), lateral flake size (Perreault et al. (2015) *ACS Nano*, 9(7): 7226-7236) or catalytic capability (Sun et al. (2014) *ACS Nano*, 8(6): 6202-6210) on bacterial killing, results have been inconclusive and even contradictory. One reason is the interlinked complexity of the functional groups, such that a change in one surface group will also affect others, often in a non-predictable fashion.

SUMMARY

While 2-dimensional graphene oxide (GO) is used increasingly in biomedical applications, there is uncertainty on how specific physicochemical properties relate to biocompatibility in mammalian systems. Although properties such as lateral size and the colloidal properties of the nanosheets are important, the specific material properties that we address here is the oxidation state and reactive surface groups on the planar surface. In this study, we used a GO library, comprised of pristine, reduced (rGO), and hydrated GO (hGO), in which quantitative assessment of the hydroxyl, carboxyl, epoxy and carbon radical contents were used to study the impact on epithelial cells and macrophages, as well as in the murine lung. Strikingly, we observed that hGO, which exhibits the highest carbon radical density, was responsible for the generation of cell death in THP-1 and BEAS-2B cells as a consequence of lipid peroxidation of the surface membrane, membrane lysis, and cell death. In contrast, pristine GO had lesser effects while rGO showed extensive cellular uptake with minimal effects on viability. In order to see how these in vitro effects relate to adverse outcomes in the lung, mice were exposed to GOs by oropharyngeal aspiration. Animal sacrifice after 40 h demonstrated that hGO was more prone than other materials in generating acute lung inflammation, accompanied by the highest lipid peroxidation in alveolar macrophages, cytokine production (LIX, MCP-1) and LDH release in bronchoalveolar lavage fluid. Pristine GO showed less toxicity while rGO had minimal effects. In summary, we demonstrate that the surface oxidation state and carbon radical content play major roles in the induction of toxicity by GO in mammalian cells and the lung.

Accordingly, in various embodiments, functionalized graphene oxide(s) are provided that demonstrate improved antimicrobial activity, where the graphene oxide(s) are functionalized to increase carbon radical (.C) density.

Various embodiments contemplated herein may include, but need not be limited to, one or more of the following:

Embodiment 1

A graphene oxide having improved antimicrobial activity, wherein said graphene oxide is a graphene oxide functionalized to increase carbon radical (.C) density.

Embodiment 2

The graphene oxide of embodiment 1, wherein the antimicrobial activity of said graphene oxide is proportional to the carbon radical density.

Embodiment 3

The graphene oxide according to any one of embodiments 1-2, wherein said graphene oxide shows increased lipid membrane binding and/or induction of lipid peroxidation as compared to unfunctionalized graphene oxide.

Embodiment 4

The graphene oxide according to any one of embodiments 1-3, wherein said graphene oxide is hydrated.

Embodiment 5

The graphene oxide according to any one of embodiments 1-4, wherein said graphene oxide shows a carbon radical content as determined by electron paramagnetic resonance (EPR) with an absorbance peak area greater than about $15 \times 10^6$, or about $20 \times 10^6$ or greater or about $30 \times 10^6$ or greater, or about $40 \times 10^6$ or greater or about $50 \times 10^6$ or greater.

Embodiment 6

The graphene oxide according to any one of embodiments 1-5, wherein said graphene oxide has an atomic % concentration of oxidized groups (C=O) on the graphene oxide surface of greater than about 11 or greater than about 12, or greater than about 12.6, or greater than about 15, or greater than about 16.3, or greater than about 20, or greater than about 25 as determined by XPS.

Embodiment 7

The graphene oxide according to any one of embodiments 1-6, wherein said graphene oxide has an atomic % concentration of oxidized groups (C=O) on the graphene oxide surface of about 12.6 or greater as determined by XPS.

Embodiment 8

The graphene oxide according to any one of embodiments 1—wherein said graphene oxide has an atomic % concentration of oxidized groups (C=O) on the graphene oxide surface of about 16.3 or greater as determined by XPS.

Embodiment 9

The graphene oxide according to any one of embodiments 1-7, wherein said graphene oxide has an atomic % concentration of oxidized groups (C—OH) on the graphene oxide surface of greater than about 5 or greater than about 8, or greater than about 9, or greater than about 13, or greater than about 15, or greater than about 20 as determined by XPS.

Embodiment 10

The graphene oxide according to any one of embodiments 1-8, wherein said graphene oxide has an atomic % concentration of oxidized groups (C—OH) on the graphene oxide surface of about 9.9 or greater as determined by XPS.

Embodiment 11

The graphene oxide according to any one of embodiments 1-9, wherein said graphene oxide has an atomic % concentration of oxidized groups (C—OH) on the graphene oxide surface of about 13.6 or greater as determined by XPS.

Embodiment 12

The graphene oxide according to any one of embodiments 1-11, wherein said graphene oxide is effective to kill gram negative bacteria.

Embodiment 13

The graphene oxide according to any one of embodiments 1-11, wherein said graphene oxide is effective to kill gram positive bacteria.

Embodiment 14

The graphene oxide according to any one of embodiments 1-11, wherein said graphene oxide is effective to kill *E. coli*.

Embodiment 15

The graphene oxide according to any one of embodiments 1-14, wherein said graphene oxide is attached to a solid surface.

Embodiment 16

The graphene oxide of embodiment 15, wherein said graphed oxide is adsorbed to said surface.

Embodiment 17

The graphene oxide of embodiment 16, wherein said graphene oxide is spin-coated on a surface.

Embodiment 18

The graphene oxide of embodiment 15, wherein said graphed oxide is covalently attached to said surface.

Embodiment 19

The graphene oxide of embodiment 18, wherein said graphene oxide is covalently attached to said surface via a linker.

Embodiment 20

The graphene oxide of embodiment 19, wherein said graphene oxide is attached to said surface via a carbodiimide linker.

Embodiment 21

The graphene oxide according to any one of embodiments 15-20, wherein said graphene oxide coats said surface in a coating ranging in thickness form about 1 nm, or from about 2 nm, or from about 3 nm, or from about 4 nm, or from about 5 nm, or from about 6 nm, or from about 7 nm up to about 100 nm, or up to about 75 nm, or up to about 50 nm, or up to about 40 nm, or up to about 30 nm, or up to about 25 nm.

Embodiment 22

The graphene oxide according to any one of embodiments 15-21, wherein said surface comprises a glass surface, a plastic surface, or a metal surface.

Embodiment 23

The graphene oxide according to any one of embodiments 15-22, wherein said surface comprises a surface of a catheter.

Embodiment 24

The graphene oxide according to any one of embodiments 15-22, wherein said surface comprise a surface of biological implant.

Embodiment 25

The graphene oxide of embodiment 24, wherein said implant is selected from the group consisting of a dental implant, an encapsulated implantable drug delivery system, an implanted canula, and an orthopedic implant.

Embodiment 26

The graphene oxide of embodiment 25, wherein said biological implant comprises an orthopedic implant.

Embodiment 27

The graphene oxide of embodiment 26, wherein said biological implant comprises an orthopedic implant selected from the group consisting of an artificial joint, a bone screw, and a bone nail.

Embodiment 28

The graphene oxide of embodiment 27, wherein said orthopedic implant comprises an orthopedic implant selected from the group consisting of an Austin-Moore prosthesis, Baksi's prosthesis, Charnley prosthesis, Condylar blade plate, Ender's nail, Grosse-Kempf (GK) nail, Harrington rod, Hartshill rectangle, Insall Burstein prosthesis, Richard N. W. Wohns interspinous implant, Kirschner wire, Kuntscher nail, Luque rod, Moore's pin, Neer's prosthesis, Rush nail, Smith Peterson (SP) nail, Smith Peterson nail with McLaughlin's plate, Seidel nail, Souter's prosthesis, Steffee plate, Steinmann pin, Swanson prosthesis, Talwalkar nail, and Thompson prosthesis.

Embodiment 29

The graphene oxide according to any one of embodiments 1-14, wherein said graphene oxide is in a solution or suspension or dispersion, or emulsion.

Embodiment 30

The graphene oxide according to any one of embodiments 1-14, wherein said graphene oxide is provided in a gel.

Embodiment 31

The graphene oxide of embodiment 30, wherein said graphene oxide is provided in a hydrogel.

Embodiment 32

The graphene oxide according to any one of embodiments 1-14, wherein said graphene oxide is a component of a composite or nanocomposite.

Embodiment 33

The graphene oxide of embodiment 32, wherein said composite or nanocomposite is selected from the group consisting of a metal composite or nanocomposite, metal oxide composite or nanocomposite, a polymer composite or nanocomposite, a quaternary phosphonium salt composite or nanocomposite, and a chelator composite or nanocomposite.

Embodiment 34

The graphene oxide of embodiment 33, wherein said composite comprises a metal.

Embodiment 35

The graphene oxide of embodiment 34, wherein said composite or nanocomposite comprises a metal composite selected from group consisting of graphene oxide and silver, graphene oxide and copper, graphene oxide and gold, graphene oxide, and lanthanum.

Embodiment 36

The graphene oxide of embodiment 33, wherein said composite or nanocomposite comprises a metal oxide.

Embodiment 37

The graphene oxide of embodiment 36, comprises a metal oxide selected from the group consisting of $TiO_2$, ZnO, $Fe_3O_4$, $SnO_2$.

Embodiment 38

The graphene oxide of embodiment 34, wherein said composite or nanocomposite comprises a polymer.

Embodiment 39

The graphene oxide of embodiment 38, wherein said composite comprises a polymer selected from the group consisting of poly-N-vinyl carbazole (PVK), chitosan, and PVK.

Embodiment 40

The graphene oxide according to any one of embodiments 1-14, wherein said graphene oxide is additionally functionalized with polyethylenimine (PEI) and/or PEG, and/or PVA, and/or polydopamine.

Embodiment 41

The graphene oxide according to any one of embodiments 1-14, wherein said graphene oxide is attached to fibers or to nanofibers.

Embodiment 42

The graphene oxide according to any one of embodiments 1-14, wherein said graphene oxide is a component of a three-component nanohybrid.

Embodiment 43

The graphene oxide of embodiment 41, wherein said three-component nanohybrid comprises a dimensional GO-Au@Ag nanohybrid.

Embodiment 44

The graphene oxide of embodiment 41, wherein said three-component nanohybrid comprises a GO-poly(acrylic acid)-Ag nanohybrid.

Embodiment 45

The graphene oxide of embodiment 41, wherein said three-component nanohybrid comprises a GO-polydopamine-Ag nanohybrid.

Embodiment 46

The graphene oxide according to any one of embodiments 1-14, wherein said graphene oxide is a component of a tissue engineering scaffold.

Embodiment 47

The graphene oxide of embodiment 46, wherein said scaffold comprises a protein or carbohydrate scaffold.

Embodiment 48

The graphene oxide of embodiment 47, wherein said scaffold comprises one or more materials selected from the group consisting of collagen, chitosan, hyaluronic acid, fibrin, and gelatin.

Embodiment 49

The graphene oxide of embodiment 47, wherein said scaffold comprises scaffold comprises a hyalomatrix composed of silicone and hyaluronic acid.

Embodiment 50

The graphene oxide of embodiment 46, wherein said scaffold comprises a synthetic scaffold.

Embodiment 51

The graphene oxide of embodiment 50, wherein said scaffold comprise one or more materials selected from the group consisting of glycolic acid derivatives, lactic acid derivatives, and other polyester derivatives.

Embodiment 52

The graphene oxide of embodiment 50, wherein said scaffold comprises a copolymer of 1-lactide and epsilon-caprolactone.

Embodiment 53

The graphene oxide of embodiment 50, wherein wherein said scaffold comprises a polyglycolic acid mesh coated with a copolymer of poly[epsilon-caprolactone-1-lactide].

Embodiment 54

The graphene oxide according to any one of embodiments 1-14, wherein said graphene oxide is incorporated into a bandage and/or wound dressing.

Embodiment 55

The graphene oxide according to any one of embodiments 1-14, wherein said graphene oxide is incorporated into a water filter.

Embodiment 56

A method of killing and/or inhibiting the growth and/or proliferation of a microorganism said method comprising contacting said microorganism, or a biofilm containing said microorganism with an effective amount of a graphene oxide according to any one of embodiments 1-14, or a composition comprising a graphene oxide according to any one of embodiments 1-14, or a device coated with a graphene oxide according to any one of embodiments 1-14.

Embodiment 57

The method of embodiment 56, wherein said method comprises contacting said microorganism or biofilm with an article of manufacture wherein said graphene oxide is attached a surface comprising said article of manufacture.

Embodiment 58

The method of embodiment 57, wherein said graphed oxide is adsorbed to said surface.

Embodiment 59

The method of embodiment 58, wherein said graphene oxide is spin-coated on said surface.

Embodiment 60

The method of embodiment 57, wherein said graphene oxide is covalently attached to said surface.

Embodiment 61

The method of embodiment 60, wherein said graphene oxide is covalently attached to said surface via a linker.

Embodiment 62

The method of embodiment 61, wherein said graphene oxide is attached to said surface via a carbodiimide linker.

Embodiment 63

The method according to any one of embodiments 57-62, wherein said graphene oxide coats said surface in a coating ranging in thickness form about 1 nm, or from about 2 nm, or from about 3 nm, or from about 4 nm, or from about 5 nm, or from about 6 nm, or from about 7 nm up to about 100 nm, or up to about 75 nm, or up to about 50 nm, or up to about 40 nm, or up to about 30 nm, or up to about 25 nm.

Embodiment 64

The method according to any one of embodiments 57-63, wherein said surface comprises a glass surface, a plastic surface, or a metal surface.

Embodiment 65

The method according to any one of embodiments 57-64, wherein said surface comprises a surface of a catheter.

Embodiment 66

The method according to any one of embodiments 57-64, wherein said surface comprise a surface of biological implant.

Embodiment 67

The method of embodiment 66, wherein said implant is selected from the group consisting of a dental implant, an encapsulated implantable drug delivery system, an implanted canula, and an orthopedic implant.

Embodiment 68

The method of embodiment 67, wherein said biological implant comprises an orthopedic implant.

Embodiment 69

The method of embodiment 68, wherein said biological implant comprises an orthopedic implant selected from the group consisting of an artificial joint, a bone screw, and a bone nail.

Embodiment 70

The method of embodiment 69, wherein said orthopedic implant comprises an orthopedic implant selected from the group consisting of an Austin-Moore prosthesis, Baksi's prosthesis, Charnley prosthesis, Condylar blade plate, Ender's nail, Grosse-Kempf (GK) nail, Harrington rod, Hartshill rectangle, Insall Burstein prosthesis, Richard N. W. Wohns interspinous implant, Kirschner wire, Kuntscher nail, Luque rod, Moore's pin, Neer's prosthesis, Rush nail, Smith Peterson (SP) nail, Smith Peterson nail with McLaughlin's plate, Seidel nail, Souter's prosthesis, Steffee plate, Steinmann pin, Swanson prosthesis, Talwalkar nail, and a Thompson prosthesis.

Embodiment 71

The method of embodiment 56, wherein said method comprises contacting said microorganism or biofilm with a solution or suspension or dispersion, or emulsion containing said graphene oxide.

Embodiment 72

The method of embodiment 56, wherein said method comprises contacting said microorganism or biofilm with a gel comprising said graphene oxide.

Embodiment 73

The method of embodiment 30, wherein said gel comprises a hydrogel.

Embodiment 74

The method of embodiment 56, wherein said method comprises contacting said microorganism or biofilm with a composite or nanocomposite comprising said graphene oxide.

Embodiment 75

The method of embodiment 74, wherein said composite or nanocomposite is selected from the group consisting of a metal composite or nanocomposite, metal oxide composite or nanocomposite, a polymer composite or nanocomposite, a quaternary phosphonium salt composite or nanocomposite, and a chelator composite or nanocomposite.

Embodiment 76

The method of embodiment 75, wherein said composite comprises a metal.

Embodiment 77

The method of embodiment 76, wherein said composite or nanocomposite comprises a metal composite selected from group consisting of graphene oxide and silver, graphene oxide and copper, graphene oxide and gold, graphene oxide, and lanthanum.

Embodiment 78

The method of embodiment 75, wherein said composite or nanocomposite comprises a metal oxide.

Embodiment 79

The method of embodiment 78, comprises a metal oxide selected from the group consisting of $TiO_2$, $ZnO$, $Fe_3O_4$, and $SnO_2$.

Embodiment 80

The method of embodiment 75, wherein said composite or nanocomposite comprises a polymer.

Embodiment 81

The method of embodiment 80, wherein said composite comprises a polymer selected from the group consisting of poly-N-vinyl carbazole (PVK), chitosan, and PVK.

Embodiment 82

The method of embodiment 56, wherein said method comprises contacting said microorganism or biofilm with a bandage or wound dressing comprising said graphene oxide.

Embodiment 83

The method of embodiment 56, wherein said method comprises contacting said microorganism or biofilm with a water filer incorporating said graphene oxide.

Embodiment 84

The method according to any one of embodiments 56-83, wherein said microorganism comprises one or more microorganisms selected from the group consisting of a fungus, a virus, a protozoan, and a bacterium.

Embodiment 85

The method of embodiment 84, wherein said bacterium comprises a gram negative bacterium.

Embodiment 86

The method of embodiment 84, wherein said bacterium comprises a gram positive bacterium.

Embodiment 87

The method of embodiment 84, wherein said bacterium comprises a drug-resistant bacterium.

Embodiment 88

The method of embodiment 87, wherein said bacterium comprises a drug-resistant bacterium selected from the group consisting of Multidrug-Resistant *Acinetobacter*, Drug-Resistant *Campylobacter*, Fluconazole-Resistant *Candida*, Extended Spectrum Enterobacteriaceae (ESBL), Vancomycin-Resistant *Enterococcus* (VRE), Multidrug-Resistant *Pseudomonas Aeruginosa*, Drug-Resistant Non-Typhoidal *Salmonella*, Drug-Resistant *Salmonella* Serotype *Typhi*, Drug-Resistant *Shigella*, Methicillin-Resistant *Staphylococcus Aureus* (MRSA), Drug-Resistant *Streptococcus Pneumoniae*, and Drug-Resistant Tuberculosis.

Embodiment 89

The method of embodiment 87, wherein said bacterium is Methicillin-Resistant *Staphylococcus Aureus* (MRSA).

Embodiment 90

The method of embodiment 84, wherein said bacterium comprises a bacterium selected from the group consisting of *Acinetobacter baumannii* (*A. baumannii*), *Actinomyces naeslundii* (*A. naeslundii*), *Aspergillus niger* (*A. niger*), *Bacteroides fragilis* (*B. fragilis*), *Bacillus subtilis* (*B. subtilis*), *Candida albicans* (*C. albicans*), *Clostridium difficile* (*C. difficile*), *Corynebacterium jeikeium* (*C. jeikeium*), *Campylobacter jejuni* (*C. jejuni*), *Escherichia coli* (*E. coli*), *Enterococcus faecalis* (*E. faecalis*), *Fusobacterium nucleatum* (*F. nucleatum*), *Lactobacillus acidophilus* (*L. acidophilus*), *Legionella pneumophila* (*L. pneumophila*), (*Micrococcus luteus*) *M. luteus*, *Mycobacterium smegmatis* (*M. smegmatis*), *Malassezia furfur* (*M. furfur*), Methicillin-resistant *Staphylococcus aureus* (MRSA), *Myxococcus xanthus* (*M. xanthus*), *Pseudomonas aeruginosa P. aeruginosa*, *Porphyromonas gingivalis* (*P. gingivalis*), *Progeussmirabilis* (*P. mirabilis*), *S. epidermidis* (*S. epidermidis*), *Streptococcus mutans* (*S. mutans*), *Streptococcus pneumoniae* (*S. pneumoniae*), *Treponema denticola* (*T. denticola*), and *Trichophyton rubrum* (*T. rubrum*).

Embodiment 91

The method of embodiment 84, wherein said bacterium comprises *P. acnes*.

BRIEF DESCRIPTION OF THE DRAWINGS

FIG. 2A) XPS spectra of oxidized groups on the GO surface. XPS was performed by the stepwise (50 meV) acquisition of high resolution spectra of the C is region. FIG. 2B) Detection of .C on GO surface by EPR. EPR was used to assess the .C density on GO surface by testing 5 mg of each of the dried GO samples by an X-band Bruker ELEXYS 580 spectrometer with g value of 2.0029. FIG. 2C) Visualizing the morphology of GO samples by AFM. AFM images were obtained by placing a drop of the GO solution (10 µg/mL) on Si wafers that were pretreated with a 2.5 mM APTES aqueous solution. After washing with water and drying with N2, AFM images were obtained in a Thermo Microscopes Autoprobe CP-Research AFM in tapping mode with conical probes.

FIG. 3A) Comparison of bacterial killing by GO and antibiotics in sensitive (wild type) and AR bacteria. The resistance of bacteria was demonstrated by comparing the killing effect of antibiotics (ampicillin or erythromycin) in sensitive and AR *E. coli* (upper left panel) and *L. crispatus* (lower left panel) after incubation at 37° C. for 24 h; the bactericidal effects of GO were compared with ampicillin in AR *E. coli* (upper right panel) and erythromycin in AR *L. crispatus* (lower right panel). Cell growth was evaluated by measuring bacterial OD at 600 nm. * $p<0.05$ compared to ampicillin or erythromycin. FIG. 3B) Bacterial killing effects of GO samples in resistant *E. coli*. To determine the bacterial killing by GO samples, AR *E. coli* were exposed to 8-500 µg/mL rGO-2, rGO-1, GO, hGO-1 and hGO-2 at 37° C. for 24 h. * $p<0.05$ compared to GO. FIG. 3C) Calculation of the correlation coefficient between .C density and bacteria killing. Pearson's analysis was used to evaluate the correlation between the rate of cell growth and the absorbance peak area of .C on the GO surface.

FIG. 5A) Determination of the pro-oxidative potential of GO samples by an abiotic DCF assay. To assess the oxidation potential of GO samples, 95 µL aliquots of 25 µg/mL DCF were added into each well of a 96 well black bottom plate and mixed with 5 µL of GO suspensions at 5 mg/mL, followed by 2 h incubation. DCF fluorescence emission spectra were recorded using a SpectraMax M5 microplate reader with an excitation wavelength of 490 nm. FIG. 5B) Confocal imaging of GO-induced lipid peroxidation in AR E. coli. To assess lipid peroxidation, AR E. coli, prior exposed to 250 µg/mL GO samples or 10 µM cumene hydroperoxide, was stained by using the IMAGE-IT® Lipid Peroxidation Sensor kit and Hoechst 33342 dye before performance of confocal microscopy. The microscopy was carried out using a Texas Red filter to visualize the reduced dye and a FITC filter to visualize the oxidized dye. FIG. 5C) Quantification of cells with lipid peroxidation by flow cytometry. Flow cytometry was carried out on a FACS Vantage SE flow cytometer to determine the percentage cells undergoing membrane lipid peroxidation. FIG. 5D) β-galactosidase release in GO-treated bacteria. The permeability of cytoplasmic membrane was evaluated using a luminescent β-galactosidase substrate to measure the activity of released β-galactosidase from E. coli treated by 250 rig/mL GO suspensions. * p<0.05 compared to GO treatment. FIG. 5E) Schematic image to explain the bactericidal effect of GO including membrane association and lipid peroxidation.

FIG. 6A) AFM imaging of hGO-2 coated substrates. A series of substrates (S1, S2, S3 and S4) with different GO coverage and thickness were characterized by AFM. FIG. 6B) SEM imaging of changes in the bacterial morphology after incubation with the hGO-2 coated substrate. FIG. 6C) Visualization and D) quantification of bacterial death on hGO-2 films by confocal microscopy. Following 6 h incubation of AR E. coli with substrates S1 to S4, the cells were stained with PI, fixed and washed with 70% ethanol to determine the percentages of dead cells on substrates. The morphological changes of bacteria were visualized by SEM. * p<0.05 compared to control.

FIG. 7A) Schematic to describe hGO-2 coating of catheters as well as product images. A complete coating cycle involves the amination of catheter surface by APTES and conjugation of the hGO-2 to the amine groups. A series of hGO-2 coated catheters were prepared through multicycle coating. The catheter surfaces grow darker with incremental rounds of coating. FIG. 7B) In situ visualization of E. coli bacteria embedded on coated catheters. Catheters were immersed in the bacterial suspensions to allow bacterial attachment to the catheter surface. After 6 h incubation, the catheters were treated with 2% glutaraldehyde, followed by 70% ethanol washing to remove residual salts and Au/Pt coating. The morphology of E. coli on catheters was observed by SEM. Arrows and the dash-line areas show the damaged bacteria. FIG. 7C) β-galactosidase release from bacteria grown on coated catheters. The β-galactosidase release from embedded bacteria on catheter surfaces was determined after 2 h incubation.

FIG. 7 D) Assessing the growth of bacteria retrieved from the coated catheter surfaces by CFU assay. After settling of bacteria on catheter surfaces, they were incubated for 1, 3 and 6 h. Then the retrieved bacteria from catheter surfaces were serially diluted and spread on the agar plates for 24 h incubation. The images show the growing colonies from uncoated or hGO-2 coated surfaces at each time point at same dilutions (left panel). CFU were calculated by desired colony numbers (20-300) at appropriate dilutions (right panel).

FIG. 18A) AFM images. FIG. 18B) Confocal Raman spectra. FIG. 18C) Assessment of carbon radical formation, quantification by EPR, and schematic describing the link to ROS generation. FIG. 18D) Abiotic glutathione (GSH) assay. AFM samples were prepared by placing a drop of the GO solution on Si wafers that were pretreated with an APTES aqueous solution. After washing with water and drying under $N_2$, AFM images were obtained in an Asylum Cypher ES AFM, used in tapping mode with conical probes. Confocal Raman analysis was performed in a Renishaw inVia Raman microscope system equipped with a 514.5 nm Ar laser. Carbon radicals form during the hydration process, which leads to opening of epoxy rings by nucleophiles in the aqueous solution. The presence of carbon radicals was assessed by an X-band Bruker ELEXYS 580 electron paramagnetic resonance (EPR) spectrometer. The schematic shows how the reactive carbon radicals could generate superoxide in the presence of molecular dioxygen, with subsequent ability to oxidize the GSH thiol groups. An abiotic GSH-Glo™ glutathione assay was used to assess the pro-oxidative potential of GO samples by luminescence measurement in a SpectraMax M5 microplate spectrophotometer.

FIG. 19A) Visualizing the interactions of GO with THP-1 cells by TEM. FIG. 19B) confocal imaging of FITC-BSA labeled GO samples in BEAS-2B cells. After exposure to rGO-2, GO or hGO-2 for 16 h, the cells were washed, fixed and stained for TEM viewing, as described in the Method section. For confocal viewing of the interactions of the labeled nanosheets with the cells, the various GO samples were incubated with the cells at 25 µg/mL for 16 h before washing and staining with Hoechst 33342 dye (blue) and Alexa fluor 594-labeled WGA antibody. Samples were viewed under a confocal microscope (Leica Confocal SP2 1P/FCS).

FIG. 20A) Confocal images to demonstrate the generation of lipid peroxidation by the various GO samples. FIG. 20B) flow cytometry assessment to quantify the percentage of cells undergoing lipid peroxidation. FIG. 20C) Red blood cell hemolysis by GO samples. To assess lipid peroxidation, THP-1 cells were treated with 100 µg/mL GO for 16 h or 10 µM cumene hydroperoxide (positive control) for 1 h. Cells were stained with 10 µM IMAGE-IT® Lipid Peroxidation Sensor Lipid Peroxidation Sensor according to the manufacturer's instructions, as well as co-stained with Hoechst 33342 for 30 min. After staining and washing, fluorescence readings were recorded to assess the reduction or oxidation status of the dye at excitation/emission wavelengths of 581/591 nm (Texas Red® filter set) and 488/510 nm (traditional FITC filter), respectively. Flow cytometry analysis was carried out in a FACS Vantage SE flow cytometer. The hemolysis assay was performed by incubation of freshly prepared mouse red blood cells with GO nanosheets. Following RBC centrifugation, the supernatants were collected and hemoglobin content was determined by measuring absorbance at 540 nm using a UV-VIS spectrometer. $*p<0.05$ compared to Ctrl, $\#p<0.05$ compared to pristine GO.

FIG. 21A) Cell viability assessment in in THP-1 and BEAS-2B cells by the MTS assay. FIG. 21B) Calculation of the correlation coefficient of the cytotoxicity results versus carbon radical measurement. FIG. 21C) heat map display to show the hierarchical ranking of the effects of the various library materials on cellular toxicity, membrane peroxidation and RBC leakage. For cellular viability assessment, a MTS assay was used to assess the impact of 0-200 µg/mL of each GO suspension in THP-1 or BEAS-2B cells over 48 h. $*p<0.05$ compared to Ctrl, $\#p<0.05$ compared to pristine GO. The heat maps were established using one-way ANOVA analysis to evaluate the different cellular response parameters at 0-200 µg/mL, as described in the Methods section. $*p<0.05$ compared to Ctrl, $\#p<0.05$ compared to pristine GO.

FIG. 22A) Raman microscopy to assess the uptake of GO by BALF macrophages. FIG. 22B) Confocal imaging to assess lipid peroxidation in BALF macrophages. FIG. 22C) Flow cytometry analysis to quantify the percentage of cells undergoing lipid peroxidation. FIG. 22D) PI staining to assess membrane permeability in primary alveolar macrophages. Animal exposure to rGO-2, GO and hGO-2 nanosheets was performed by using oropharyngeal aspiration of 2 mg/kg of each of the samples. Animals were sacrificed after 40 h to collect primary alveolar macrophages. Typical G and D bands of GO nanosheets were obtained by conducting confocal Raman microscopy. To determine the percentage of PI-positive cells, the recovered BALF macrophages were seeded in 8-well chamber or 6-well plate for 2 h, stained with 1 µg/mL PI and fixed for confocal imaging. $*p<0.05$ compared to Ctrl, $\#p<0.05$ compared to pristine GO.

FIG. 23A) Differential cell counts in the BALF of exposed animals. FIG. 23B) H&E staining to visualize pulmonary inflammation. FIG. 23C) Cytokine release in the BALF. BALF was collected from animals exposed to 2 mg/kg of the various GO sheets for 40 h, as described in FIG. 22A-22D. MCP-1 and LIX levels in the BALF were analyzed by ELISA. $*p<0.05$ compared to Ctrl, $\#p<0.05$ compared to pristine GO.

FIG. 27A) Caspase-3 and (FIG. 27B) TUNEL staining in lung sections. The lung tissues from mice exposed to 2 mg/kg GO samples for 40 h were fixed in formalin for 24 h, followed by 24 h treatment in 70% ethanol before ICC staining of fragmented DNA and caspase-3.

DETAILED DESCRIPTION

Figure 1:
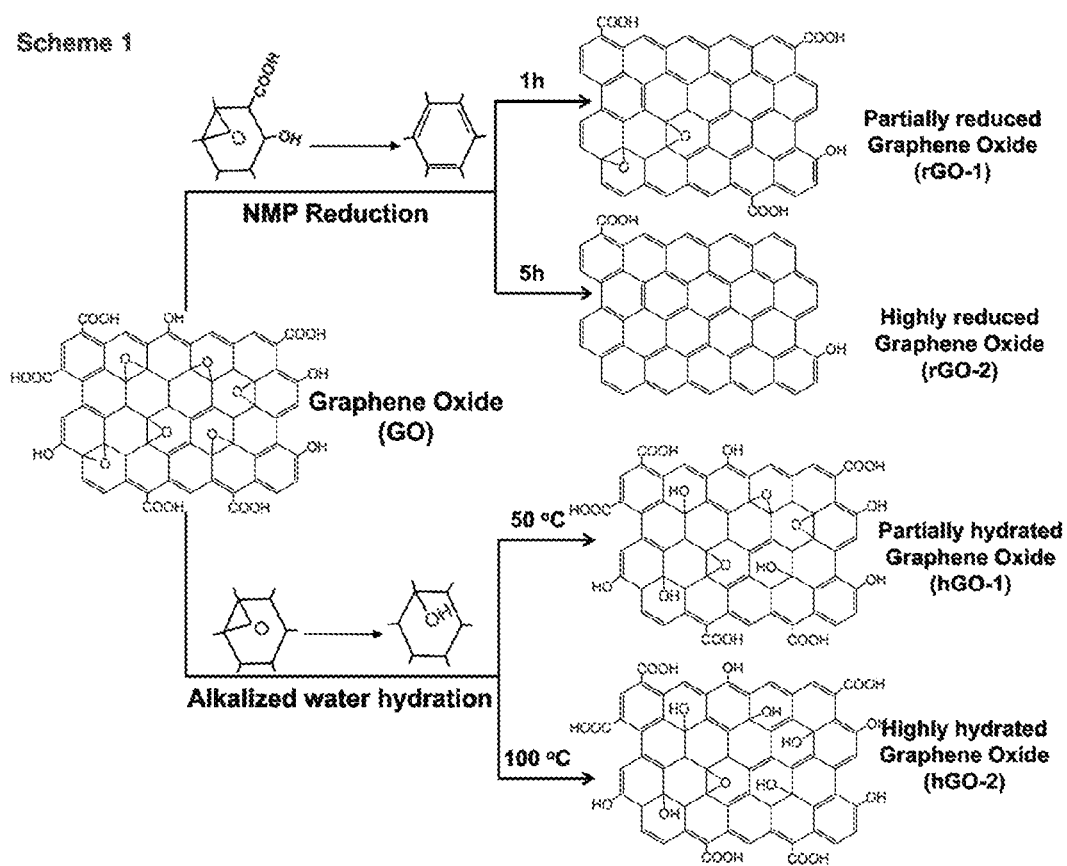
FIG. 1 illustrates a scheme for the synthesis of reduced and hydrated GOs. GO was synthesized by a modified Hummers method. rGO-1 and rGO-2 were synthesized by solvothermal reduction of GO in NMP at 150° C. for 1 or 5 h, respectively. To prepare hGO-1 and hGO-2, GO was hydrated in aqueous alkalized solution at 50° C. or 100° C. for 24 h. Reaction of the epoxy groups with nucleophiles leads to the opening of these rings and the generation of hydroxyl groups (as well as —C radicals shown in FIG. 2B).

While the antibacterial properties of graphene oxide (GO) have been demonstrated across a spectrum of bacteria, the critical role of functional groups has been unclear. To address this important issue, we utilized reduction and hydration methods to establish a GO library with different oxidation, hydroxyl, and carbon radical (.C) levels that was used to study the impact on antibacterial activity.

Using antibiotic-resistant (AR) bacteria as a test platform, it was determined that the .C density is most proximately associated with bacterial killing. Accordingly, hydrated GO (hGO), with the highest .C density, had the strongest antibacterial effects through membrane binding and induction of lipid peroxidation. To explore its potential applications, we demonstrated that coating of catheter and glass surfaces with hGO is capable of killing drug-resistant bacteria. In summary, .C is the principle surface moiety that can be utilized for clinical applications of GO-based antibacterial coatings.

Accordingly, in various embodiments functionalized graphene oxide(s) are provided that demonstrate improved antimicrobial activity, where the graphene oxide(s) are functionalized to increase carbon radical (.C) density. In certain embodiments the antimicrobial activity of the graphene oxide(s) are proportional to the carbon radical density. In certain embodiments the functionalized graphene oxide shows increased lipid membrane binding and/or induction of lipid peroxidation as compared to unfunctionalized graphene oxide. In certain embodiments the graphene oxide is hydrated. In certain embodiments the graphene oxide shows a carbon radical content as determined by electron paramagnetic resonance (EPR) with an absorbance peak area greater than about $15 \times 10^6$, or about $20 \times 10^6$ or greater or about $30 \times 10^6$ or greater, or about $40 \times 10^6$ or greater or about $50 \times 10^6$ or greater. In certain embodiments the graphene oxide has an atomic % concentration of oxidized groups (C=O) on the graphene oxide surface of greater than about 11 or greater than about 12, or greater than about 12.6, or greater than about 15, or greater than about 16.3, or greater than about 20, or greater than about 25 as determined by XPS. In certain embodiments the graphene oxide has an atomic % concentration of oxidized groups (C=O) on the graphene oxide surface of about 12.6 or greater as determined by XPS. In certain embodiments the graphene oxide has an atomic % concentration of oxidized groups (C=O) on the graphene oxide surface of about 16.3 or greater as determined by XPS. In certain embodiments the graphene oxide has an atomic % concentration of oxidized groups (C—OH) on the graphene oxide surface of greater than about 5 or greater than about 8, or greater than about 9, or greater than about 13, or greater than about 15, or greater than about 20 as determined by XPS. In certain embodiments the graphene oxide has an atomic % concentration of oxidized groups (C—OH) on the graphene oxide surface of about 9.9 or greater as determined by XPS. In certain embodiments the graphene oxide has an atomic % concentration of oxidized groups (C—OH) on the graphene oxide surface of about 13.6 or greater as determined by XPS.

In various embodiments the graphene oxide is effective to kill gram negative bacteria and/or gram positive bacteria.

In various embodiments the functionalized graphene oxide and formulations thereof described herein or compositions thereof, or articles of manufacture bearing the graphene oxide on one or more surfaces are useful as biocidal or biostatic or fungicidal or fungistatic agents and/or virucidal agents in a wide variety of applications.

In various embodiments the graphene oxide(s) described herein can be used directly, provided in a composition/formulation, or attached to the surface of an article of manufacture. Thus, for example, the graphene oxide(s) described herein can be provided in a solution and/or suspension, and/or dispersion, and/or emulsion, e.g., for direct use. In certain embodiments the graphene oxide(s) described herein can be attached (e.g., adsorbed or conjugated) to the surface of an article of manufacture to provide antimicrobial properties to that article of manufacture. Thus, for example, the graphene oxide(s) described herein can be attached to the surface of a catheter, a stent, a canula, an orthopedic implant, a depot drug delivery system, a pacemaker, and the like. In certain embodiments the functionalized graphene oxide(s) described herein are provide on a surface of a dental or an orthopedic implant. Illustrative orthopedic implants include, but are not limited to an Austin-Moore prosthesis (for fracture of the neck of femur), a Baksi's prosthesis (for elbow replacement), a Charnley prosthesis (for total hip replacement), a Condylar blade plate (for condylar fractures of femur), an Ender's nail (for fixing inter-trochanteric fracture), a Grosse-Kempf (GK) nail (for tibial or femoral shaft fracture), a Harrington rod: for fixation of the spine), a Hartshill rectangle (for fixation of the spine), an Insall Burstein prosthesis (for total knee replacement), a Richard N. W. Wohns interspinous implant and implantation instrument (intended to be implanted between two adjacent dorsal spines), a Kirschner wire (for fixation of small bones), a Kuntscher nail (for fracture of the shaft of femur), a Luque rod (for fixation of the spine), a Moore's pin (for fracture of the neck of femur), a Neer's prosthesis (for shoulder replacement), a Rush nail (for diaphyseal fractures of long bone), a Smith Peterson (SP) nail (for fracture of the neck of femur), a Smith Peterson nail with McLaughlin's plate (for inter-trochanteric fracture), a Seidel nail (for fracture of the shaft of humerus), a Souter's prosthesis (for elbow replacement), a Steffee plate (for fixation of the spine), a Steinmann pin (for skeletal traction), a Swanson prosthesis (for the replacement of joints of the fingers), a Talwalkar nail (for fracture of radius and ulna), a Thompson prosthesis (for fracture of the neck of femur), and the like.

In certain embodiments the functionalized graphene oxide(s) described herein are provided as a component of a composite or nanocomposite (e.g., a metal composite or nanocomposite, metal oxide composite or nanocomposite, a polymer composite or nanocomposite, a quaternary phosphonium salt composite or nanocomposite, a chelator composite or nanocomposite, and the like).

Exploitation of Antimicrobial Activity.

In various embodiments the functionalized graphene oxide(s) described herein, and/or compositions or formulations comprising these functionalized graphene oxides are used to kill and/or to inhibit the growth and/or proliferation of any of a wide variety of microbial targets, and/or to treat or prevent microbial infections and diseases related thereto in both plants and animals.

In various embodiments the embodiments the functionalized graphene oxide(s) described herein, and/or compositions or formulations comprising these functionalized graphene oxides described herein exhibit antimicrobial activity, being biostatic or biocidal against a certain microbial targets, including but not limited to, Gram-negative bacteria such as *Acinetobacter baumannii, Escherichia coli, Fusobacterium nucleatum, Pseudomonas aeruginosa, Porphyromonas gingivalis*; Gram-positive bacteria such as *Actinomyces naeslundii, Bacillus subtilis, Clostridium difficile, Enterococcus faecalis, Staphylococcus aureus* (and MRSA), *S. epidermidis, Streptococcus mutans, Streptococcus pneumoniae*; and yeast or fungi such as *Aspergillus niger, Candida albicans, Malassezia furfur*, and *Trichophyton rubrum* (see, e.g., Table 1). Significantly, the various he functionalized graphene oxide(s) described herein, and/or compositions or formulations comprising these functionalized graphene oxides described herein are biostatic or biocidal against clinically relevant pathogens exhibiting multi-drug resistance such as, for example, methicillin-resistant *Staphylococcus aureus* ("MRSA").

TABLE 1

Illustrative target microorganisms and associated pathology.

| | |
|---|---|
| *Acinetobacter baumannii* (*A. baumannii*) | Pathogenic gram-negative *bacillus* that is naturally sensitive to relatively few antibiotics. |
| *Actinomyces naeslundii* (*A. naeslundii*) | Gram positive rod shaped bacteria that occupy the oral cavity and are implicated in periodontal disease and root caries. |
| *Aspergillus niger* (*A. niger*) | A fungal infection that often causes a black mould to appear on some fruit and vegetables but may also infect humans through inhalation of fungal spores. |
| *Bacteroides fragilis* (*B. fragilis*) | Gram positive bacilli that are opportunistic human pathogens, causing infections of the peritoneal cavity, gastrointestinal surgery, and appendicitis via abscess formation, inhibiting phagocytosis. Resistant to a wide variety of antibiotics -- β-lactams, aminoglycosides, and recently many species have acquired resistance to erythromycin and tetracycline. |
| *Bacillus subtilis* (*B. subtilis*) | Gram-positive, catalase-positive bacterium. |
| *Candida albicans* (*C. albicans*) | Causal agent of opportunistic oral and genital fungal infections in humans. |
| *Clostridium difficile* (*C. difficile*) | A gram-positive, anaerobic, spore-forming *bacillus* that is responsible for the development of antibiotic-associated diarrhea and colitis. |
| *Corynebacterium jeikeium* (*C. jeikeium*) | Gram positive, opportunistic pathogen primarily of immunocompromised (neutropenic) patients. Highly resistant to antibiotics |
| *Campylobacter jejuni* (*C. jejuni*) | Gram negative cause of human gastroenteritis/food poisoning. |
| *Escherichia coli* (*E. coli*) | Gram negative rod-shaped bacterium commonly found in the lower intestine of warm-blooded organisms. Certain strains cause serious food poisoning in humans. |
| *Enterococcus faecalis* (*E. faecalis*) | Gram-positive commensal bacterium |
| *Fusobacterium nucleatum* (*F. nucleatum*) | Gram negative schizomycetes bacterium often seen in necrotic tissue and implicated, but not conclusively, with other organisms in the causation and perpetuation of periodontal disease. |
| *Lactobacillus acidophilus* (*L. acidophilus*) | Gram-positive commensal bacterium. |
| *Legionella pneumophila* (*L. pneumophila*) | Gram negative bacterium that is the causative agent of legionellosis or Legionnaires' disease. |
| (*Micrococcus luteus*) *M. luteus* | Gram positive, spherical, saprotrophic bacterium found in soil, dust, water and air, and as part of the normal flora of the mammalian skin. The bacterium also colonizes the human mouth, mucosae, oropharynx and upper respiratory tract. Considered an emerging nosocomial pathogen in immunocompromised patients. |
| *Mycobacterium smegmatis* (*M. smegmatis*) | Gram-variable (acid-fast) soil-dwelling organism utilized as a proxy for *Mycobacterium tuberculosis* during research and development. |
| *Malassezia furfur* (*M. furfur*) | Yeast - cutaneous pathogen. |
| Methicillin-resistant *Staphylococcus aureus* (MRSA) | Any strain of *Staphylococcus aureus* bacteria (gram positive) that is resistant to a one or more members of a large group of antibiotics called the beta-lactams. Responsible for skin and systemic infections. |
| *Myxococcus xanthus* (*M. xanthus*) | Gram negative cells that form biofilms and display primitive social motility and fruiting body organization. |
| *Pseudomonas aeruginosa* *P. aeruginosa* | Gram-negative rod. Frequent opportunistic pathogen and infects burn wounds. Causes ear infections in children. Infects the lungs of cystic fibrosis patients. |
| *Porphyromonas gingivalis* (*P. gingivalis*) | Non-motile, gram-negative, rod-shaped, anaerobic pathogenic bacterium (periodontal disease) |
| *Progeussmirabilis* (*P. mirabilis*) | Gram-negative, facultatively anaerobic bacterium. Causes 90% of all '*Proteus*' infections in humans. |

TABLE 1-continued

Illustrative target microorganisms and associated pathology.

| | |
|---|---|
| S. epidermidis (S. epidermidis) | Gram-positive, coagulase-negative cocci. Nosocomial pathogen associated with infection (biofilm) of implanted medical device. |
| Streptococcus mutans (S. mutans) | Gram-positive, facultatively anaerobic bacterium commonly found in the human oral cavity and is a significant contributor to tooth decay |
| Streptococcus pneumoniae (S. pneumoniae) | Gram-positive, alpha-hemolytic, bile soluble aerotolerant anaerobe. Causal agent for streptococcal pneumonia. |
| Treponema denticola (T. denticola) | Gram-negative oral spirochete associated with the incidence and severity of human periodontal disease. |
| Trichophyton rubrum (T. rubrum) | Most common cause of athlete's foot, jock itch and ringworm. |

The functionalized graphene oxide and formulations thereof described herein or compositions thereof, are useful as biocidal or biostatic or fungicidal or fungistatic agents and/or virucidal agents in a wide variety of applications. For example, the graphene oxide or compositions thereof can be used to disinfect or preserve a variety of materials including medical instruments, foodstuffs, medicaments, cosmetics and other nutrient-containing materials. In certain embodiments the functionalized graphene oxide(s) described herein are particularly useful as bacteriostatic or bactericidal agents against multi-drug-resistant pathogens such as MRSA in a variety of clinical settings.

The functionalized graphene oxide(s) described herein, or compositions thereof, are also useful for the prophylaxis or treatment of microbial infections and diseases related thereto in both plants and animals. Such diseases include, but are not limited to, Gram-negative and Gram-positive bacterial infections, endocarditis, pneumonia and other respiratory infections, urinary tract infections, systemic candidiasis, oral mucositis, fungal infections, biofilm formation or maintenance (e.g., on medical implants), and the like.

Gram Negative Bacteria.

In various embodiments, the functionalized graphene oxide(s) described herein, and/or compositions or formulations comprising these functionalized graphene oxides described herein are effective to kill and/or to inhibit the growth and/or proliferation of gram negative bacteria. The gram negative bacteria include, inter alia, the proteobacteria, a major group of gram-negative bacteria, including *Escherichia coli* (*E. coli*), *Salmonella*, *Shigella*, and other Enterobacteriaceae, *Pseudomonas*, *Moraxella*, *Helicobacter*, *Stenotrophomonas*, *Bdellovibrio*, acetic acid bacteria, *Legionella* etc. Other notable groups of gram-negative bacteria include the cyanobacteria, spirochaetes, green sulfur, and green non-sulfur bacteria.

Medically relevant gram-negative cocci include, but are not limited to, the four types that cause a sexually transmitted disease (*Neisseria gonorrhoeae*), a meningitis (*Neisseria meningitidis*), and respiratory symptoms (*Moraxella catarrhalis, Haemophilus influenzae*).

Medically relevant gram-negative bacilli include, but are not limited to a multitude of species. Some of them cause primarily respiratory problems (*Klebsiella pneumoniae, Legionella pneumophila, Pseudomonas aeruginosa*), primarily urinary problems (*Escherichia coli, Proteus mirabilis, Enterobacter cloacae, Serratia marcescens*), and primarily gastrointestinal problems (*Helicobacter pylori, Salmonella enteritidis, Salmonella typhi*).

Gram-negative bacteria associated with hospital-acquired infections include, but are not limited to *Acinetobacter baumannii*, which cause bacteremia, secondary meningitis, and ventilator-associated pneumonia in hospital intensive-care units.

Gram Positive Bacteria.

In certain embodiments the graphene oxide(s) described herein, compositions comprising these graphene oxide(s) and/or device or surfaces coated with these graphene oxide(s) can be used to kill and/or to inhibit the growth and/or proliferation of gram positive bacteria. Such gram positive bacteria include, but are not limited to enterococci (e.g., *Enterococcus faecalis*, and *E. faecium*), staphylococci (e.g. *Staphylococcus aureus* including, but not limited to MSSA (methicillin susceptible strains) and MRSA (methicillin resistant *Staph aureus*), *Staphylococcus* coagulase-negative species (e.g., *Staph epidermidis, Staph. haemolyticus, Staph lugdunensis, Staph saprophyticus, Staph hominis, Staph capitis*), streptococci including, but not limited to *Streptococcus intermedius, Streptococcus anginosus, Streptococcus constellatus, Streptococcus pneumoniae, Streptobacillus moniliformis, Streptococcus pyogenes* (Groups A, B, C, G, F), *Streptococcus agalactiae* (Group B *streptococcus*), bacillin including, but not limited to *Actinomyces israelii, Arcanobacterium haemolyticum*, bacilli including, but not limited to *Bacillus anthracis, Bacillus cereus, Bacillus subtilis, clostridium* such as *Clostridium difficile, Clostridium perfringens, Clostridium tetani, corynebacterium* such as *Corynebacterium diphtheria, Corynebacterium jeikeium, Corynebacterium urealyticum*. and others such as *Listeria monocytogenes, Lactobacillus* species (e.g. *L. acidophilus, L. brevis, L. buchneri, L. casei, L. fermentum, L. gallinarum, L. gasseri*), *Nocardia* asteroids, *Nocardia brasiliensis, Propionibacterium acnes*, and *Rhodococcus equi*.

Graphene Oxide Composites and/or Nanocomposites.

Graphene-based nanocomposites have emerged as promising antibacterial materials. Nanocomposites can overcome the limitations of the individual components. For example, antibacterial nanomaterials attached to the graphene substrate are more stable and well dispersed. Illustrative composites that can incorporate the functionalized graphene oxide(s) described herein include, but are not limited to two-component and multi-component composites and nanocomposites. Illustrative composites and/or nanocomposites include, but are not limited to, composites containing metals, metal oxides, polymers, quaternary phosphonium salts, chelating agents (e.g., EDTA), and the like/

Illustrative but non-limiting metal-containing composites or nanocomposites comprise a functionalized graphene oxide described herein and one or more metals. Illustrative metal composites include, but are not limited to composites or nanocomposites comprising a graphene oxide described herein and silver (e.g. silver nanoparticles), composites comprising graphene oxide and copper (e.g., copper nanoparticles), composites or nanocomposites comprising a graphene oxide described herein gold, composites or nanocomposites comprising a graphene oxide described herein and lanthanum, and the like.

In certain embodiments composites or nanocomposites comprising a graphene oxide described herein and metal oxide semiconductors, such as $TiO_2$ and ZnO, $SnO_2$, and $Fe_3O_4$, and the like are contemplated.

In certain embodiments composites or nanocomposites comprising a graphene oxide described herein and one or more polymers is contemplated. Illustrative polymers include, but are not limited to poly-N-vinyl carbazole (PVK), PLL, and the like. Other suitable polymers include, but are not limited to chitosan, collagen, cellulose, dextrin, and the like. In certain embodiments the graphene oxide described herein comprises chitosan-modified metal (e.g., gold), and lactoferrin on the GO surface. In certain embodiments the graphene oxide described herein comprises a composite composed of graphene oxide, 4-carboxy benzenediazonium salt, and PLL.

In certain embodiments composites or nanocomposites comprising a graphene oxide described herein where the composite comprises three or more components are contemplated. Illustrative composites include, but are not limited to two-dimensional GO-Au@Ag nanohybrids, GO-polydopamine-Ag hybrid materials, and the like.

Due to their excellent physicochemical and inherent antibacterial properties, the graphene-based nanocomposites have been widely used in many fields, such as biomedicine (as wound dressing, tissue engineering scaffolds, antibacterial packaging, and drug delivery systems), water purification, production of antibacterial paper, and the like. Without being bound to a particular theory, it is believed that using the functionalized graphene oxide described herein can improve any of these uses.

For example, using the functionalized graphene oxide(s) described herein, nanocomposites in the form of paper, fabric, or hydrogel can provide excellent compositions for wound dressing. By way of illustration, in certain embodiments, using the functionalized graphene oxide(s) described herein can be prepared by direct adsorption, radiation-induced crosslinking, and chemical cross-linking. It is believed the resulting composites can show excellent antibacterial activities and good laundering durability with minimal skin irritation. It is noted that such composites fabricated using unfunctionalized GO, were found to inactivate>90% bacteria even after washing 100 times (see, e.g, Karimi et al. (2014) *Cellulose,* 21: 3813-3827)). These prepared antibacterial cotton fabrics are flexible, foldable and reusable, with various potential antibacterial applications (Id.).

The graphene present on the surface of the cotton fabric can significantly improve its electrical conductivity and self-cleaning properties. Moreover, the as-prepared cotton fabrics showed excellent antibacterial activity but no cytotoxic effect on human fibroblasts.

CS-PVA nanofibers containing graphene for wound healing have been prepared (see, e.g. Lu, et al. (2012) *Nanoscale* 4: 2978-2982). Similarly, graphene oxide has been incorporated in a collagen-fibrin composite film for use as wound dressing to accelerate wound healing (see, e.g., Deepachitra et al. (2014) *RSC Adv.* 4: 62717-62727). GO has been incorporated into sodium alginate fibers to enhance strength (see, e.g, He et al. (2012) *Carbohydr. Polym.* 88: 1100-1108). The hybrid film can swell into hydrogel fibers used as as-spun fibers in wound dressing. Fan et al. (2014) *Adv. Funct. Mater.* 24: 3933-3943 described a wound dressing prepared by cross-linking the GO-Ag composites into the polymer hydrogel, which showed excellent antibacterial activity and accelerated the wound-healing rate. The as-prepared hydrogel also showed excellent water-maintaining capacity, biocompatibility, and extensibility, which are necessary for wound care.

Wound dressings have also been prepared with antibacterial property based on graphene quantum dots and a low level of $H_2O_2$. Graphene quantum dots with intrinsic peroxidase-like activity can catalyze the decomposition of $H_2O_2$ into hydroxyl radicals with higher antibacterial activity, thus avoiding the toxicity of H2O2 at high levels in wound disinfection (Sun et al. (2014) *ACS Nano* 8: 6202-6210). Graphene-based nanocomposites can promote the growth of human and mammalian cells, which makes them suitable as tissue engineering scaffolds. GO-chitosan has been used as an antibacterial scaffold for stem cell proliferation (see, e.g., Mazaheri et al. (2014) *Appl. Surf Sci.* 301: 456-462). GO nanosheets have been used as a reinforcing agent in poly (acrylic acid)/gelatin composite hydrogels to obtain a suitable scaffold for tissue engineering and GO has been introduced into the culture medium for bacterial cellulose to obtain GO-bacterial cellulose hydrogels (see, e.g., Faghihi et al. (2014) *J. Appl. Phys.* 115: 083513; Si, et al. (2014) *Macromol. Rapid Commun.* 35: 1706-1711; and the like).

Additionally, graphene nanosheets can be fabricated into high-barrier and thermotolerant nanocomposites to prevent the migration of water vapor, oxygen, and $CO_2$ thereby providing a wide range of applications in antimicrobial packaging.

Graphene has been widely used as an effective nanocarrier to deliver drugs, including antibiotics, because of its rich surface chemistry, high aspect ratio, and ability to cross the plasma membrane (see, e.g., Dreyer et al. (2010) *Chem. Soc. Rev.* 39: 228-240). Biocompatible GO-modified polysebacic anhydride (PSA) hybrids have been prepared and used to release the antibacterial drug levofloxacin. Gentamicin sulfate has been released from methanol-derived graphene. The nanohybrid could be used to treat various topical bacterial infections as a single medication, increasing patient compliance due to its prolonged action (see, e.g., Gao et al. (2011) *RSC Adv.* 1: 1737-1744; Pandey et al. (2011) *Nanoscale* 3: 4104-4108). Similarly, GO-benzylpenicillin anion-intercalated Mg—Al-layered double hydroxide hybrid films and GO-benzylpenicillin-layered double hydroxides GO-balofloxacin nanocomposites, carboxylated graphene-β-cyclodextrin/chlorhexidine acetate (GO-COO-j-CD/CA), have all been prepared as graphene-based drug carriers. Gramicidin (GD)-functionalized GO (GOGD) with antibacterial activities against different bacterial strains has been prepared.

A graphene oxide-Ag nanocomposite-modified porous carbon foam electrode was prepared for water purification (see, e.g., Kumar et al. (2013) *Nanotechnology* 24: 235101). Similarly, prepared AgNPs and Ag@C on graphene oxide has been used as electrodes in a capacitive deionization process to desalinate the seawater into drinking water (see, e.g., Cai et al. (2014) *Mar. Pollut. Bull.* 85: 733-737). A nisin antibacterial peptide-conjugated 3D porous GO membrane for effective separation and inactivation of methicillin-resistant *S. aureus* (MRSA) pathogens from water has been demonstrated (see, e.g., Kanchanapally et al. (2015) *RSC Adv.* 5: 18881-18887).

Graphene-based nanomaterial-modified membrane filters can be used in water treatment due to their enhanced antibacterial properties (see, e.g., Musico et al. (2014) *Chem. Eng.* 2: 1559-1565). Hyperbranched polyethylenimine (HPEI)-GO/polyethersulfone (PES) hybrid ultrafiltration membranes were fabricated via a classical phase inversion method by dispersing HPEI-modified GO in the PES casting solution. The hybrid membranes exhibited excellent mechanical properties and good antibacterial activity, with potential applications beyond water purification or the fractionation of proteins and peptides (see, e.g., Yu et al. (2013) *J. Membr. Sci.* 447: 452-462). Membranes decorated with GO-Ag displayed enhanced synergistic bactericidal effect on *E. coli*. A GO nanomaterial has been used as the filtration medium to eliminate bacteria from fuel. GO and GO-Ag columns can efficiently trap and inactive bacteria while allowing fuel to flow freely.

A graphene-agarose hydrogel using agarose as the cross-linking agent and stabilizer has been fabricated (see, e.g., Wang et al. (2013) *RSC Adv.* 3: 9240-9246). The hydrogel showed significant antibacterial ability, and it has been successfully fabricated into a gel column to purify miniature-scale water. Similarly, an antibacterial GO-Ag hydrogel composed of well-dispersed AgNPs and a porous rGO network was fabricated via a hydrothermal reaction for point-of-use water sterilization. The rGO network was used as the support for AgNPs, which in turn facilitate the formation of the porous hydrogel. The bactericidal filter composed of the GO-Ag hydrogel showed good efficacy against *E. coli*. Moreover, the level of silver in the purified water was found to be much lower than the drinking water standard because silver is held by the graphene oxide (see, e.g., Zeng et al. (2015) *Adv. Funct. Mater.* 25: 4344-4351).

It is believed that any of the foregoing uses and compositions can be improved by incorporation of the functionalized graphene oxide(s) described herein. These applications are intended to be illustrated and non-limiting. Using the teachings provided herein numerous additional applications for the functionalized graphene oxide(s) described herein will be available to one of skill in the art.

EXAMPLES

The following examples are offered to illustrate, but not to limit the claimed invention.

Example 1

Identification and Optimization of Carbon Radicals on Hydrated Graphene Oxide for Ubiquitous Antibacterial Coatings We developed a new approach to change the surface functionalities of graphene oxide in a more systematic fashion to elucidate SARs. It has been shown that solvothermal reduction could quantitatively adjust GO oxidation levels (Dubin et al. (2010) *ACS Nano* 2010, 4(7): 3845-3852), while hydrolysis by alkalized aqueous solvents could open epoxy rings and quantitatively adjust the hydroxyl density (Pavlidis et al. (2014) *Trends Biotechnol.* 32(6): 312-320). While it is also possible that the .C levels could also be impacted by these processes (Khimiya, Chemical Properties of Ethylene Oxide. In Ethylene Oxide, Zimakov, P. V.; Dyment, O. H., Eds. 1967; pp 57-85), this aspect has not been studied.

We hypothesized that quantitative adjustment of GO surface functionalities may allow us to establish structure activity relationships (SARs) for bacterial killing by the various surface groups.

Herein, using reduction and hydration methods, we successfully synthesized a library of GO with different surface functionalities and compared their antibacterial effects in *Escherichia coli* (*E. coli*), which is a popularly used gram-negative bacterium to explore new antibacterial agents and study antibiotic resistance (Tu et al. (2013) *Nat. Nanotechnol.* 8(8): 594-601; Zou et al. (2016) *J. Am. Chem. Soc.* 138(7): 2064-2077). Through detailed characterization and toxicity testing, we identified .C as the functionality that is best associated with the antibacterial effects. The hydration method could quantitatively modulate the .C density, allowing hydrated GO (hGO) with the highest radical levels to exert the most effective antibacterial effects. To explore its potential applications, we coated the surfaces of glass slides and silicone catheters with hGO for proof-of-concept experimentation. Immobilized hGO provided highly effective bactericidal effects in antibiotic-resistant *E. coli*, commensurate with the coating density. These results demonstrate the important role of .C and potential use of GO coatings on medical devices to combat antibiotic resistance.

Results

Establishing a Well-Characterized GO Material Library with Varying Surface Functional Groups.

Recent developments in the functionalization of the GO surface present the opportunity for chemical tuning of these groups for the purpose of directed work functions. Oxidation levels can be modified through the use of reduction processes based on solvothermal or chemical methods for the production of reduced graphene oxide (rGO), which is chemically similar to graphene, albeit not identical (Scheme 1, FIG. 1). During reduction, the variety and evolution of oxygenated species on the GO surface can be tracked by methods such as Raman spectroscopy (Bagri et al. (2010) *Nat. Chem.* 2(7): 581-587), X-ray photoelectron spectroscopy (XPS) (Shen et al. (2013) *Carbon,* 56: 132-138) and electron paramagnetic resonance (EPR) (Yang et al. (2014) *Angew. Chem.-Int. Edit.* 53(38): 10109-10113). It is also possible to use hydration chemistry for opening epoxy rings through hydrolysis, with the ability to change the density of surface hydroxyl groups; this can be achieved by heating GO in an alkaline environment (Scheme 1, FIG. 1).

Figure 2A:
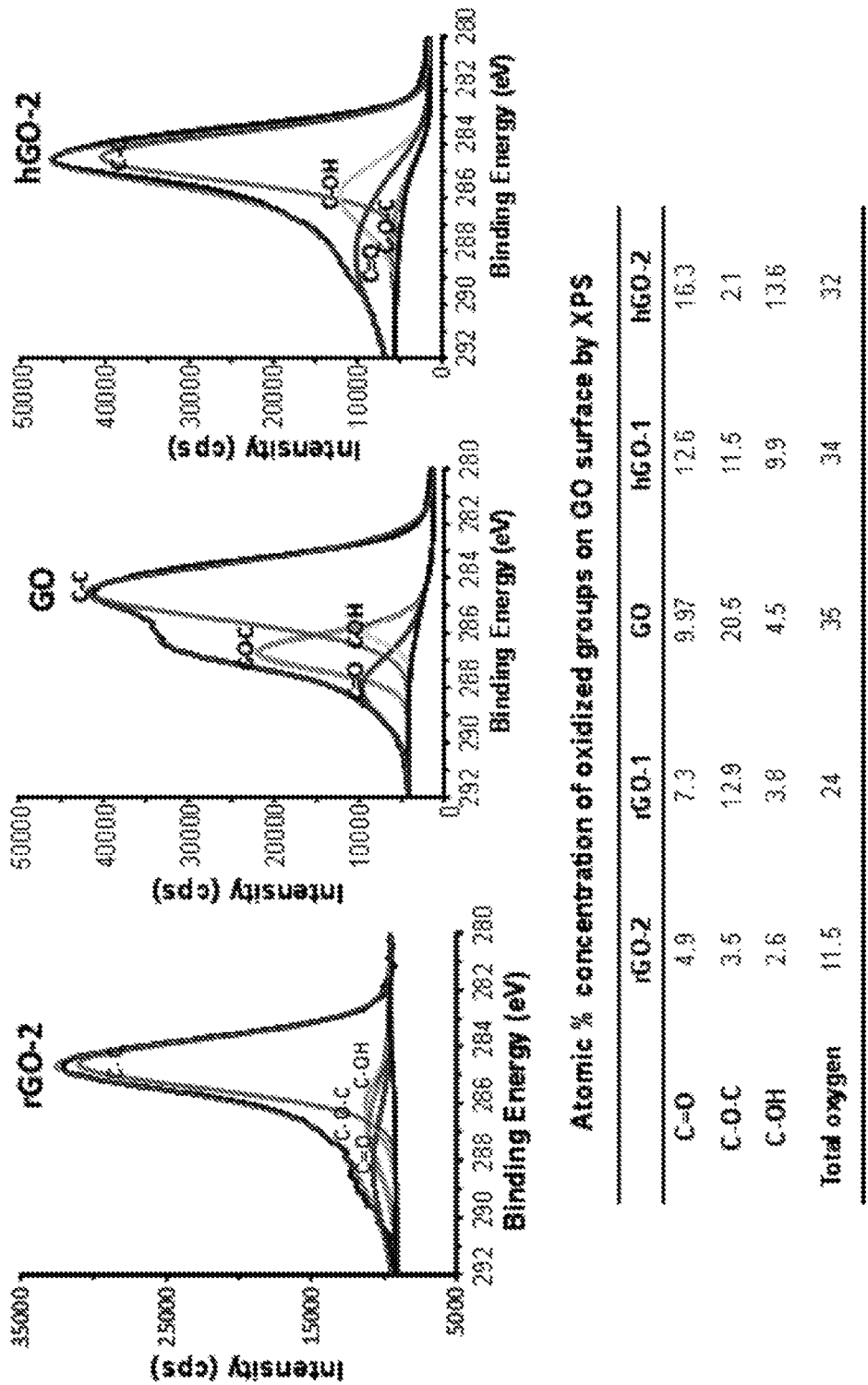
FIGS. 2A-2C illustrate characterization of GO library materials by EPR, XPS and AFM.

In order to assess the SARs most directly involved in bacterial killing, we established a GO material library by using reduction and hydration methods to change surface functionalities. Pristine GO prepared by the classic Hummers method was used as the base material for preparing the library. The total level of oxidized groups on the GO surface was reduced by solvothermal reduction in N-methyl-2-pyrrolidinone (NMP), while heating in alkaline water leads to increasing the hydroxyl density by hydrolyzing the epoxy surface groups (Scheme 1, FIG. 1). Through control of the reaction conditions (time or temperature), we prepared a series of GO samples with quantifiable differences in their oxidation states and surface functional groups. From these materials, we selected two reduced GO (rGO-1 and rGO-2) and two hydrated GO (hGO-1 and hGO-2) samples for comparative study vs. pristine GO. X-ray photoelectron spectroscopy (XPS) was used to determine the levels of oxidized functional groups on the GO surface. The C1s XPS spectra of the rGO-2, GO and hGO-2 sheets (FIG. 2A), show C=C bonds at 284.6 eV, C—OH at 286.5 eV, C—O—C at 287.3 eV and C=O at 288.0 eV, as previously described (Bo et al. (2014) *Sci. Rep.* 4: 4684; Zhang et al. (2012) *Phys. Chem. Chem. Phys.* 14(39): 13670-13675). Analysis of the XPS peaks allowed us to estimate the atomic % of —COOH, —COC—, and —OH groups on the GO surface. This analysis showed that the NMP reduction could significantly reduce the peak intensities of the total oxygen content as well as the % of each oxidized group on the material surface. Different from the reduction process, hydrolysis mainly reduces the C—O—C content on the GO surface. The intensity of the C—O—C peak decreased to 2.1%, while the C—OH peak increased from 4.5 to 13.6% for hGO-2. These changes likely result from the reaction between the epoxy groups and nucleophiles in aqueous solution, leading to the generation of —OH groups. The total oxygen levels remained stable during hydration, likely due to the fact that opening of the epoxy rings will not change the oxygen levels.

Figure 2B:
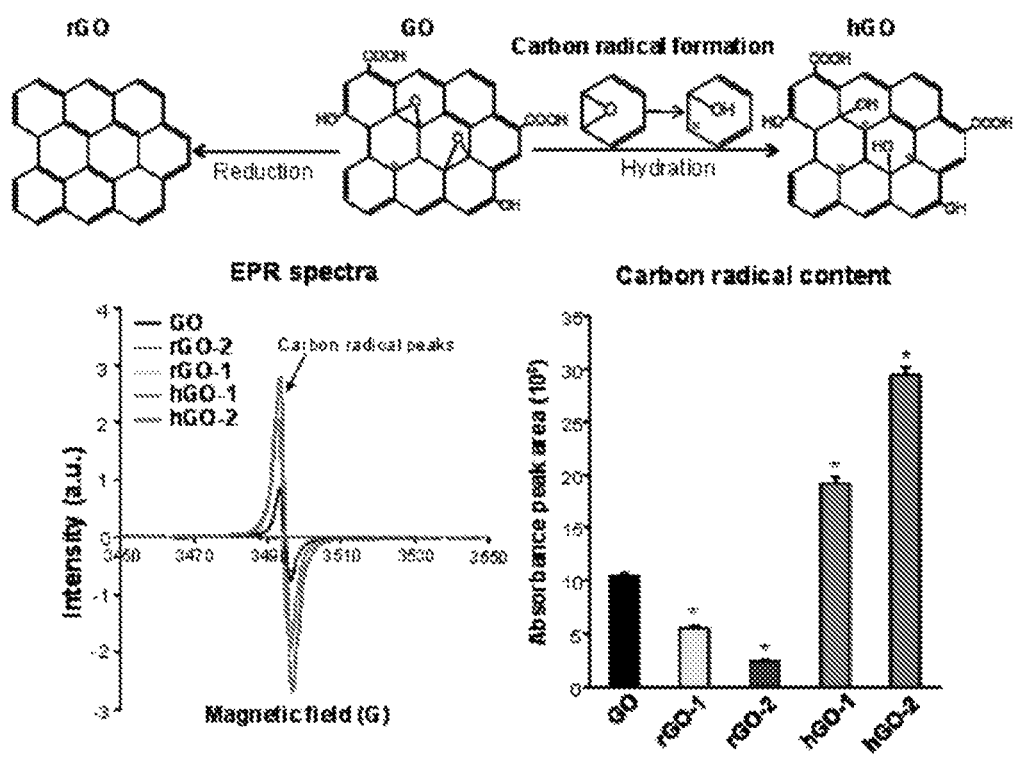
Figure 8:
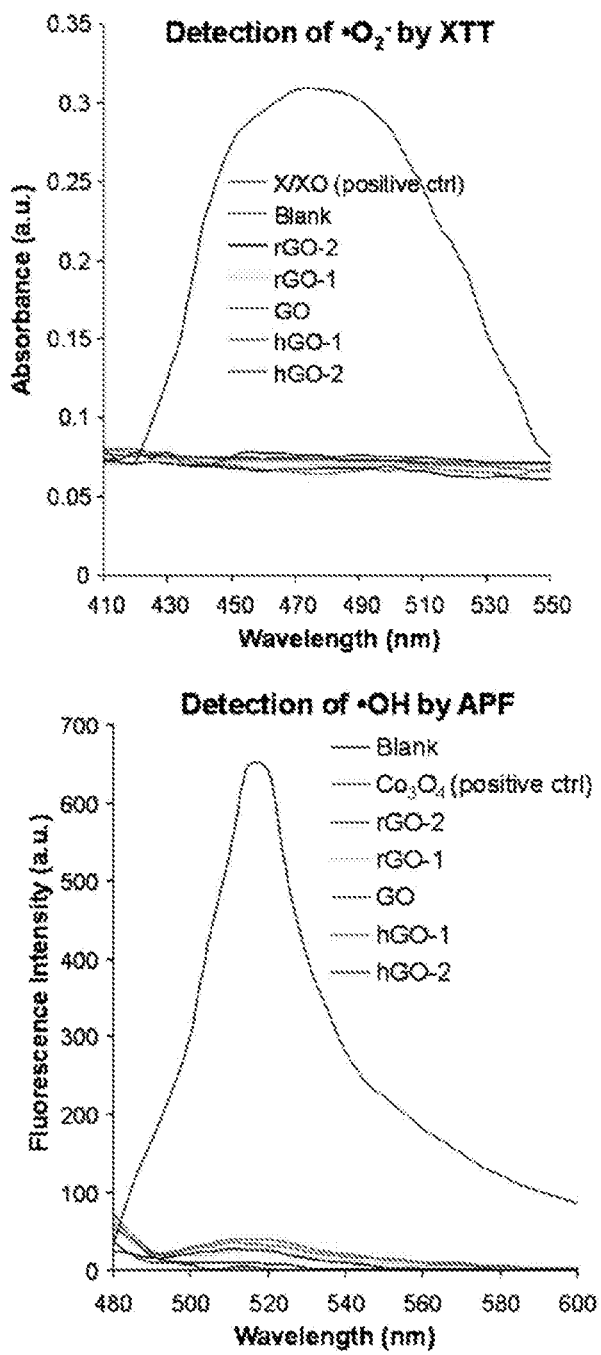
FIG. 8 illustrates detection of residual oxygen radicals including $\chi O_2-$ by XTT assay (top panel) and .OH by APF assay (bottom panel). 5 µL aliquots of 5 mg/mL nanoparticle suspension were incubated with 95 µL 100 µM XTT or 10 µM AFM working solutions in a 96-well black plate for 2 h. Xanthine/xanthine oxidase (X/XO) and $Co_3O_4$ nanoparticles were used as positive controls. APF fluorescence emission spectra were collected at 480-600 nm with an excitation wavelength of 455 nm, while XTT absorbance spectra were recorded in the range of 410-550 nm.

Again, we know that the isolated electrons in the p orbitals of the carbon atom are usually conjugated to the GO backbone by it bonding, which can result in the formation of .$C^{14}$. Thus, we also characterized the .C density on the GO surface through an EPR method. Interestingly, these measurements demonstrated that in addition to the changes in oxygen levels and hydroxyl groups as a result of reduction and hydration chemistry, there is a dramatic change in the density of .C. As shown in FIG. 2B, all GO samples showed a single resonance peak of π-conjugated .C with g=2.0029, which is consistent with a previous report (Yang et al. (2014) Angew. Chem.-Int. Edit. 53(38): 10109-10113). In addition, we ruled out the possibility that the EPR signals on GO samples resulting from the residual oxygen radicals (such as .OH and $O_2$—) by the 3'-(p-aminophenyl) fluorescein (APF) and 3-bis(2-methoxy-4-nitro-5-sulfophenyl)-2H-tetrazolium-5-carboxanilide) (XTT) assays (FIG. 8). hGO samples showed significantly higher EPR peaks than pristine GO (with hGO-2 being the highest), while rGO samples showed a lower radical density than GO. rGO-2 exhibited the weakest EPR signal. These changes suggest that hydrolysis of —COC— groups is accompanied by the generation of .C, which stably exist on the planar GO surface as π-conjugated .$C^{14}$. In addition, we demonstrated that the EPR signals used to establish a role for .C show the utility of reduction and hydration chemistry to quantitatively change the surface functionalities of GO sheets.

Figure 2C:
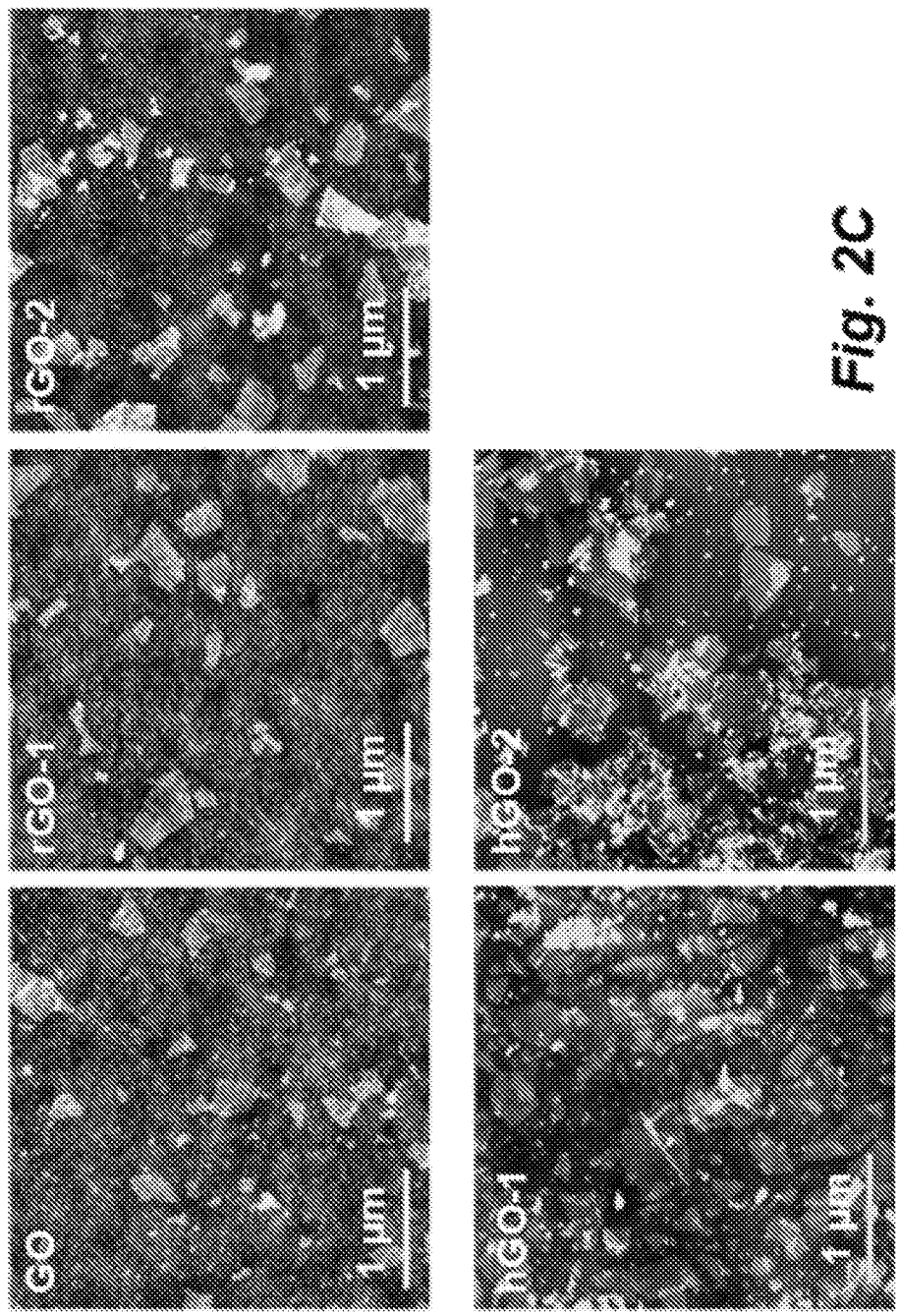
Figure 9:
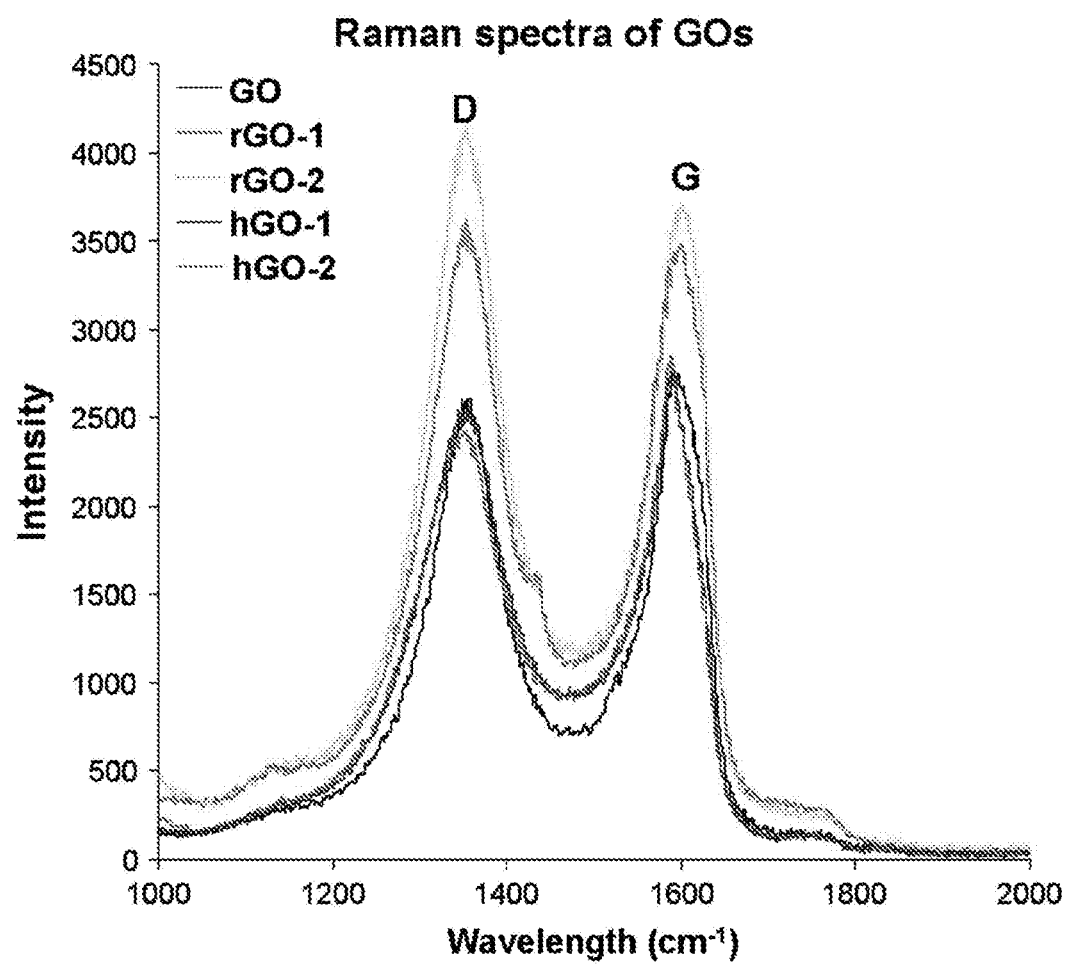
FIG. 9 illustrates the characterization of GO samples by Raman spectroscopy. The signature D and G bands of GO samples were detected using Raman spectroscopy (Renishaw inVia Reflex, Wotton under Edge, UK) with a 785 nm near-infrared diode and a 50× objective lens. Spectra were obtained for 10 seconds exposure time with an accumulation of 2 scans in the wavenumber region 500-2000 cm-1.

We also thoroughly characterized other physicochemical properties of the GO library materials, including primary size, shape, hydrodynamic size and surface charge in aqueous solution. Atomic force microscopy (AFM) showed that all the GO materials were irregularly shaped nanosheets with a lateral size distribution of 50-300 nm (FIG. 2C). Raman spectra demonstrated that rGO, GO and hGO samples preserved the graphene structure, with maintenance of the signature G and D bands (FIG. 9); this suggests that there are no major structural changes during the catalytic modification of the GO surface. We also assessed the hydrodynamic size distribution and zeta potential of the GO materials in different aqueous media. As shown in Table 1, all of the GO nanosheets showed approximately the same hydrodynamic size distribution (400-700 nm) and negative zeta potential values (5 to −19 mV) in the presence of LB or Lactobacilli MRS (Lacto) broths (Table 2).

TABLE 2

Hydrodynamic size and zeta potential of GO samples in aqueous solution.

| Nanoparticles | | GO | rGO-1 | rGO-2 | hGO-1 | hGO-2 |
|---|---|---|---|---|---|---|
| Primary Size (nm) | | 148 | 152 | 148 | 157 | 138 |
| Hydrodynamic Size (nm) | Water | 334.1 ± 3.1 | 378.1 ± 3.9 | 1349.2 ± 8.5 | 307.5 ± 6.7 | 329.8 ± 7.0 |
| | LB | 655.4 ± 95.4 | 615.9 ± 54.9 | 474.9 ± 14.9 | 412.1 ± 4.5 | 533.8 ± 26.6 |
| | Lacto | 443.6 ± 4.6 | 654.9 ± 44.3 | 509.6 ± 6.7 | 367.2 ± 8.4 | 409.5 ± 48.3 |
| Zeta Potential (mV) | Water | −51.7 ± 0.9 | −36.3 ± 1.4 | −24.4 ± 0.7 | −50.6 ± 0.8 | −49.4 ± 0.9 |
| | LB | −18.53 ± 0.6 | −8.7 ± 2.7 | −8.2 ± 2.2 | −16.7 ± 0.8 | −14.7 ± 2.5 |
| | Lacto | −7.5 ± 0.5 | −5.5 ± 1.2 | −6.5 ± 3.6 | −7.9 ± 3.9 | −6.4 ± 2.2 |

Carbon Radical Density is the Determining Factor in the Antibacterial Effects of GO.

To study the killing effects of pristine GO on bacteria, we selected wildtype and antibiotic resistant (AR) E. coli as well as AR Lactobacillus crispatus (L. crispatus) as representative gram-negative and positive bacterial strains, respectively. The AR strains were included in light of the public health relevance of AR bacteria. The chosen E. coli strain is resistant to 24 different types of antibiotics, including ampicillin (Table 3).

TABLE 3

Antibiotic-resistant E. coli are resistant to multiple antibiotics.

| | Antibiotics | Resistant/Susceptible |
|---|---|---|
| Penicillins | Amoxicillin/Clavulanic Acid | R |
| | Ticarcillin | R |
| | Ticarcillin/Clavulanic Acid | Not tested |
| | Piperacillin | R |
| | Ampicillin | R |
| | Ampicillin/Sulbactam | R |
| Cephalosporins | Cefalotin | R |
| | Cefuroxime | R |
| | Cefuroxime Axetil | R |
| | Cefotetan | R |
| | Cefpodoxime | R |
| | Cefotaxime | R |
| | Ceftizoxime | R |
| | Cefazolin | R |
| | Cefoxitin | R |
| | Ceftazidime | R |
| | Ceftriaxone | R |
| | Cefepime | R |
| Carbapenems | Doripenem | Not tested |
| | Meropenem | R |
| | Ertapenem | R |
| | Imipenem | R |
| Aminoglycosides | Amikacin | R |
| | Gentamicin | R |
| | Tobramycin | R |
| Other | Aztreonam | R |

Figure 3A:
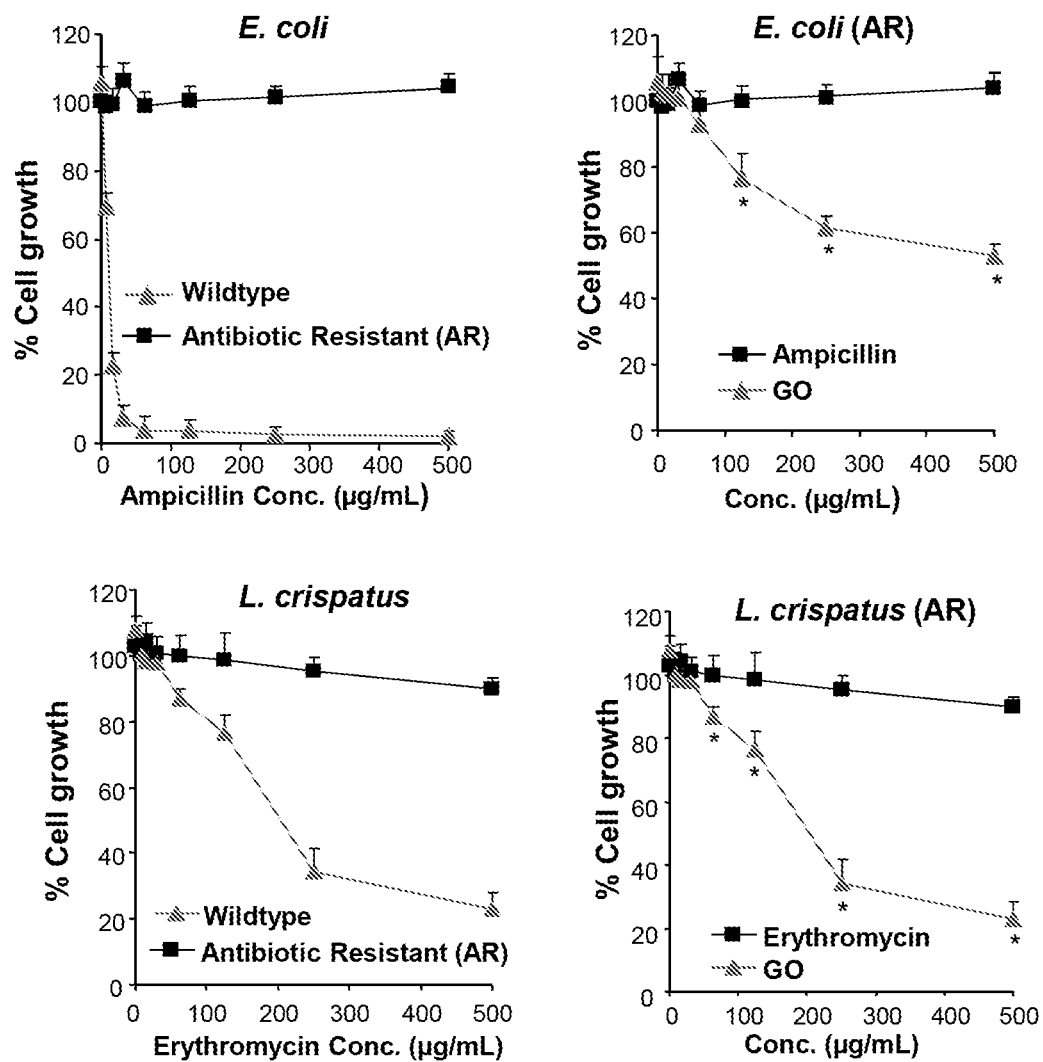
FIGS. 3A-3C show the bactericidal effects of the GO library.
Figure 10:
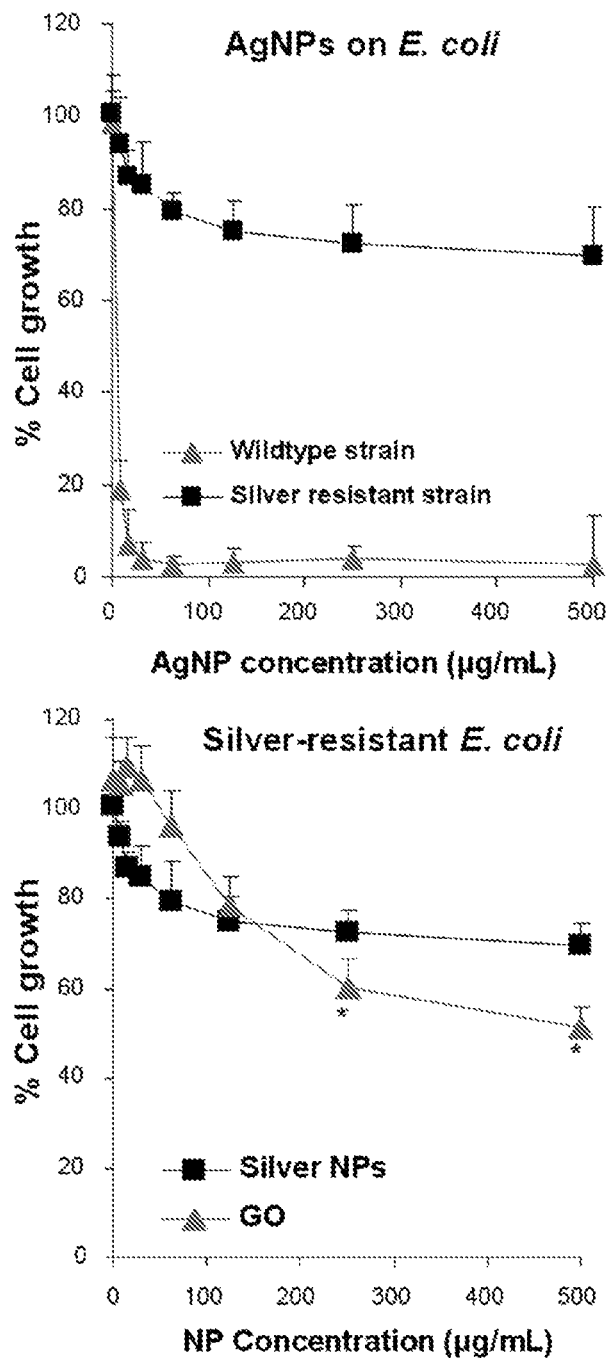
FIG. 10 shows a comparison of killing effects of Ag and GO NPs on wildtype and silver-resistant bacteria. The killing effects of GO and 20 nm silver nanoparticles were evaluated by comparing the cell growth in wildtype and silver-resistant strains after exposure to 0-500 µg/mL nanoparticle suspensions at 37° C. for 24 h.

This is demonstrated by the fact that ampicillin could induce effective killing with an $IC_{50}$ of 10 μg/mL in wildtype E. coli, while the resistant strain showed no growth inhibition, even at a dose as high as 500 μg/mL (FIG. 3A). In contrast, GO showed moderate antibacterial effects in wildtype and AR E. coli, yielding an $IC_{50}$ of 500 μg/mL. Similar results were found in AR L. crispatus strain (77% killing at 500 μg/mL), as well as in silver-resistant E. coli (FIG. 10).

Figure 3B:
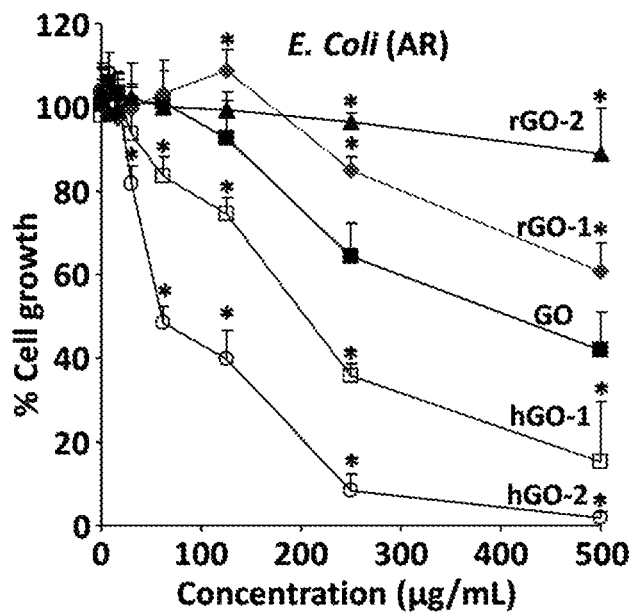
Figure 3C:
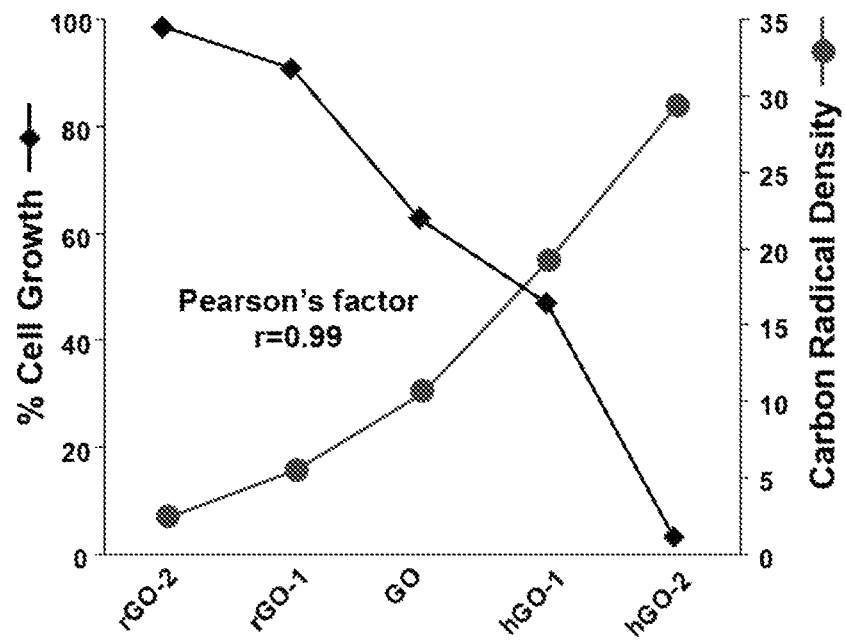

Since GO only exerts partial antibacterial effects, it would be desirable to improve the killing efficiency. This prompted us to look at the antibacterial effects of the GO library. We found that hGO sheets have significantly enhanced antibacterial effects compared to pristine GO, with hGO-2 achieving almost 100% killing at 500 µg/mL (FIG. 3B). In contrast, rGO-1 and rGO-2 showed decreased bactericidal effects compared to the pristine material. Comparison of the antibacterial efficiency with the physicochemical characteristics of the library materials (including oxidized chemical content, .C density, sheet size and zeta potential), showed the strongest correlation (r=0.99) to .C density (FIG. 3C). However, as expected, the correlation coefficient to the hydroxyl content was also strong (r=0.94) in light of the intimate relationship with the .C content. These results demonstrate the important role of .C in GO-induced antibacterial effects in AR bacterial strains.

GO-Induced Bactericidal Effects Involve Membrane Binding and Lipid Peroxidation

Figure 4:
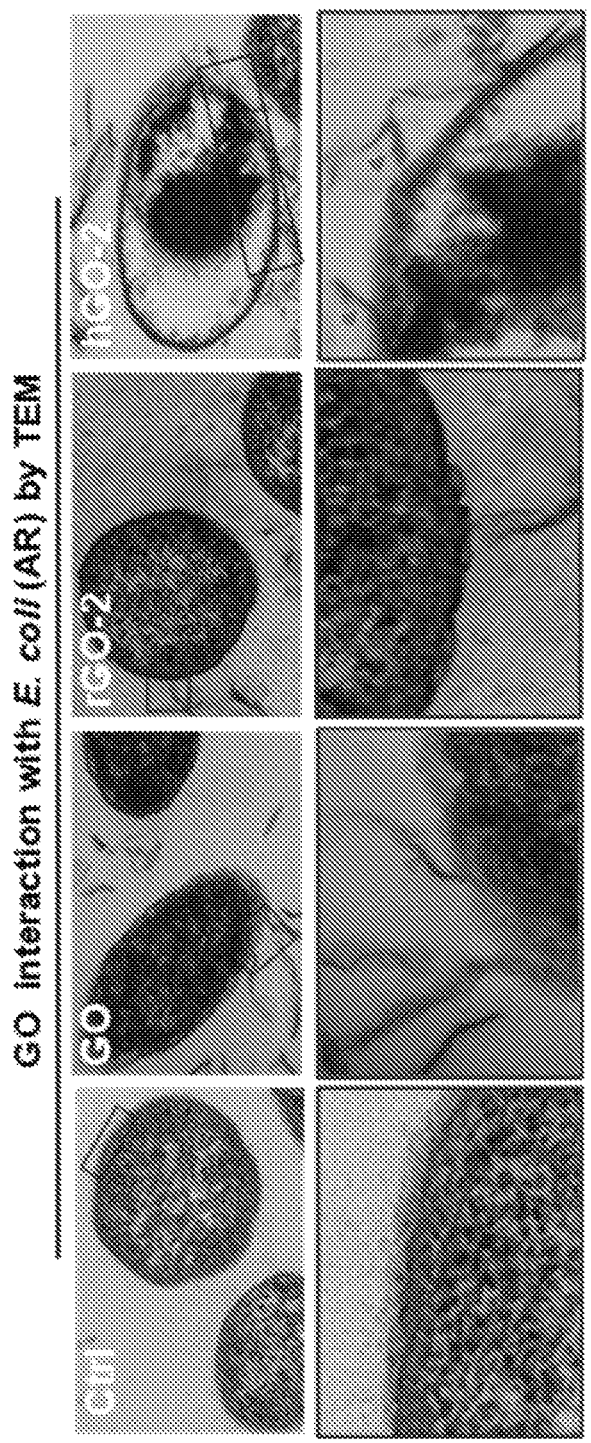
FIG. 4 shows TEM images showing the interaction between GO samples and AR *E. coli*. Cells were treated with 125 µg/mL of each of the GO samples for 24 h, then washed, embedded in resin, and negatively stained before TEM imaging. Arrows show the rGO-2, GO or hGO-2 nanosheets interacting with bacteria membrane.
Figure 11:
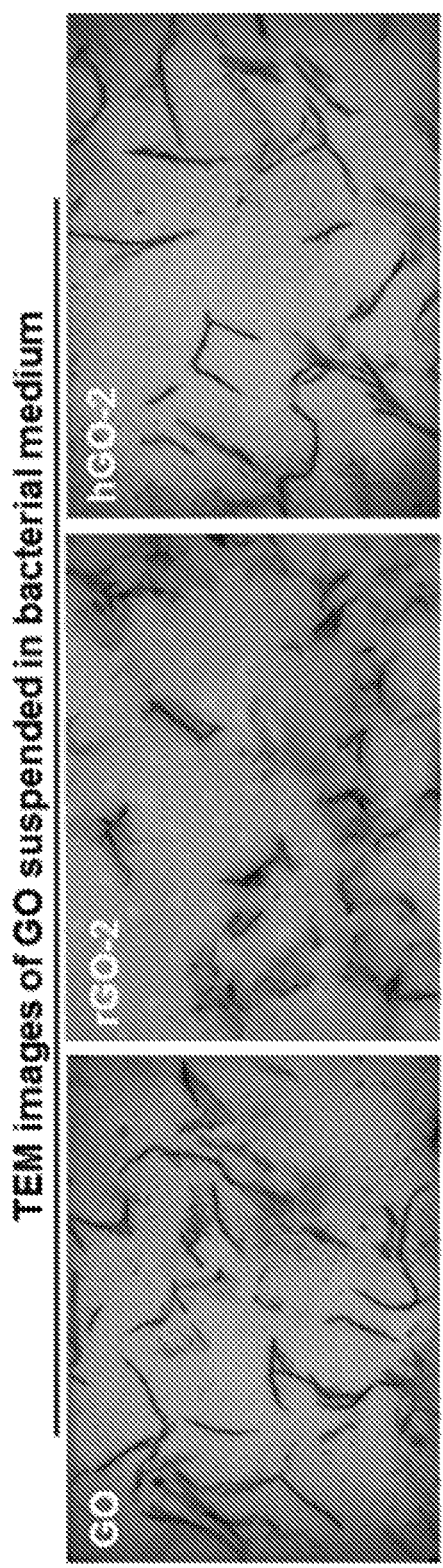
FIG. 11 illustrates the determination of GO morphology and dispersion state in bacteria culture media by TEM. GO nanoparticles were dispersed in LB broth (125 g/mL) without bacteria and incubated at 37° C. for 24 h. After centrifugation at 15,000 rpm for 5 min, the GO pellets were washed, embedded in resin, and negatively stained before being imaged by TEM.

It has been shown that the hydrophobic planar properties and hydrophilic edges of GO sheets allow membrane insertion, which could be related to their bactericidal effects (Kim et al. (2010) *J. Am. Chem. Soc.* 132(23): 8180-8186). In order to obtain ultrastructural resolution of the interaction of our library materials with the AR *E. coli* strain, TEM analysis was performed after bacterial exposure in culture medium for 24 h. Due to the low electron densities of GO, the suspended GO sheets could only be visualized when vertically positioned on the grid but not when they aligned with the flat surfaces parallel to the grid (FIG. 11). This is consistent with other reports (Tu et al. (2013) *Nat. Nanotechnol.* 8(8): 594-601). Following bacterial co-culture, the TEM images revealed that the GO nanosheets associate with the bacterial membrane without clear evidence of piercing or cutting of the bacterial membrane (FIG. 4); this is consistent with the observations of Tu et a. (Id.). We also observed that while the pristine and reduced (rGO-2) sheets may associate with the membrane without any visible damage, AR *E. coli* treated with hGO-2 display extensive structural damage, as manifested by membrane collapse.

Figure 5A:
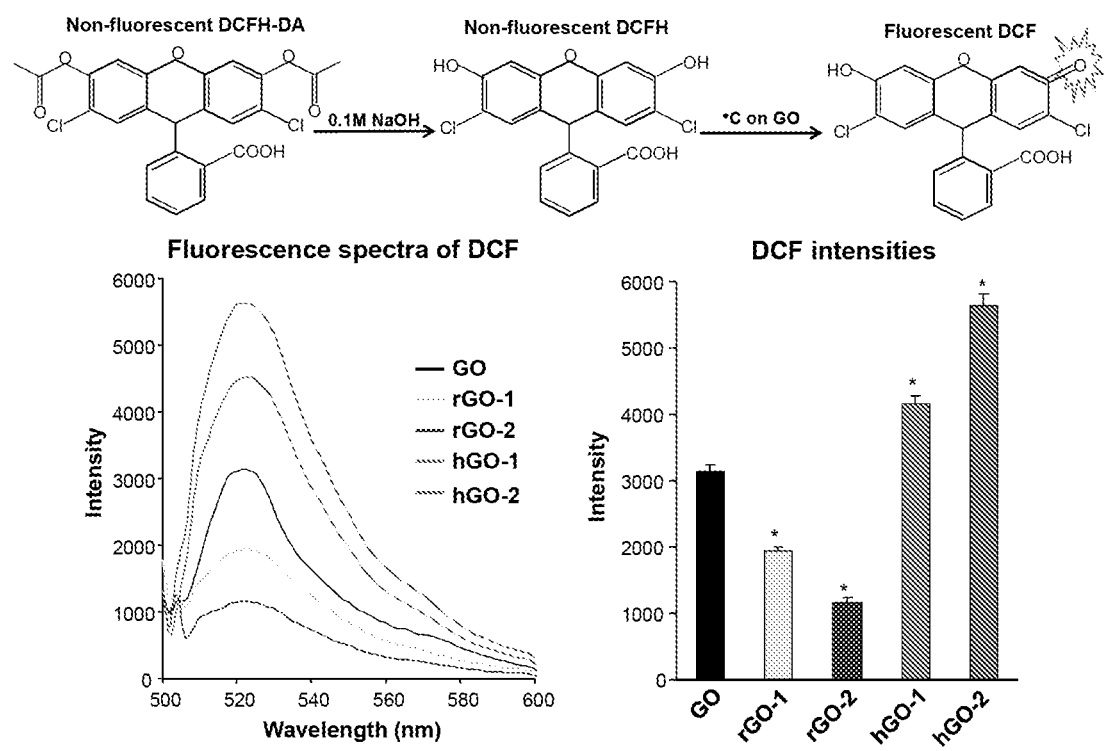
FIG. 5A-5E show that the mechanism of GO bacterial killing involves membrane association, lipid peroxidation and membrane damage.
Figure 12:
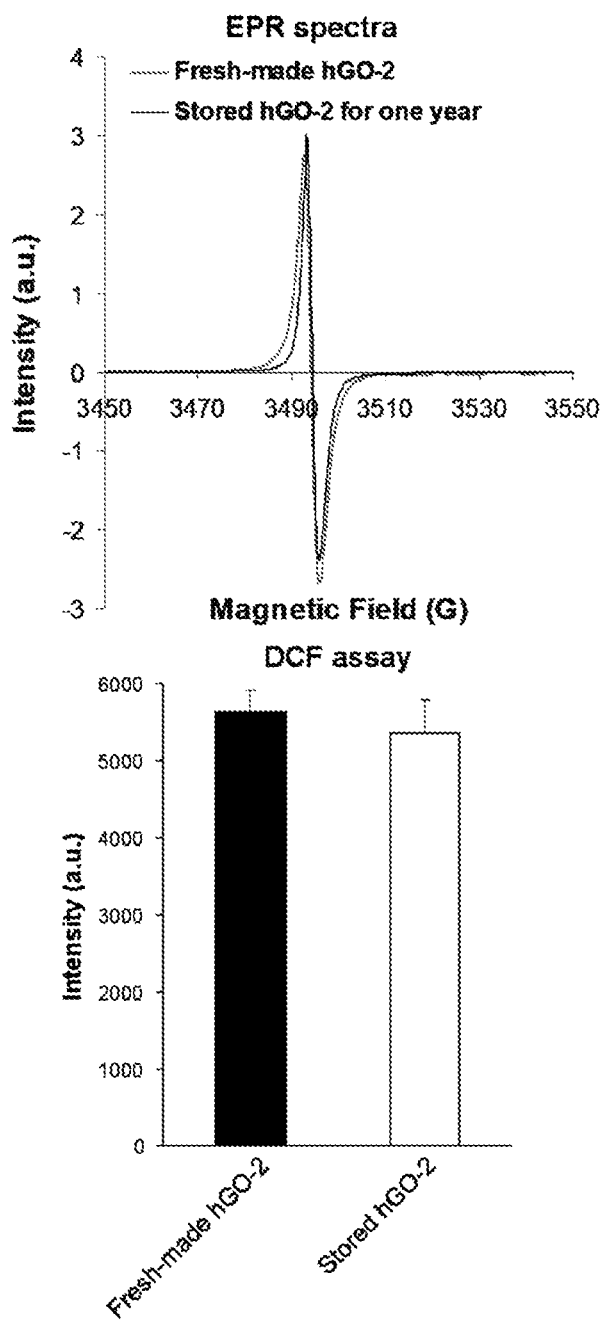
FIG. 12 shows the durability test of carbon radicals on hGO-2. Comparison of fresh-made and stored hGO-2 (in DI water at 4° C. for one year) was performed to evaluate the stability of carbon radicals by EPR test (top panel) and their oxidative capability by DCF assay (bottom panel).

.C radicals are typically considered more active than other surface functional groups because they contain unpaired electrons that lead to pro-oxidative potential (Yang et al. (2014) *Angew. Chem.-Int. Edit.* 53(38): 10109-10113). The pro-oxidative capacity of the GO library was examined by 2', 7'-dichlorodihydrofluorescein ($H_2DCF$), which can be converted to a fluorescent 2', 7'-dichlorofluorescein (DCF) derivative by a variety of oxidizing radicals generated by nanomaterials or small molecules (Zhang et al. (2012) *J. Am. Chem. Soc.* 134(38): 15790-15804; Yeum et al. (2003) *J. Nutr.* 133(8): 2688-2691; Wrona et al. (2008) *Free Radic. Biol. Med.*, 44(1): 56-62). As shown in FIG. 5A, compared to pristine GO, hGO materials induced a significant increase in DCF fluorescence, while the reactivity of the rGO materials were low. Thus, the overall ranking of the abiotic oxidative potential of the GO samples was hGO-2>hGO-1>GO>rGO-1>rGO-2, which correlates well with the .C densities (r>0.97). hGO-2 was also used to evaluate the stability of the carbon radicals on the material surface, using serial EPR measurements. This demonstrated limited change in the EPR peak intensity and pro-oxidative capability for hGO-2 samples stored in deionized water at 4° C. for 1 year (FIG. 12). However, the carbon radical existence on GO samples in biological media will likely be of short duration due to the presence of abundant reductive molecules.

Figure 5B:
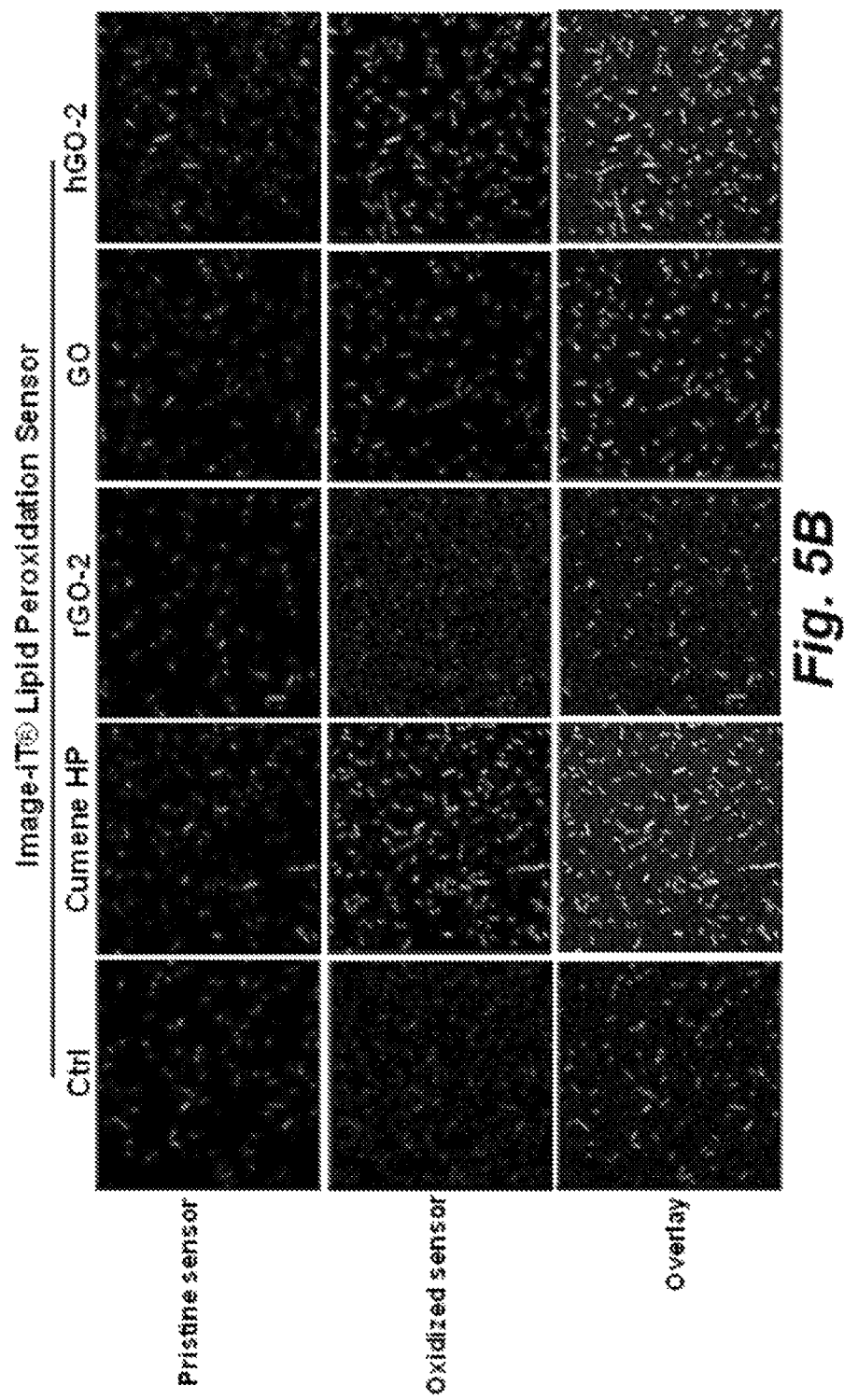
Figure 5C:
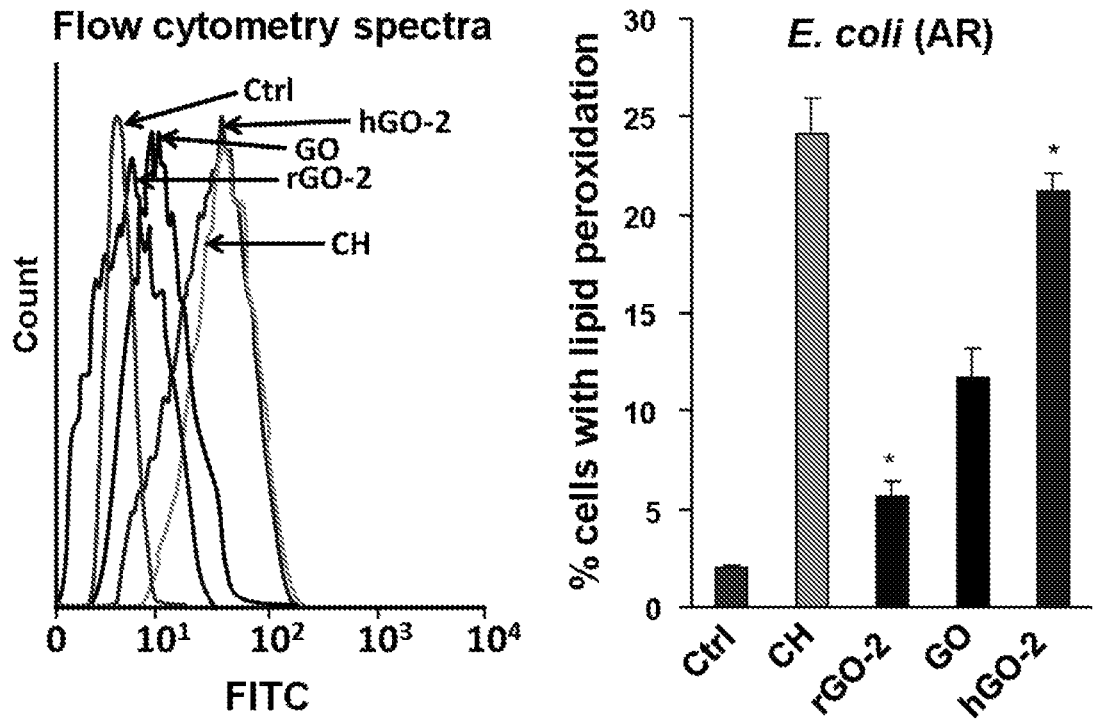
Figure 5D:
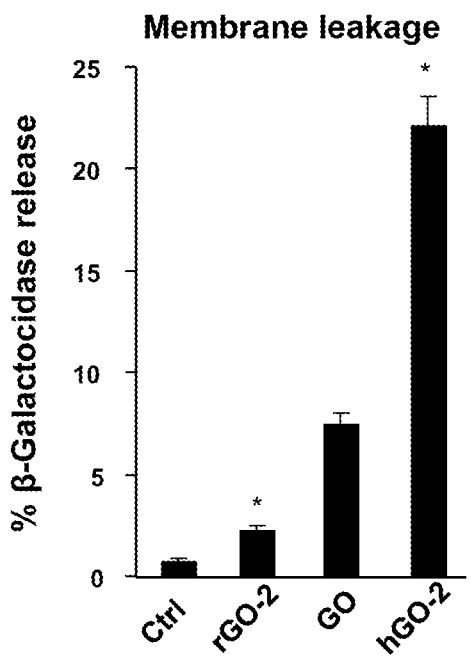
Figure 5E:
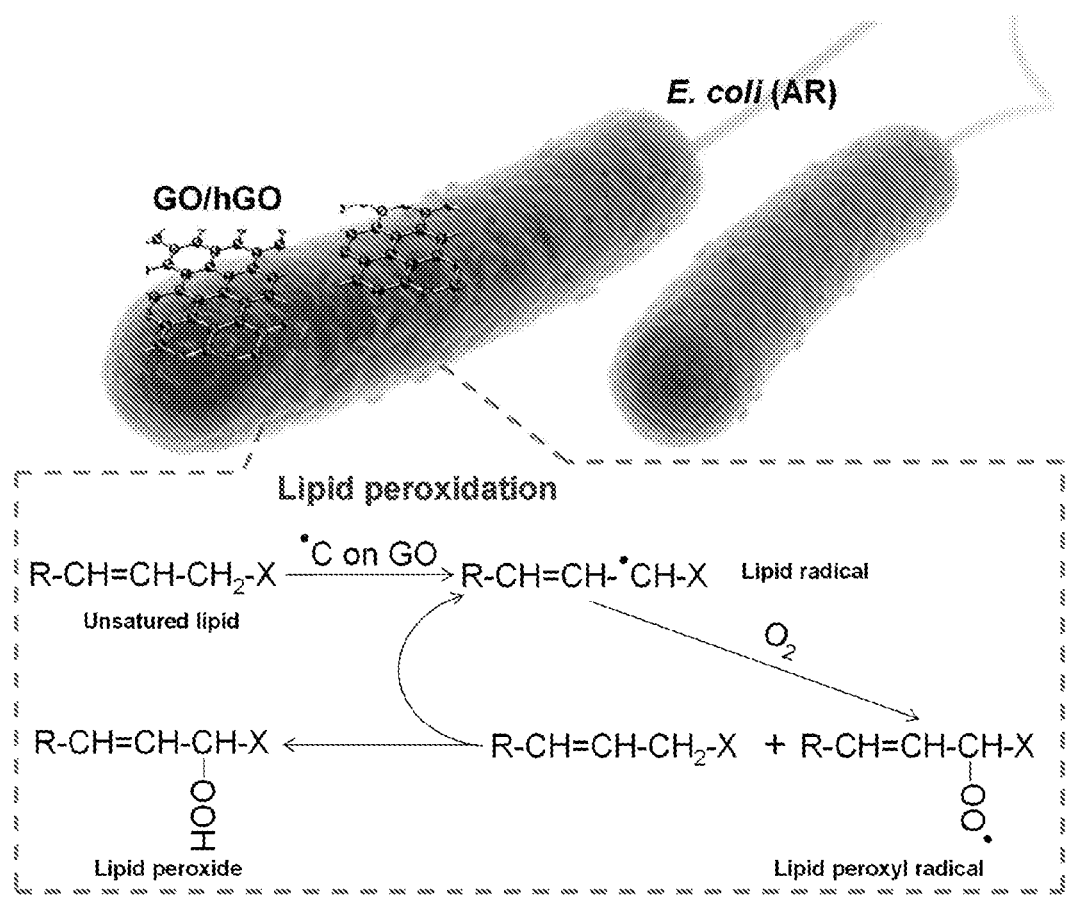

To further demonstrate how the pro-oxidative effects under abiotic conditions may relate to membrane injury by hGO-2, a BODIPY® 581/591 C11 reagent was used to study lipid peroxidation in *E. coli*. The reagent shows a shift in peak fluorescence emission from red (~590 nm) to green (~510 nm) during lipid peroxidation, as demonstrated by using cumene hydroperoxide (CH) as a positive control (FIG. 5B). hGO-2 induced prominent lipid peroxidation compared to pristine GO, while rGO-2 had minimal effects. These results were also quantitatively expressed by studying lipid peroxidation with flow cytometry, which showed that pristine GO induced lipid peroxidation in 12% of bacterial cells, while the comparable values for hGO-2 and rGO-2 were 21% and 5%, respectively (FIG. 5C). Since lipid peroxidation could destabilize the bacterial membrane, we studied β-galactosidase release from AR *E. coli* after GO treatment. We found that hGO-2 can induce 22% β-galactosidase release from membrane-damaged bacteria (FIG. 5D), which is significantly higher than GO (8%) or rGO (3%). In summary, these data demonstrate that the bactericidal effects of GO are dependent on interactions with the bacterial membrane, where surface reactive groups such as the .C could lead to membrane damage and cell death as a result of lipid peroxidation. FIG. 5E shows the mechanism for the induction of lipid peroxidation as a result of the .C on the GO surface interacting with unsaturated lipids in the bacterial membrane. We propose the involvement of three steps, namely: (i) electron transfer from the .C to one of the C atoms adjacent to double bonds in the lipid; (ii) electron transfer from this functionalized C atom to bystander molecular dioxygen ($O_2$), leading to the formation of a lipid peroxide radical, containing the attached-O—O group; (iii) generation of a lipid peroxide from the lipid peroxide radical.

Highly Efficient Killing of AR Bacteria by hGO-2 Films.

Figure 6A:
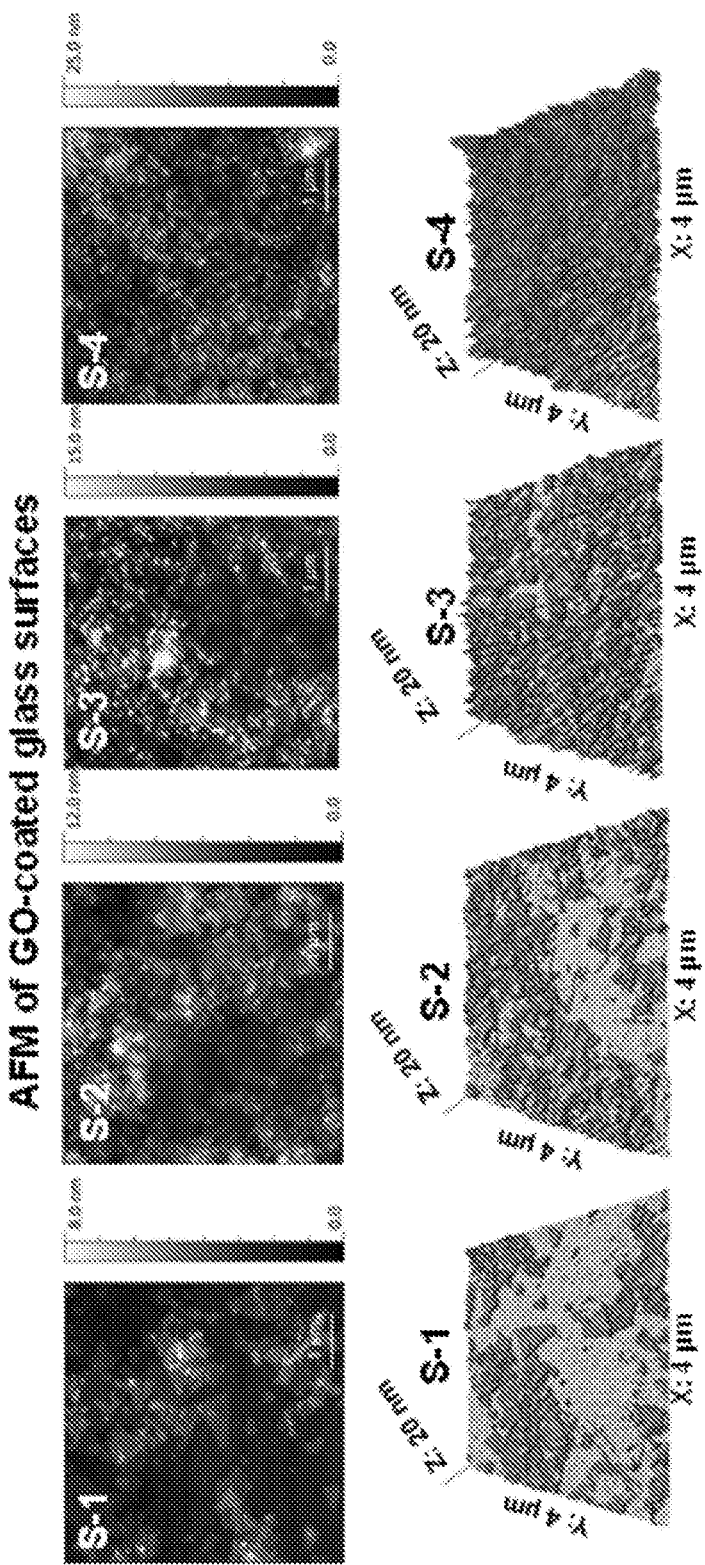
FIGS. 6A-6D illustrate inhibition of AR bacteria growth by non-covalently coated hGO-2 films on a glass substrate.
Figure 13:
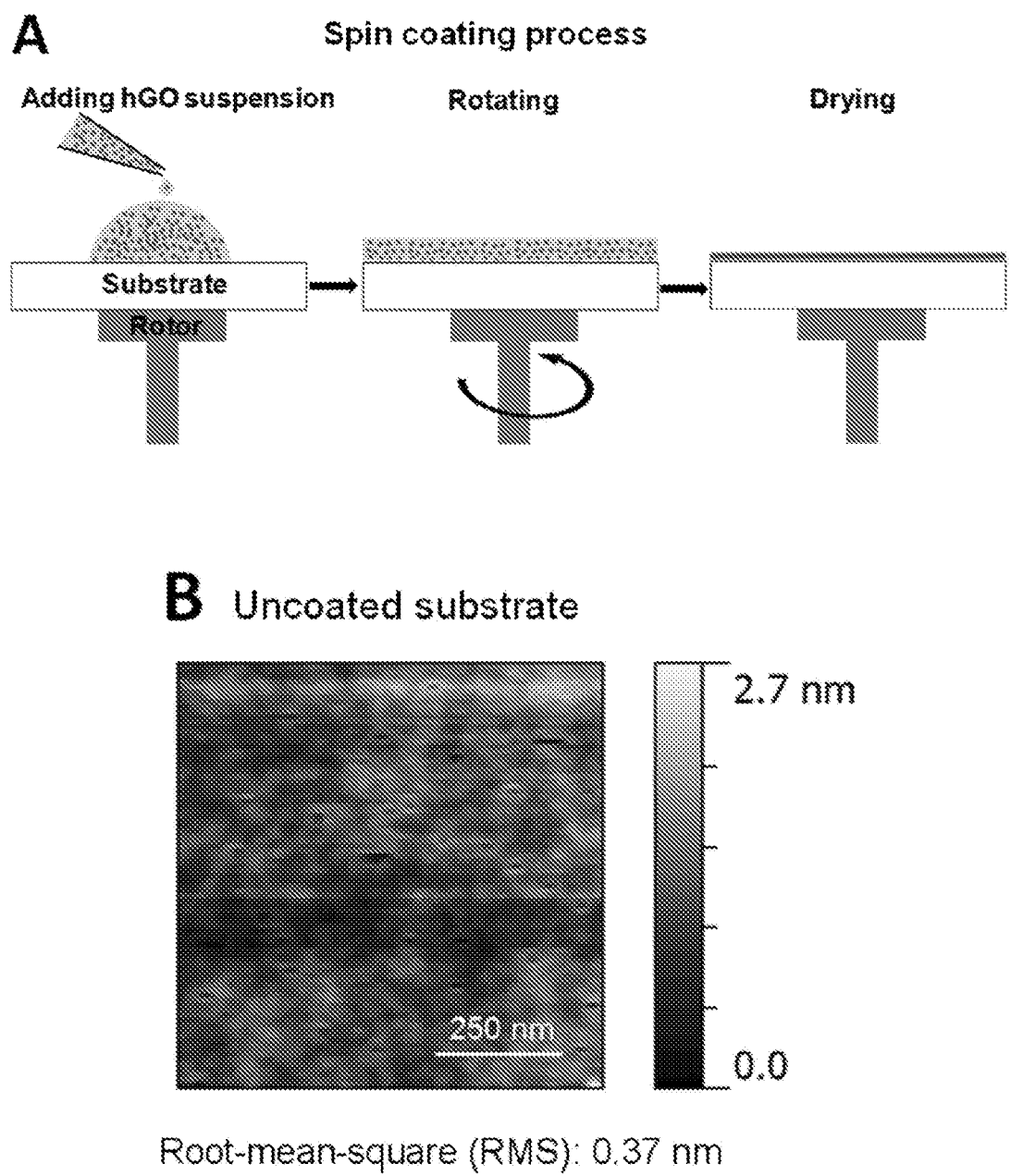
FIG. 13, panels A-B, illustrates the spin coating process and shows an AFM image of uncoated substrate. Panel A) Scheme of spin coating process, and Panel B) AFM image of uncoated glass substrate with surface roughness factor, RMS at 0.35 nm. Spin coating of hGO-2 on glass substrates involves adding of hGO-2 suspensions onto spinning surface and a drying process to generate a series of GO-coated substrates (S1, S2, S3 and S4) with different percentages of surface coverage and thickness. hGO-2 coatings were formed on 18 mm×18 mm×0.15 mm glass substrates using a Laurell WS-650Sz spin coater. 2 mg/mL of GO suspensions were added onto the spinning substrate surfaces (1000 rpm) using a pipette until the desired thickness was obtained.
Figure 14:
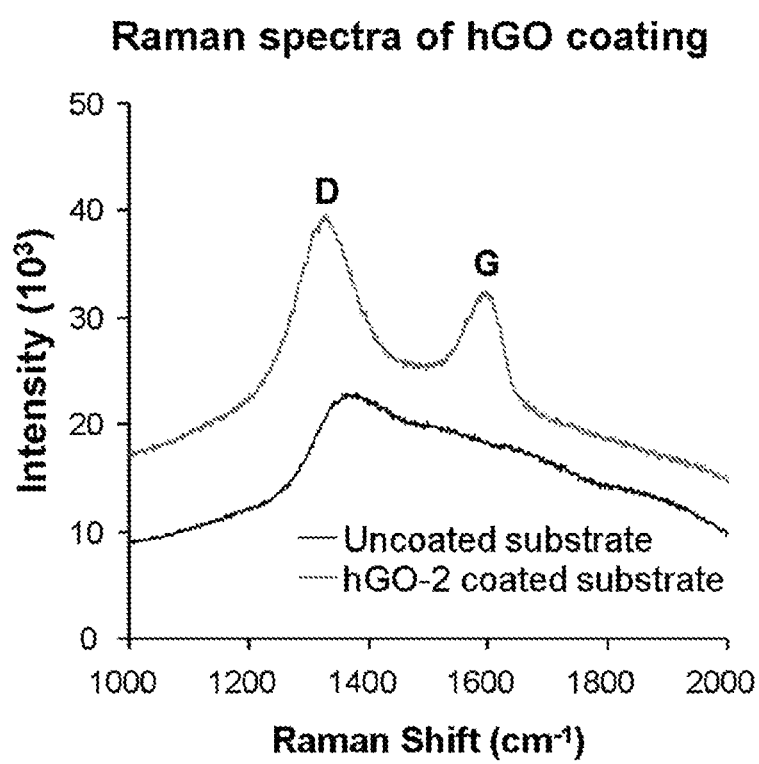
FIG. 14 illustrates the characterization of hGO-2 coatings on glass substrates by Raman spectroscopy. hGO-2 coated substrates were characterized using Raman spectroscopy (Renishaw inVia Reflex, Wotton under Edge, UK) with a 785 nm near-infrared diode in the wavenumber region 1000-2000 cm−1. Uncoated glass substrate was used as a control.

Because GO is often incorporated into composites (e.g., bandages and biofilms) for antibacterial activity, we were interested to see whether immobilization of hGO to material surfaces could attain significant bactericidal effects. We performed proof-of-principle testing by depositing hGO-2 thin films on a glass substrate or covalently bonding the hGO to the surfaces of silicone catheters. hGO-2 nanosheets were attached to the surface of a glass substrate by spin coating, allowing us to prepare a series of coated substrates with controllable GO film thickness (7-25 nm) and surface coverage. Four glass substrates (S-1 to S-4) coated with hGO-2 films (FIG. 13A) were characterized through the use of AFM (FIG. 6A, 13B) and Raman spectroscopy (FIG. 14). The Raman spectra demonstrated the presence of signature D and G bands that are characteristic of GO, and the AFM images confirmed the varying thickness of these films, which varied from 7 nm to 25 nm. Moreover, AFM showed that hGO-2 coating exhibited interesting stacking behavior with larger sheets attaching to the substrate with their flat sides facing up, while smaller sheets were stacked on top of the larger sheets. The surface area coverage varied from 50% in S-1 to 100% in S-4.

Figure 6B:
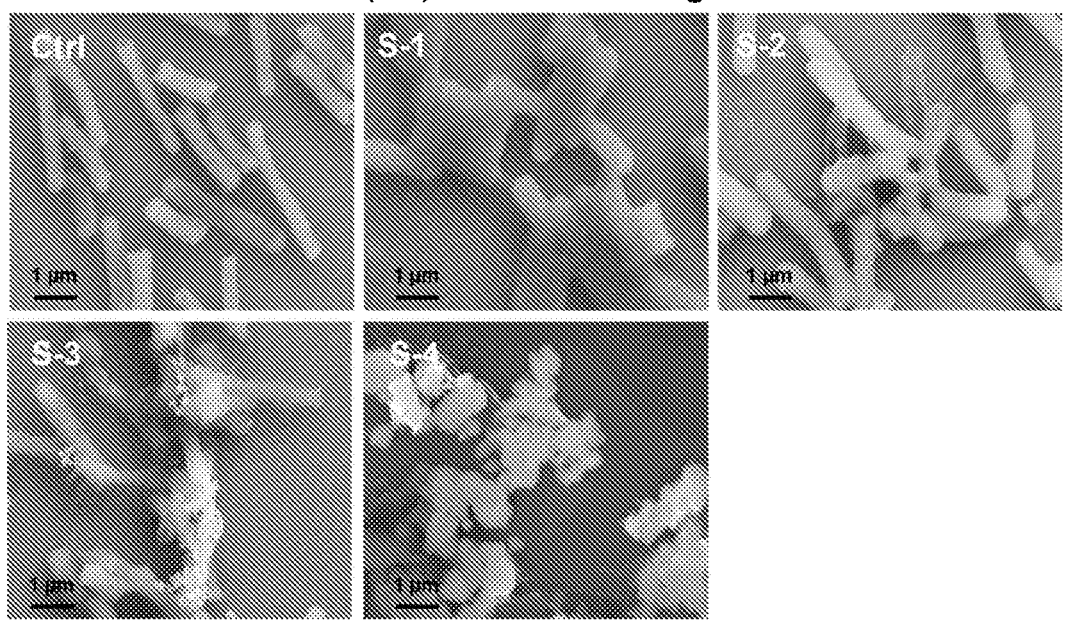
Figure 6C:
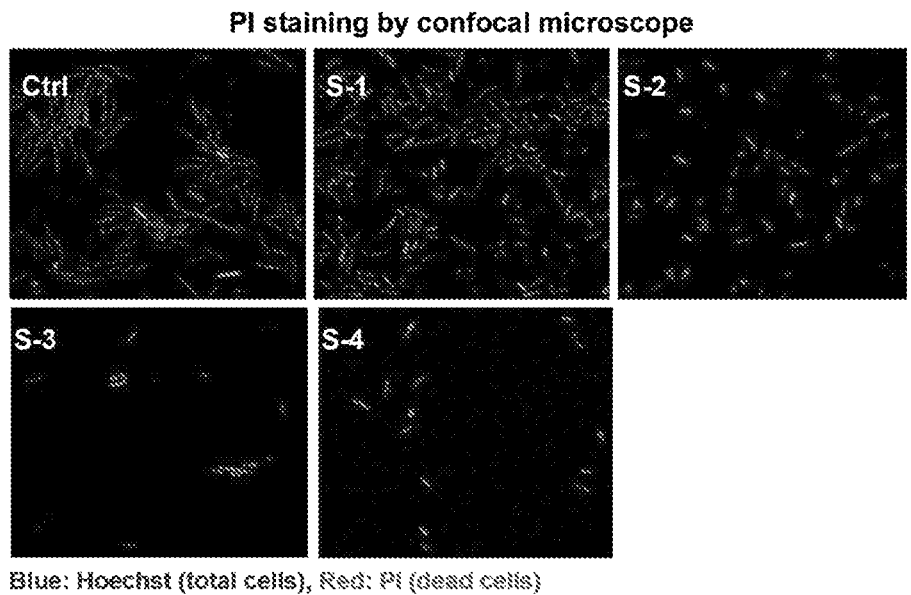
Figure 6D:
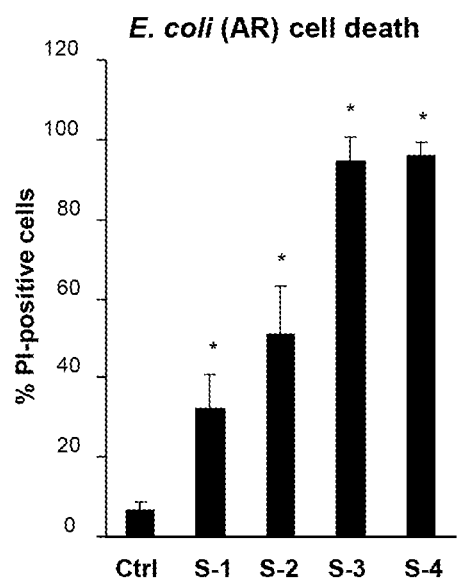

Testing of the antibacterial effects of the coated glass surfaces was carried out by incubating S-1 through S-4 with the AR *E. coli* strain for 6 h at 37° C. The bacterial morphology and viability were subsequently assessed by scanning electron microscopy (SEM) and propidium iodide (PI) staining, respectively. Instead of the rod-shaped appearance and intact surfaces found on non-exposed bacteria, SEM demonstrated an incremental increase in bacterial membrane damage and fragmentation during exposure to the incremental stacking density in S-1 to S-4 (FIG. 6B). Assessment of the bacterial viability by PI staining and confocal microscopy showed that while there were <10% PI-positive bacteria grown on the uncoated glass surface, there was a gradual increase in the presence of dead cells with incremental levels of coating, such that 96% of bacterial cells were non-viable in the presence of S-3 and S-4. It is also noteworthy that the killing effects of the hGO-2 films were more effective than that of the hGO-2 suspensions, suggesting that a coated film format may be superior for antibacterial applications.

Figure 7A:
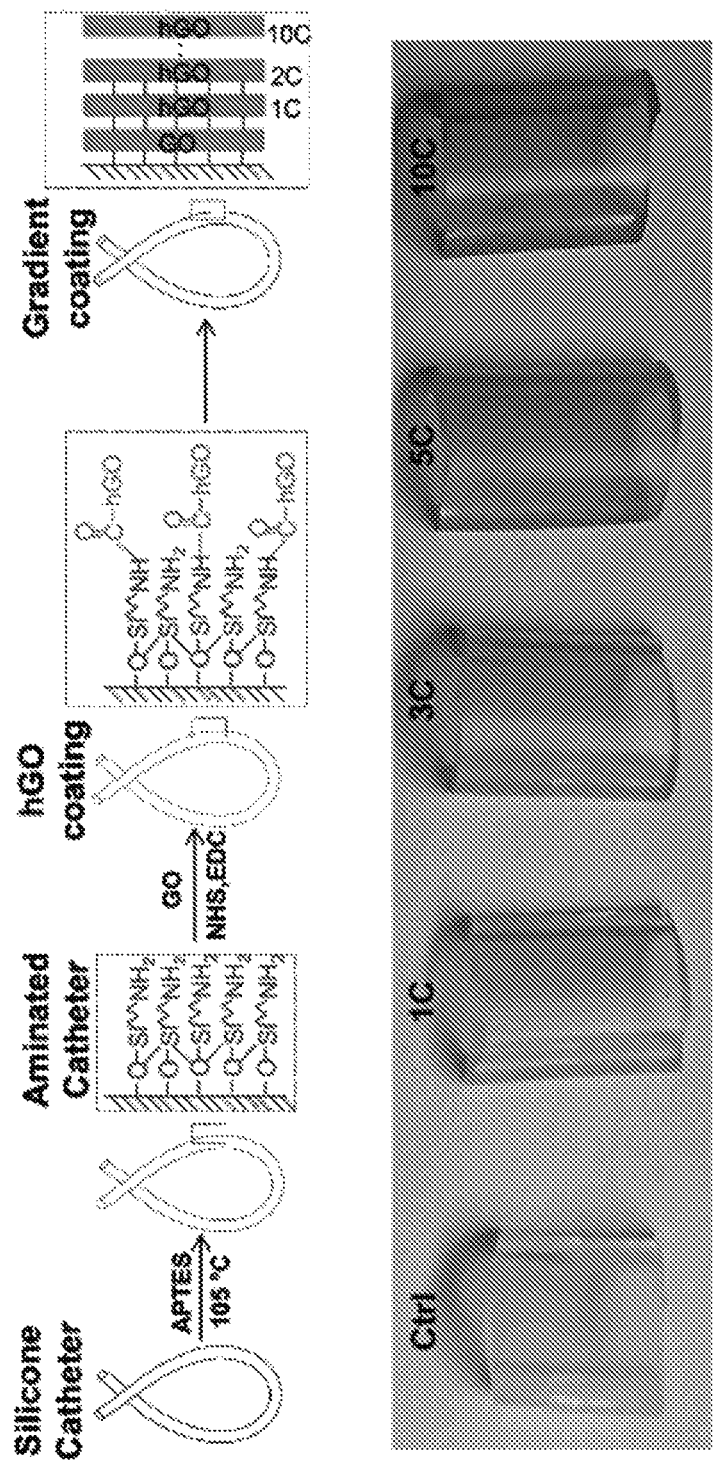
FIGS. 7A-7D illustrate inhibition of AR bacterial growth by hGO-2 covalently attached to the surface of a silicone catheter.
Figure 7B:
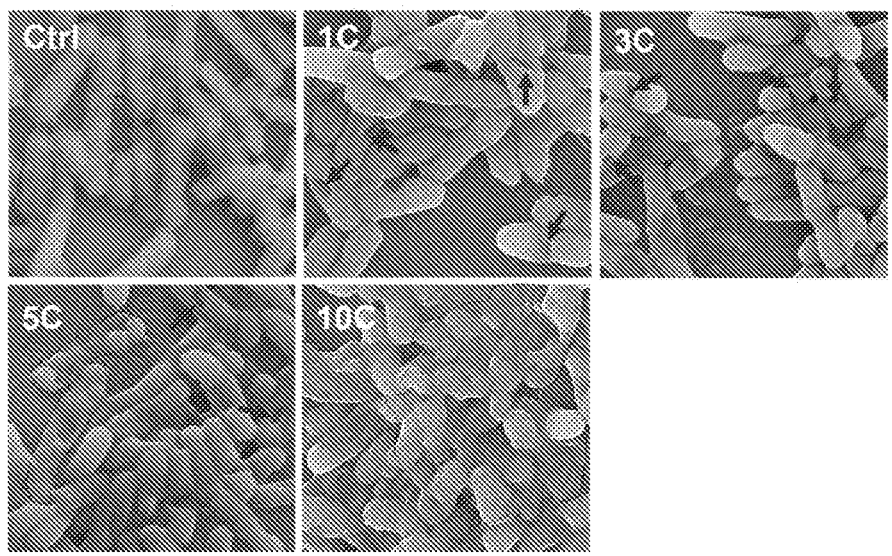
Figure 7C:
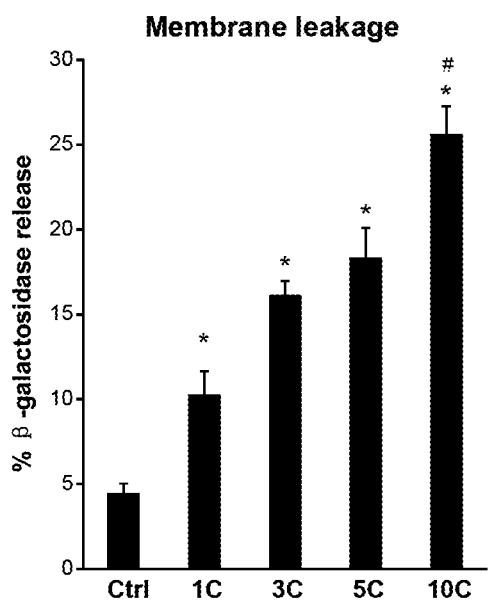
Figure 7D:
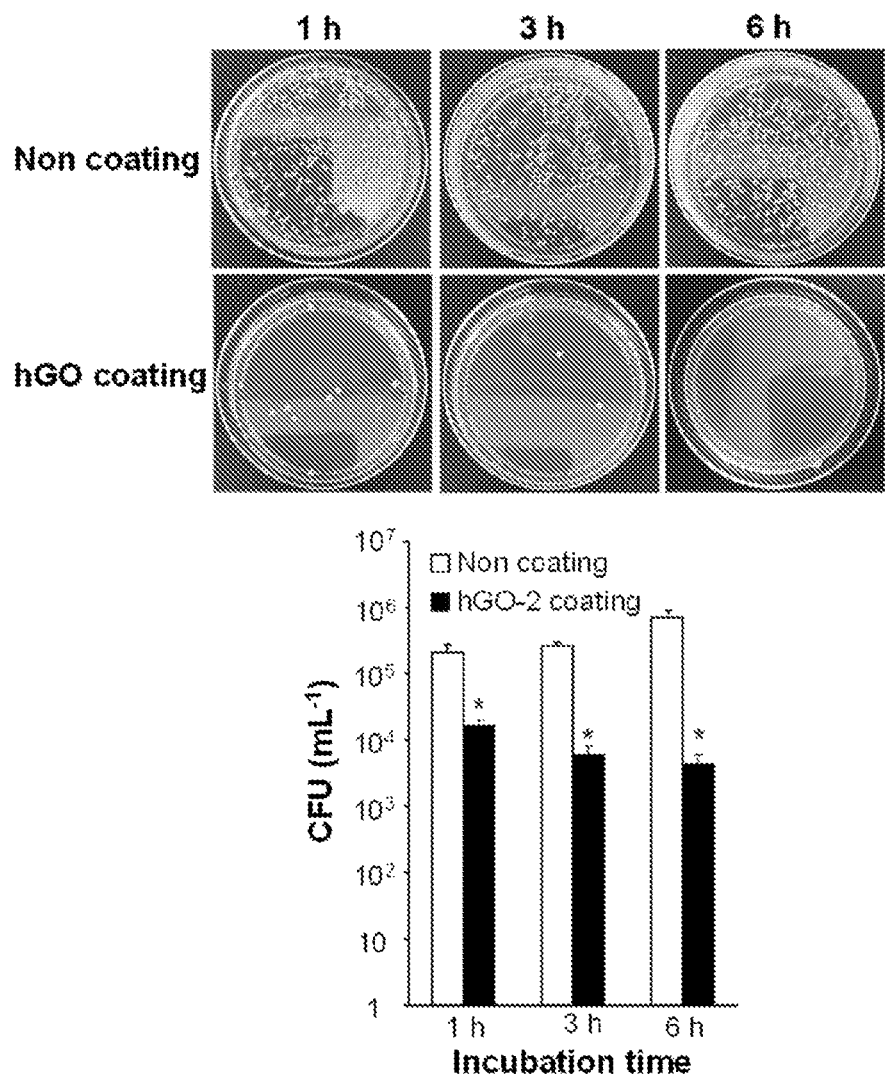
Figure 15:
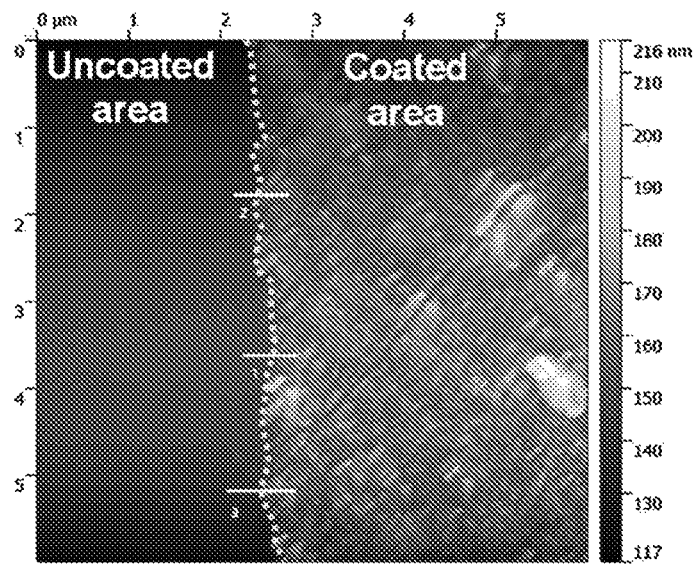
FIG. 15 illustrates AFM and Raman analysis of covalently coated hGO-2 films on a silicon wafer. AFM was used to measure the film thickness of coated and uncoated areas on a silicon wafer. It shows the 16 nm height of the hGO-2 film after 10 cycle coating. hGO-2 coated silicon wafer showed typical G and D bands in their Raman spectra while any the uncoated area shows no signal.
Figure 15:
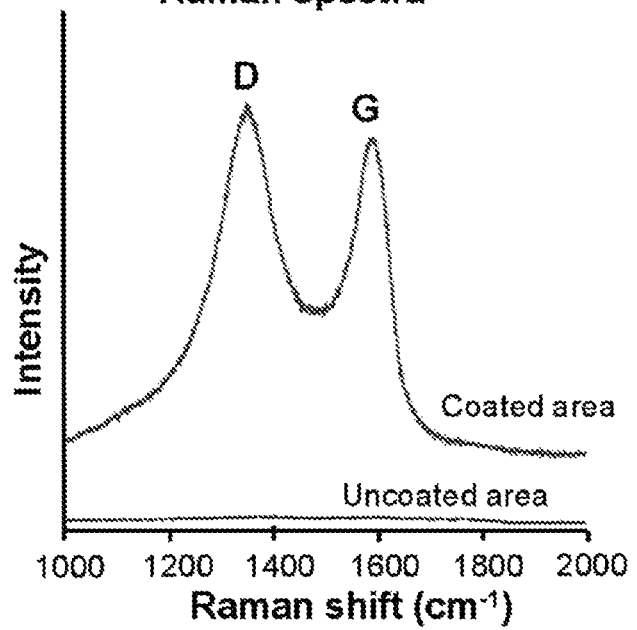
Figure 16:
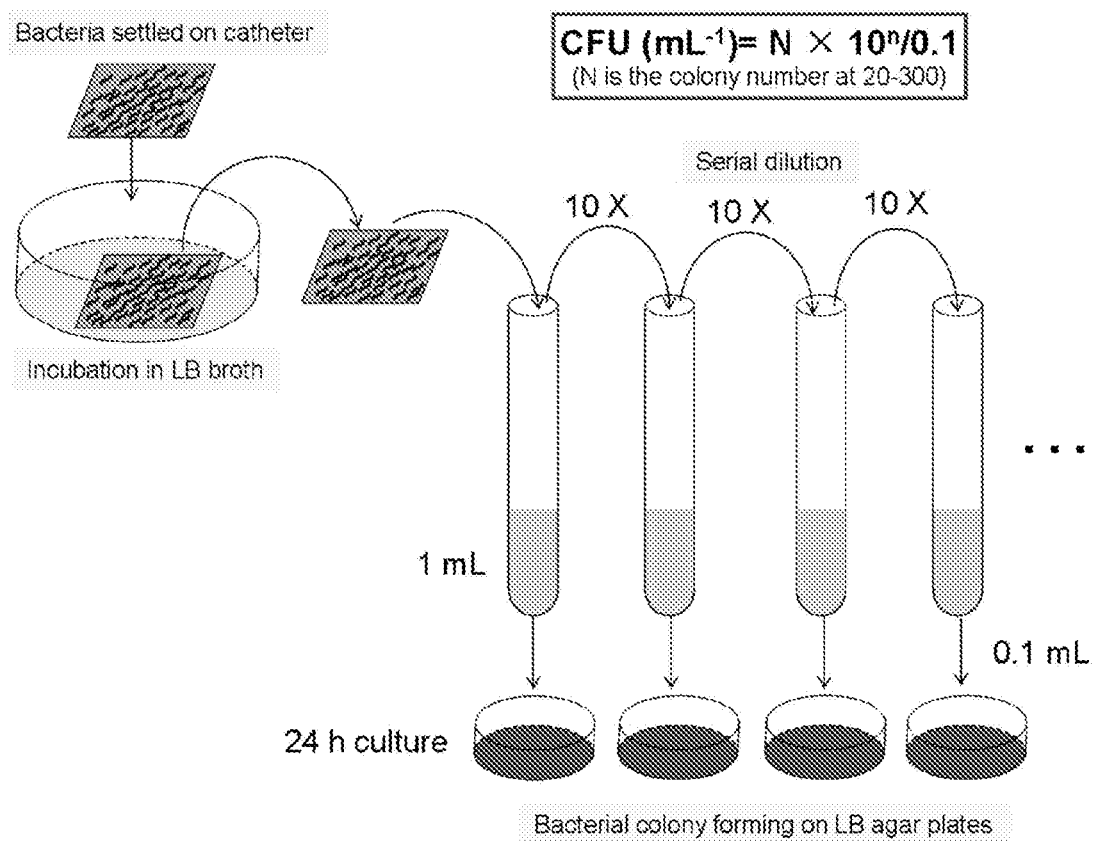
FIG. 16 schematically illustrates a CFU assay. The entire process includes introduction of bacteria on catheter surface, incubation of bacteria settled on catheters, collection of bacteria from catheter surfaces, serially dilution of bacteria, spreading diluted bacterial solution over LB agar plates and examining bacterial colonies after 24 h incubation.

The next proof-of-concept testing was covalent attachment of hGO-2 to the surface of a silicone catheter, which has relevance from the perspective of bacterial contamination of indwelling clinically used devices (Jacobsen et al. (2008) Clin. Microbiol. Rev. 21(1): 26-59). A method was developed to prepare the substrate surface for coating, namely surface amination by (3-Aminopropyl)triethoxysilane (APTES), followed by conjugation of the amine groups with hGO-2 (FIG. 7A). These coatings showed extraordinary durability and could stably attach to the catheter surface, even after sonication and washing procedures. This concept was initially tested on a silicon wafer, where the coating could be confirmed by the signature G and D bands in the Raman spectra that were obtained, as well as the presence of a 16 nm thick layer by AFM after 10 cycles of coating (FIG. 15). The procedure was then repeated on a series of silicone catheters that were coated with hGO-2 for 1, 3, 5 and 10 cycles (denoted as 1C, 3C, 5C and 10C). Each layer of coating resulted in progressive darkening of the catheter surface. The antibacterial effects of the coated catheter surfaces were tested in situ by visualizing morphological changes in AR $E.\ coli$. As shown in FIG. 7B, while the bacteria incubated with uncoated catheter surfaces exhibited rod shaped cells with intact surfaces, holes appeared in the bacterial membrane during exposure to coated catheters. We also observed bacterial fragmentation during exposure to catheter surfaces coated 5 or 10 times. These results were confirmed in a β-galactosidase assay, which reflects progressive bacterial membrane leakage (FIG. 7C). We also performed a quantitative evaluation of the bactericidal effects of 10C hGO-2 coated catheter surface. As shown in FIG. 16, after 1, 3 and 6 h of incubation, the bacteria settling on the catheter surface were collected, serially diluted and introduced into LB agar plates to assess the number of colony forming units (CFU). The coated catheters showed a time-dependent reduction of CFU, compared to the uncoated catheters (FIG. 7D). A dramatic decrease of CFU could be seen after 1 h of exposure to the hGO-2 film, amounting to 2.2 log reduction after 6 h exposure. All considered, the above results show that hGO-2 coating of glass and catheter surfaces can be used to kill AR $E.\ coli$.

Discussion

In this study, we delineated the GO surface groups that are responsible for bactericidal effects and explored the potential use of GO coating on the surface of a medical device that may be contaminated by AR bacteria. We found that the .C density on the GO surface is most proximately associated the antibacterial effects of these materials compared to other functional groups. The efficacy of bacterial killing could be enhanced by a novel hydration process of the GO surface that opens the epoxy rings to generate more surface .C groups, without impacting superoxide or hydroxyl radical generation. The high .C density enhanced the oxidative potential of hGO, which allowed these sheets to induce lipid peroxidation of the bacterial membrane with significantly higher bactericidal effects in AR strains. In contrast, surface reduction decreases .C density and antibacterial killing by GO. Coating of hGO on glass and silicone catheter surfaces allows effective killing of AR $E.\ coli$ and may be useful for preventing biofilm formation on catheter surfaces.

The most important finding of this study is the demonstration that among the surface reactive groups, .C radicals appear to play an important role in shaping the antibacterial activity of GO. The .C radicals are generated during breaking of the C=C bonds when graphite is treated with strong oxidants to prepare GO. We found that alkaline hydration could increase the .C density during hydrolysis of the epoxy groups on the GO surface. The formation of this radical group was reported to be an intermediary step during occupancy of the p orbitals by single electrons (Khimiya, Chemical Properties of Ethylene Oxide. In $Ethylene\ Oxide$, Zimakov, P. V.; Dyment, O. H., Eds. 1967; pp 57-85). While isolated .C radicals are often unstable in association with a small molecule, the single carbon electrons on the GO surface are located in the π-network plane, allowing them to conjugate with the π electrons of neighboring double bonds to form π-conjugated $.C^{14}$ which are more stable. Moreover, the mobility of .C among the conjugated C=C bonds could significantly enhance its oxidizing capability and reactivity with target molecules (e.g., membrane lipids), coming into contact with the basal GO plane. This allows hGO-2, which has the highest .C density, to exert the highest bactericidal effects, in contrast to rGO that exhibits a low .C density and lack of bactericidal effects. The same characteristics are involved in the effective bactericidal effects of hGO when coated on the surfaces of catheters or a glass substrate.

Multidrug resistance in a growing number of infectious agents is considered as one of the greatest threats to human health in a recent World Health Organization report (Antimicrobial Resistance: Global Report on Surveillance //apps.who.int/iris/bitstream/10665/112642/1/ 9789241564748_eng.pdf). For example, fluoroquinolone-resistant $Shigella$ has caused more than 1 million deaths in 2012, while multidrug resistant $Mycobacterium\ Tuberculosis$ resulted in an estimated 170,000 deaths in the same timeframe. Moreover, bacterial antibiotic resistance now impacts most pharmaceutical antibacterial agents. Among the major pathways leading to antibiotic resistance are acquired mechanisms that block antibiotic access to intracellular targets, either through the reduction of membrane permeability (Kojima et al. (2013) Proc. Natl. Acad. Sci. USA, 110(28): E2629-E2634) or increased drug efflux by membrane pumps (Dolejska et al. (2013) J. Antimicrob. Chemother. 68(1): 34-39). Another resistance mechanism involves the mutation of antibiotic targets in bacteria (Gao et al. (2010) PLoS Pathog. 6(6): e1000944) or their modification (Katayama et al. (2000) Antimicrob. Agents Chemother. 44(6): 1549-1555) to prevent antibiotic binding. A third mechanism is the inactivation of antibiotics by enzymatic activities such as hydrolysis (Queenan et al. (2010) Antimicrob. Agents Chemother. 54(1): 565-569) or post-modification (Wright et al. (2005) Adv. Drug Deliv. Rev. 57(10): 1451-1470). In addition, these diverse resistance mechanisms often work synergistically to establish a formidable defense against antibiotics. In contrast, GO is capable of bacterial killing by anchoring to the membrane and inducing lipid peroxidation without the necessity of cellular uptake. This circumvents traditional AR mechanisms, with the ability to overcome antibiotic and even silver resistance pathways.

To take full advantage of the antibacterial effects of GO, we postulated that it is possible to enhance its 2D material effects through modification of its surface reactivity and immobilization on the surface of a medical device that can be colonized by AR bacteria. Indeed, GO has often been integrated into products such as antibacterial paper (Hu et al. (2010) ACS Nano, 4(7): 4317-4323), bandages (Sun et al.

(2014) *ACS Nano,* 8(6): 6202-6210) and ultrafiltration membranes (Yu et al. (2013) *J. Membr. Sci.* 447: 452-462). Another consideration is the reported toxicity of GO to mammalian cells and animals after intravenous, intraperitoneal, subcutaneous, or intramuscular injection (Seabra et al. (2014) *Chem. Res. Toxicol.* 27(2): 159-168; Ji (2016) *Sci. Bull.* 61(10): 755-771). Immobilized GO films on device surfaces would minimize direct exposure of GO to mammalian cells and thus reduce the potential toxicity. Herein, we report the preparation of hGO-2 films by noncovalent and covalent attachment to glass and catheter surfaces, respectively. Since silicone catheters are widely used in medical devices and serve as the substrate for bacterial biofilms[28], we explored stable, covalent attachment of hGO-2 that has potent antibacterial effects. hGO-2 also serves the same purpose if non-covalently attached to glass substrates. Both types of coatings are dependent on coating density and thickness for the efficacy of bacterial killing. This result could be attributed to two advantages of films over GO sheet suspensions: the first is enhanced binding to the bacterial surfaces and the second involves stronger exposure and shorter traveling distance for the reactive .C radicals on the hGO surface. In terms of the stability of spin coating versus covalent attachment of hGO-2 films on a glass substrate or silicon catheter surface, respectively, we do observe some differences. While spin coating can resist scratching or gentle washing, covalent attachment is more durable, capable of withstanding sonication for 30 minutes. There were also no observed differences between fresh-made and aged hGO-2 films in terms of the attachment stability over 6-months. In addition to the surface coating of medical devices, hGO-2 has the potential to be incorporated into bandages for wound healing, antibacterial additives in dental devices or water filtration membranes to prevent biofilm formation.

Conclusions

Our study indicates that .C plays a critical role in GO-induced bactericidal effects. Hydration of pristine GO generates a high .C density on the GO surface, which significantly enhances antibacterial effects, including in AR and silver-resistant bacteria. The mechanism of bacterial killing involves GO contact with the bacterial membrane without cellular uptake. The subsequent induction of lipid peroxidation in the bacterial membrane leads to a lethal effect. To explore the potential use of these structure-activity relationships for medical devices, hydrated GO with a high .C density was deposited onto the surfaces of glass substrates and silicone catheters, with the ability to kill AR *E. coli*. These results demonstrated the potential of GO with superior bacterial killing ability to be considered for their antibacterial effects in the clinical setting of antibiotic resistance.

Materials and Methods

Chemicals.

Ampicillin, N-Hydroxysuccinimide, Ethyl(dimethylaminopropyl) carbodiimide, 1-methyl-2-pyrrolidinone, erythromycin and $AgNO_3$ were purchased from Sigma-Aldrich (St. Louis, Mo., USA). The Beta-Glo® Assay System was purchased from Promega (Madison, Wis., USA); graphite flakes were provided by Asbury Graphite Mills; Hoechst 33342, Propidium iodide and Image-iT® Lipid Peroxidation Kit were purchased from Life Technologies (Grand Island, N.Y., USA).

Acquisition and Synthesis of a Surface Functionalized GO Library. GO Production:

GO was prepared using a modified Hummers method as described previously (Duch et al. (2011) *Nano Lett.* 11(12): 5201-5207). Briefly, graphite flakes (Asbury Mills 3061 grade) were oxidized and then filtered and centrifuged to remove any residual contaminants. The oxidized graphite was then re-dispersed in N-methyl-2-pyrrolidone (NMP, ACS reagent grade 328634, Sigma-Aldrich) and ultrasonicated using a Fisher Scientific Model 500 Sonic Dismembrator for 1 h at 50% power (~55 W) in an ice bath. The GO was then centrifuged using a Beckman Coulter J26-XPI at 5000 rpm for 10 min (~4,620 g). The top 80% of the supernatant was retained as the final GO sample for further processing of the reduced graphene oxide samples. The concentration of the GO solution was determined by optical absorbance at 330 nm.

Synthesis of Reduced GO:

GO was dispersed in NMP by ultrasonication for 1 h at 50% power (~55 W) as described before (Chowdhury et al. (2015) *Environ. Sci. Technol.,* 49(18): 10886-10893). The solution was heated to 150° C. with constant stirring in a silicone oil bath for 1 hour (rGO-1) or 5 h (rGO-2).

Preparation of Hydrated GO:

10 mL GO suspension (5 mg/mL) was diluted with 90 mL deionized (DI) water and mixed with 80 mg NaOH (0.02 M), using dispersal by a sonication probe (Sonics & Materials, USA) at 32 W for 10 min. The GO mixture was transferred into a round flask and refluxed at 50 or 100° C. in an oil bath with constant magnetic stirring for 24 h. 1 M HCl solutions were used to neutralize the reaction. The mixture was centrifuged at 50,000 rpm for 30 min to collect the hydrated GO pellets. After washing with DI water three times, the hydrated GO samples were dispersed in DI water and stored at 4° C.

Physicochemical Characterization of GO Samples.

To obtain AFM images, Si wafers were pretreated by 2.5 mM (3-aminopropyl) triethoxysilane (APTES) aqueous solution for 30 min to functionalize the surface with a monolayer (Green et al. (2009) *Nano Lett.* 9(12): 4031-4036). The wafers were rinsed with DI water and dried under $N_2$. A drop of 10 μg/mL GO solution was placed on the wafer, followed by washing twice with DI water (~5 s) and drying under $N_2$. Then the GO AFM sample underwent heat treatment for 30 min at 250° C. AFM images were obtained by an Asylum Research Cypher ES AFM. Images were taken at random locations in the sample and showed little variation. All images were obtained with the same tip and scanning conditions.

X-ray photoelectron spectroscopy (XPS, AXIS Ultra DLD, Kratos, UK) has been used to investigate the chemical state and calculate the atomic concentration of oxidized groups on GO surface with monochromatic Al Kα at 15 kV and 10 mA. For sample preparation, suspension of GO samples was dropped on the silicon substrate and dried at room temperature. The data analysis and curve fitting were performed with the CasaXPS program (Casa Software Ltd., UK).

The molecular structure of all GO samples were characterized using Raman spectroscopy (Renishaw inVia Reflex, Wotton under Edge, UK) with a 785 nm near-infrared diode and a 50× objective lens. Spectra were obtained for 10 seconds exposure time with an accumulation of 2 scans in the wave number region 500-2000 cm.

The EPR measurements were obtained with an X-band Bruker ELEXYS 580 spectrometer. 5 mg GO nanosheets were dried through vacuum, and allowed to settle to the bottom of the 2 mm ID quartz EPR tubes prior to data collection. The field was calibrated using a standard sample with a known g-factor (2,2-diphenyl-1-picrylhydrazyl, DPPH). The EPR spectra were detected at room temperature with frequency at 9.785845 GHz, center field at 3480 G, attenuator at 13.0 dB and g value at 2.0029.

Zeta-potential and hydrodynamic size measurements of the GO suspensions were performed using a ZetaSizer Nano-ZS instrument (Malvern Instruments, Worcestershire WR, UK).

Assessing the Pro-Oxidative Capability of GO by DCF, XTT and APF Assays.

The oxidation capacity and oxygen species of GO samples were determined as described before (Zhang et al. (2012) *J. Am. Chem. Soc.* 134(38): 15790-15804). 2',7'-dichlorodihydro-fluorescein diacetate ($H_2DCF$-DA) was used to evaluate the total oxidation capacity of GO, while the 3'-(p-aminophenyl) fluorescein (APF) and 3-bis(2-methoxy-4-nitro-5-sulfophehyl)-2H-tetrazolium-5-carboxanilide) (XTT) assays were used to determine $.OH$ and $.O_2^-$ on GO surface, respectively. The DCF working solution was prepared by mixing 50 µg of $H_2DCF$-DA with 280 µL 0.01 M NaOH. The resulting solution was incubated for 30 min, and diluted with 1720 µL of a sodium phosphate buffer (25 mmol/L, pH=7.4) to form 25 µg/mL DCF solution. 95 µL aliquots of 25 µg/mL DCF, 100 µM XTT or 10 µM APF working solutions were added into each well of a 96 multiwell black plate (Costar, Corning, N.Y.). A 5 µL amount of 5 mg/mL nanoparticle suspension was subsequently added to each well, followed by 2 h incubation. DCF fluorescence emission spectra in the range of 500-600 nm were collected using a SpectraMax M5 microplate reader with an excitation wavelength of 490 nm. APF fluorescence emission spectra were collected at 480-600 nm with an excitation wavelength of 455 nm, while XTT absorbance spectra were recorded in the range of 410-550 nm.

Determination of Bacteria Killing by GO.

Five bacterial strains were used in this study: a wildtype *E. coli* strain (ATCC 25922), an AR *E. coli* strain (ATCC BAA-2452), a silver-resistant *E. coli* strain (kindly donated by Dr. Susanne Sitterlin from Department of Clinical Microbiology, Uppsala University, Sweden), a sensitive *L. crispatus* strain (ATCC 53545) and an AR *L. crispatus* strain (ATCC 55221). Bacterial growth was carried out in LB broth (Lennox, Sigma-Aldrich, USA) for *E. coli* and Lactobacilli MRS Broth for *L. crispatus* (BD, Franklin Lakes, N.J., USA), respectively. To assess the bactericidal efficiency of the GO nanosheets, a growth inhibition curve was constructed. In detail, 5 mg/mL stock solution of each material was dispersed in LB and Lactobacilli MRS media at 500 µg/mL. The resulting mixture was sonicated using a sonication probe (Sonics & Materials, USA) at 32 W for 15 s. The GO suspensions were diluted stepwise with the culture media to obtain a series of gradients (7.8, 15.6, 31.3, 62.5, 125, 250 and 500 µg/mL), of which 50 µL of materials suspension was pipetted into 384-well polystyrene microplates. Nine replicate measurements were performed for each concentration. Using a separate plate, 50 µL of a log-phase bacterial culture (OD600 between 0.5~0.7) was pipetted into a 384-well plate, before a plastic 384 pin replicator (Genetix Molecular Devices, USA) was used to inoculate bacteria from the plate to the plate containing the serial dilution of GO samples. Sterility and blank controls (bacterial media with no inoculation) were also included for each concentration (3 replicates). After 24 h incubation at 37° C., a SpectraMax M5 microplate reader was used to monitor $OD_{600}$. A growth curve was constructed using the following equation:

$$\% \text{ Growth} = \frac{A_{NP,B} - A_{NP,M}}{A_B - A_{B,M}} \times 100\%$$

where $A_{Np,B}$ is the absorbance of the bacterial culture in the presence of GO nanoparticles (NPs); $A_{Np,M}$ is the absorbance of the GO NPs at the respective concentrations which contain no bacteria; $A_B$ is the absorbance of the bacterial culture in blank (no GO NPs) media, and $A_{B,M}$ is the absorbance of media with no bacteria (Kaweeteerawat et al. (2015) *ACS Nano*, 9(7): 7215-7225).

TEM Imaging of GO Interaction with Bacteria.

After exposure to 125 µg/mL GO for 24 h, *E. coli* were washed with PBS and fixed with 2% glutaraldehyde in PBS. After post-fixation staining in 1% osmium tetroxide in PBS for 1 h, the cells were dehydrated in a graded series of ethanol, treated with propylene oxide, and embedded in Epon. Approximately 50-70 nm thick sections were cut on a Reichert-Jung Ultracut E ultramicrotome and picked up on Formvar-coated copper grids. The sections were stained with uranyl acetate and Reynolds lead citrate and examined on a JEOL transmission electron microscope at 80 kV in the UCLA BRI Electron Microscopy Core as previously reported (Id.).

Assessment of Bacterial Membrane Lipid Peroxidation.

AR *E. coli* bacteria were treated with 250 µg/mL GO samples for 6 h or 10 M cumene hydroperoxide (positive control) for 1 h. The cells were then washed twice, incubated with 10 µM Image-iT® Lipid Peroxidation Sensor and Hoechst 33342 in culture media for 30 min. After staining, the cells were washed three times with PBS, and fluorescence readings were obtained for the reduction and oxidation of the dye at excitation/emission wavelengths of 581/591 nm (Texas Red® filter set) and 488/510 nm (traditional FITC filter), respectively. The ratio of the emission fluorescence intensities at 590 nm to 510 nm gives a read-out for cellular lipid peroxidation. The flow cytometry analysis was carried out on a FACS Vantage SE flow cytometer from BD (Franklin Lakes, N.J.). The flow cytometric data were collected and processed using Flowjo Software (Ashland, Oreg.). The confocal laser scanning microscopy analysis was performed by a TCSSP2 confocal laser scanning microscope (Leica, Wetzlar, Germany).

Assay for β-Galactosidase Release from Bacteria.

Permeabilization of the *E. coli* plasma membrane was evaluated by measuring β-galactosidase activity with a Beta-Glo® Assay System (Promega) (Liu et al. (2004) *Int. J. Food Microbiol.* 95(2): 147-155; Jan et al. (2013) *J. Food Prot.* 76(9): 1523-1529). In detail, 250 µL aliquots of AR *E. coli* in log phase growth ($A_{600}$~0.7) were centrifuged to collect the cell pellets. These pellets were resuspended in 250 µL fresh medium or each of the GO suspensions at 250 µg/mL. The supernatants were collected after 15,000 rpm centrifugation for 5 min. The positive control was comprised of non-treated cell pellets that were mixed with 250 µL cell lysis buffer for the release of their (3-galactosidase content. 50 µL aliquots of the supernatant or lysis solutions were added to the wells of 96-well plate, before the addition of 50 µL β-galactosidase substrate. Following mixing and incubation at room temperature for 2 h, the luminescence intensity was recorded in a SpectraMax M5 microplate reader. The percentage of β-galactosidase release was calculated according to the formula:

$$\frac{L_{GO}}{L_{ctrl} + L_{lysis}} \times 100\%$$

where $L_{GO}$ is the luminescence intensity in supernatants of GO treated samples, while $L_{ctrl}$ and $L_{lysis}$ represents the luminescence values in ctrl supernatant and ctrl cell pellet lysis, respectively.

Synthesis of hGO-2 Thin Films on a Glass Substrate and on a Silicon Catheter Surface.

A Laurell WS-650Sz spin coater was used to fabricate noncovalent hGO-2 coatings on 18 mm×18 mm×0.15 mm glass substrates. The substrates were placed on a rotor followed by spinning at 1000 rpm. 2 mg/mL GO suspensions were added onto the substrate surfaces using a pipette until the desired thickness was obtained. Films were dried at 50° C. overnight. These thermal treatments imparted good film-substrate adhesion as thin films were resistant to rubbing off. Image J was used to analyze the AFM images and determine the surface area coverage (Li et al. (2014) *ACS Nano*, 8(10): 10280-10292).

To covalently coat a silicone catheter surface with hGO, silicone tubes were cleaned twice with acetone, DI water and isopropanol in a sonication bath. After 1 min plasma cleaning at high radio frequency, silicone catheters were reacted with 10 μL APTES in 20 mL isopropanol alcohol (IPA) for 3 h, washed twice with IPA, DI water and ethanol, and placed at 105° C. for 30 min. The aminated catheters were cooled down to room temperature and immersed in 5 mL 250 μg/mL carbodiimide GO solutions, which were prepared by stirring 5 mL GO (250 μg/mL), 1-ethyl-3-(-3-dimethylaminopropyl) carbodiimide hydrochloride (EDC, 0.123 mg/mL) and N-Hydroxysuccinimide (NHS, 0.105 mg/mL) in aqueous solution for 3 h, followed by filtration and re-dispersion in 5 mL DI water. After 24 h reaction while stirring, GO modified catheters were washed twice with DI water and ethanol. The entire process was considered as a complete coating cycle. For example, to achieve a second coating, the modified catheter is once again reacted with APTES to create an aminated surface and subsequently submerged in the carbodiimide GO solution. In this study, the GO modified catheters were coated with hGO-2 for 1, 3, 5 and 10 cycles, and designated as 1C, 3C, 5C and 10C, respectively. Both the noncovalent and covalent coated GO films were further characterized by a Thermo Microscopes Autoprobe CP-Research AFM and a Renishaw inVia Reflex Raman spectroscope.

Assessment of the Bactericidal Effects of hGO-2 Films.

Inhibition of bacterial growth on hGO-2 coated substrates was determined by a modified protocol (Kuma et al. (2008) *Nat. Mater.* 7(3): 236-241). AR *E. coli* in log phase were collected by centrifugation at 15,000 rpm for 5 min, washed twice with PBS, and diluted in fresh LB medium with O.D. at 0.7. Bacteria were exposed to hGO-2 films by immersing the coated substrates (18×18 mm) or catheters (5×5 mm) in bacteria suspensions for 5 min. The substrates were air dried for 30 min to allow the attachment of bacteria to the surface. The bacteria settling on catheter surfaces were then placed in a Petri dish with fresh broth and incubated at 37° C. for 1, 3 or 6 h. The growing bacteria were collected to perform 10-fold serial dilutions in 1 ml PBS. Aliquots (0.1 mL) of each dilution were introduced to LB agar plates for 24 h incubation. Colonies were counted under a microscope, and the desired colony numbers (20-300) at appropriate dilutions were used to calculate CFU by following formula: CFU (mL$^{-1}$)=N×10$^n$/0.1, where N is the colony number on agar plates at 10n dilution. The bacteria grown on glass substrates were stained by propidium iodide (PI) and Hoechst 33342 for 30 min. Then the glass substrates were gently rinsed thrice with PBS and fixed with 70% ethanol. Bacterial cell death on the coated substrates was determined by visualizing the percentage of PI-positive cells under a Leica Confocal SP2 1P/FCS microscope. In addition, scanning electron microscopy (SEM, ZEISS SUPRA 40VP) was used to evaluate the surface morphology of *E. coli* grown on hGO-2 films. Prior to SEM analysis, the prepared samples were mounted on the SEM stubs and coated by PELCO SC-7 sputter for 30 sec at 30 mA to generate a thin Au/Pt conductive layer (2-20 nm).

Statistics.

Mean and standard deviation (SD) were calculated using a minimum of 3 observations for each parameter, such as bacterial absorbance at 600 nm, intensity of .C on EPR spectra, % of PI-stained bacteria, etc. Comparisons between groups were evaluated by two-side Student's t test or one-way ANOVA. A statistically significant difference was assumed for $p<0.05$.

Example 2

The Surface Oxidation of Graphene Oxide Determines Membrane Damage, Lipid Peroxidation, and Cytotoxicity in Macrophages in a Pulmonary Toxicity Model Graphene is increasingly being used for a broad range of applications in electronics, energy, sensors, and catalysis due to its high electronic and thermal conductivity, high surface area, and extraordinary mechanical properties (Chen et al. (2012) *Chem. Rev.* 112: 6027-6053; Compton et al. (2010) *Small*, 6: 711-723). Moreover, the graphene derivative, graphene oxide (GO), exhibits excellent dispersibility, colloidal properties and the potential to use surface functionalization to render the material attractive for use in biomedicine, including tissue engineering (Akhavan, et al. (2016) *Carbon*, 97: 71-77), antimicrobial agents (Li et al. (2016) *ACS Nano*, 10: 10966-10980), bioimaging (Zheng et al. (2015) *Small*, 11: 1620-1636), and drug delivery (Chen et al. (2015) *Chem. Soc. Rev.* 44: 2681-2701). In order to be successfully translated to products that can be used in the marketplace, it is important to understand the safety and biocompatibility of GO (Sydlik et al. 92015) *ACS Nano*, 9: 3866-3874; Zhang et al. (2016) *Adv. Drug Deliv. Rev.* 105: 145-162). Although there has been an extensive body of work regarding the potential toxic effects of GO in bacteria, including its use for antibacterial applications (Li et al. (2016) *ACS Nano*, 10: 10966-10980; Akhavan et al. (2010) *ACS Nano*, 4: 5731-5736; Li et al. (2013) *Proc. Natl. Acad. Sci. USA*, 110: 12295-12300), the toxicity profile of GO in mammalian systems is still incomplete (Sydlik et al. 92015) *ACS Nano*, 9: 3866-3874; Zhang et al. (2016) *Adv. Drug Deliv. Rev.* 105: 145-162).

Studies looking at GO antibacterial effects have demonstrated the importance of considering the contribution of its planar 2D structure, lateral size, edges, surface functional groups and oxidation status in interactions with the bacterial membrane (Li et al. (2016) *ACS Nano*, 10: 10966-10980; Akhavan et al. (2010) *ACS Nano*, 4: 5731-5736; Azimi et al. (2014) *Science of Advanced Materials*, 6: 1-11; Yang et al. (2010) *Nat. Nanotechnol.* 5: 579-583; Chen et al. (2013) *J. Nanopart. Res.* 15: 1658; Pham et al. (2015) *ACS Nano*, 9, 8458-8467). Theoretical simulations as well as experimental data demonstrated that the sharp corners and edge protrusions of GO enable these materials to penetrate bacterial membranes, with the possibility to extract lipid molecules and induce membrane disruption (Li et al. (2013) *Proc. Natl. Acad. Sci. USA*, 110: 12295-12300). The expression of epoxy, hydroxyl, and carbon radical groups on the surface, together with carboxyl groups on the edges, contribute to bactericidal effects (Li et al. (2016) *ACS Nano,* 10: 10966-10980). In contrast, a detailed understanding of how the complicated GO chemistry engages mammalian systems is still unclear and requires additional study (Li et al. (2016) *ACS Nano,* 10: 10966-10980; Hu et al. (2010) *ACS Nano,* 4: 4317-4323; Liu et al. (2011) *ACS Nano,* 5: 6971-6980). Among the reported effects of GO in mammalian cells is the delineation of induction of cell death (Zhang et al. (2016) *Adv. Drug Deliv. Rev.* 105: 145-162). For instance, studies have shown that GO could induce dose-dependent cell death in normal lung fibroblasts (HLF), macrophages (THP-1 and J744A), epithelial (BEAS-2B) cells, lung cancer cells A549, etc (Id.). However, the data are inconsistent and even contradictory with respect to how physicochemical properties like the lateral flake size, surface coating (PVP, PEG, Pluronic), and oxidation states contribute to toxicological effects in mammalian systems (Id.). Since GO nanosheets have also been reported to induce inflammation and fibrogenic effects in the lung (Wang et al. (2015) *ACS Nano,* 9: 3032-3043), we hypothesized that the oxidation status and surface reactivity of the material play a key role in these adverse outcomes, and that this organ system could be useful to delineate the structure-activity relationships related to deliberate variation of the surface properties (Li et al. (2016) *ACS Nano,* 10: 10966-10980).

In order to discern the role of the oxidative modification of the go surface in bacteria, we prepared a library of materials in which the relative abundance of the surface reactive groups was changed by catalytic chemistry (Id.). One approach was solvothermal reduction to quantitatively reduce GO oxidation levels, while another was the use of hydrolysis by alkalized aqueous solvents to open the epoxy rings, thereby increasing hydroxyl and carbon radical densities (Id.). This yielded a library of pristine, reduced (rGO) and hydrated GO (hGO) nanosheets that were thoroughly characterized for oxygen content, other surface groups, carbon radical content and biological oxidative potential (Id.). In the current communications, a new library of pristine, rGO and hGO nanosheets were prepared to delineate the effects of the surface functional groups in pulmonary epithelial cells and macrophages, as well as the murine lung. The in vitro experimentation was followed by oropharyngeal instillation into the murine lung, focusing on mechanistic injury responses that may explain how adverse effects at cellular level relate to and adverse outcome at organ level. We identified the critical role of surface functional groups, including carbon radicals, in impacting GO biocompatibility in the lung. This includes adverse effects on the cellular membrane, cytotoxicity, and cellular uptake, leading to pro-inflammatory effects in the lung.

Results

Preparation and Characterization of GOs

Figure 17:
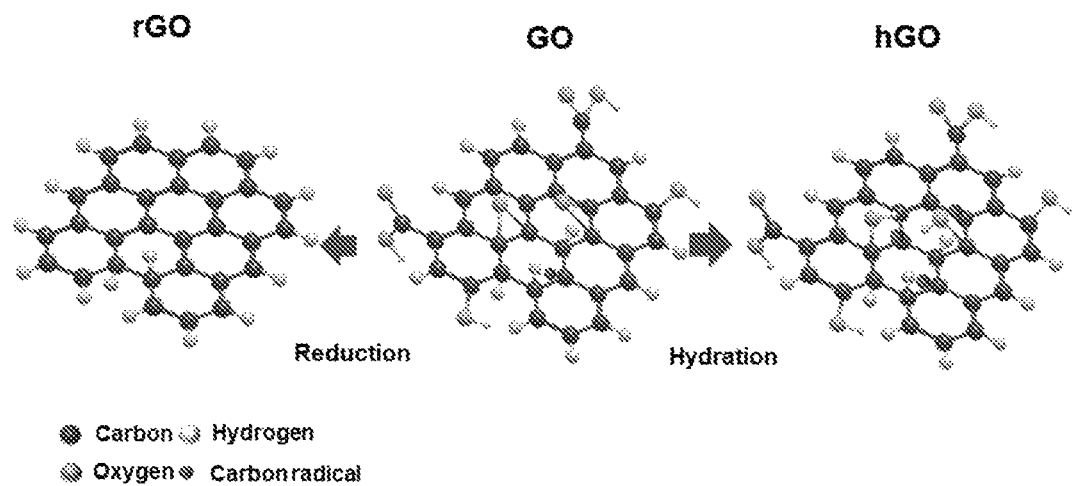
FIG. 17 shows scheme 1 illustrating the synthesis of reduced and hydrated GO samples. Pristine GO was prepared by a modified Hummers' method. Reduced GO materials were synthesized by solvothermal reduction of GO in NMP at 150° C. for 1 or 5 h. Hydrated GO nanosheets were prepared by hydrolysis in an aqueous alkalized solution at 50° C. or 100° C. for 24 h. Surface reduction decreases surface oxidation levels, while hydration has the opposite effect.
Figure 18A:
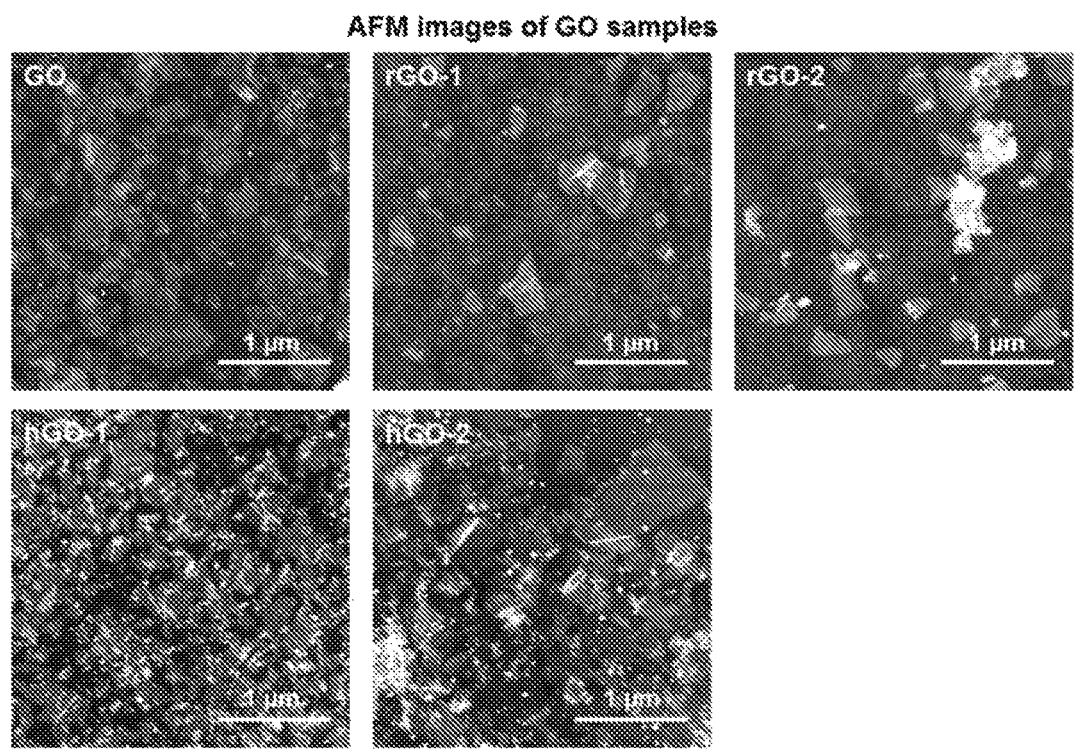
FIGS. 18A-18D illustrate characterization of the physicochemical properties of GO samples.
Figure 18B:
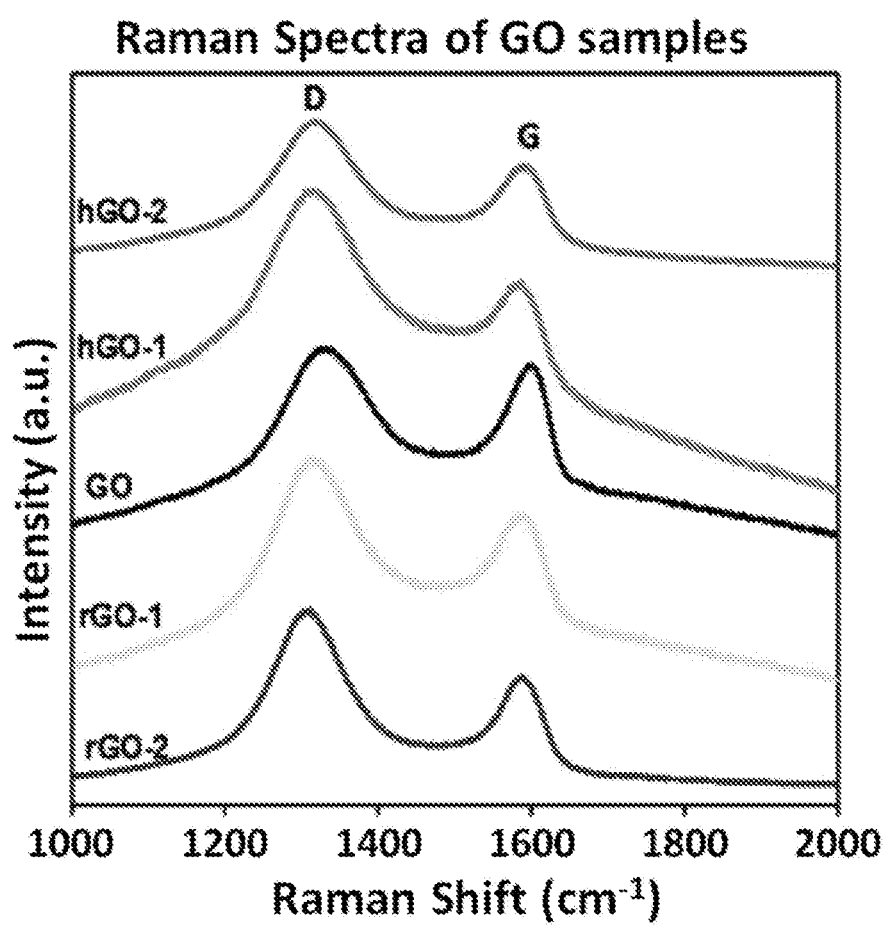
Figure 24:
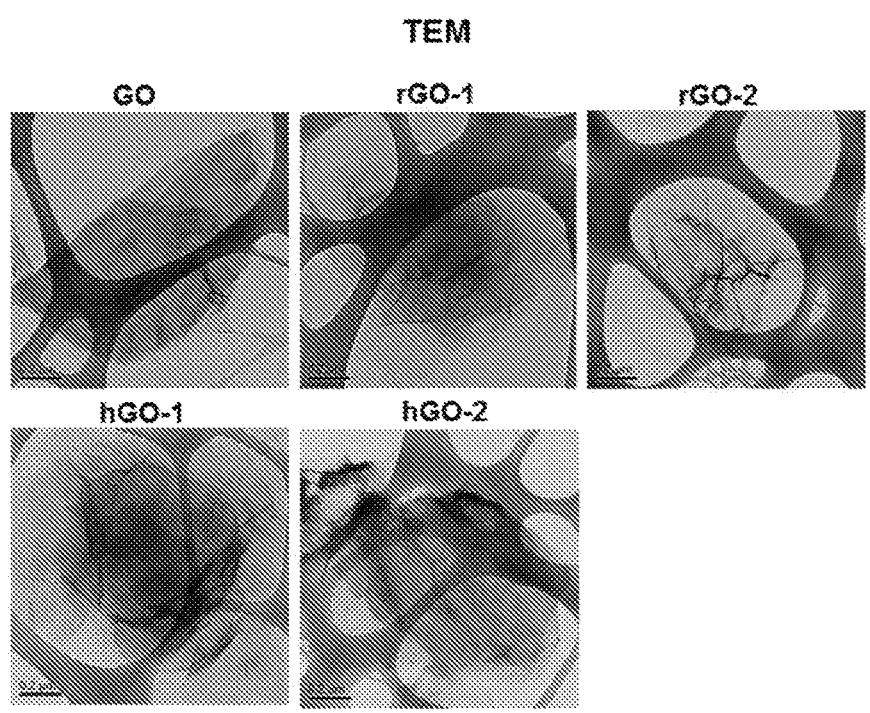
FIG. 24 illustrates characterization of GO samples by TEM. TEM images of GO samples were obtained by dropping GO suspensions (25 µg/mL) on Cu grids. After drying at room temperature, the images were taken on a JEOL 1200 EX TEM with accelerating voltage 80 kV.

To assess the biohazardous potential of key functional groups on GO, a material library was prepared by using reduction or hydration of pristine GO, as previously described (FIG. 17, Scheme 1). Two reduced GO samples were obtained by solvothermal reduction in N-methyl-2-pyrrolidinone (NMP) for 1 h (rGO-1) and 5 h (rGO-2). Moreover, we prepared two hydrated GO materials by suspending pristine GO in an alkalized solution at temperatures of 50° C. (hGO-1) and 100° C. (hGO-2), respectively. Detailed physicochemical characterization of these materials was performed. Atomic force microscopy (AFM) results show that all GO samples were composed of nanosheets with irregular shape, and lateral dimensions of ~50-300 nm (FIG. 18A). The transmission electron microscope (TEM) images were consistent with the AFM images, showing the stacking of GO nanosheet layers with negligible inter-material differences (FIG. 24). Raman spectra showed the typical D and G bands representative of graphene and confirming minimal structural changes through the use of reduction or hydration. These bands represent the stretching of the graphitic out-of-plane C—C bonds (D band) and in-plane G band, respectively (FIG. 18B). There were no differences in the intensity ratio of the D vs. G bands (ID/IG ratio) in the various materials, which indicative of similar levels of defect density on the GO surface (Grimm et al. (2016) *J. Phys. Chem.* C, 120: 3036-3041). Due to the intended material use in cellular studies, we also were assessed the hydrodynamic size and zeta potential of the materials in deionized water (DI $H_2O$) and the tissue culture media (Table 4). Most GO samples showed agglomeration in DI $H_2O$, resulting in hydrodynamic diameters of 330-440 nm, except for rGO-2 that showed larger (550 nm) agglomerates as a result in the reduction in hydrophilicity. All GO samples showed hydrodynamic diameter sizes of 320-460 nm in RPMI 1640 medium compared to a size range of 550-600 nm in BEGM medium; the reduced size in the former medium is due to the presence of a high concentration of serum albumin, which leads to the formation of a protein corona.

TABLE 4

| | Zeta potential and Hydrodynamic size off-GO in different media | | | | | |
|---|---|---|---|---|---|---|
| Nanoparticles | | GO | rGO-1 | rGO-2 | hGO-1 | hGO-2 |
| Hydrodynamic Size (nm) | Water | 334.1 ± 3.1 | 378.1 ± 3.9 | 549.2 ± 1.5 | 307.5 ± 6.7 | 329.8 ± 7.0 |
| | BEGM | 589.4 ± 23.2 | 596.5 ± 14.3 | 596.4 ± 2.4 | 546.7 ± 10.2 | 555.1 ± 38.4 |
| | RPMI | 321.5 ± 6.5 | 432.1 ± 27.4 | 456.5 ± 5.1 | 337.8 ± 9.8 | 340.8 ± 25.0 |
| Zeta Potential (mV) | Water | −51.7 ± 0.9 | −36.3 ± 1.4 | −24.4 ± 0.7 | −50.6 ± 0.8 | −49.4 ± 0.9 |
| | BEGM | −18.5 ± 0.6 | −8.7 ± 2.7 | −8.2 ± 2.2 | −16.7 ± 0.8 | −14.7 ± 2.5 |
| | RPMI | −7.5 ± 0.5 | −5.5 ± 1.2 | −6.5 ± 3.6 | −7.9 ± 3.9 | −6.4 ± 2.2 |

Figure 18C:
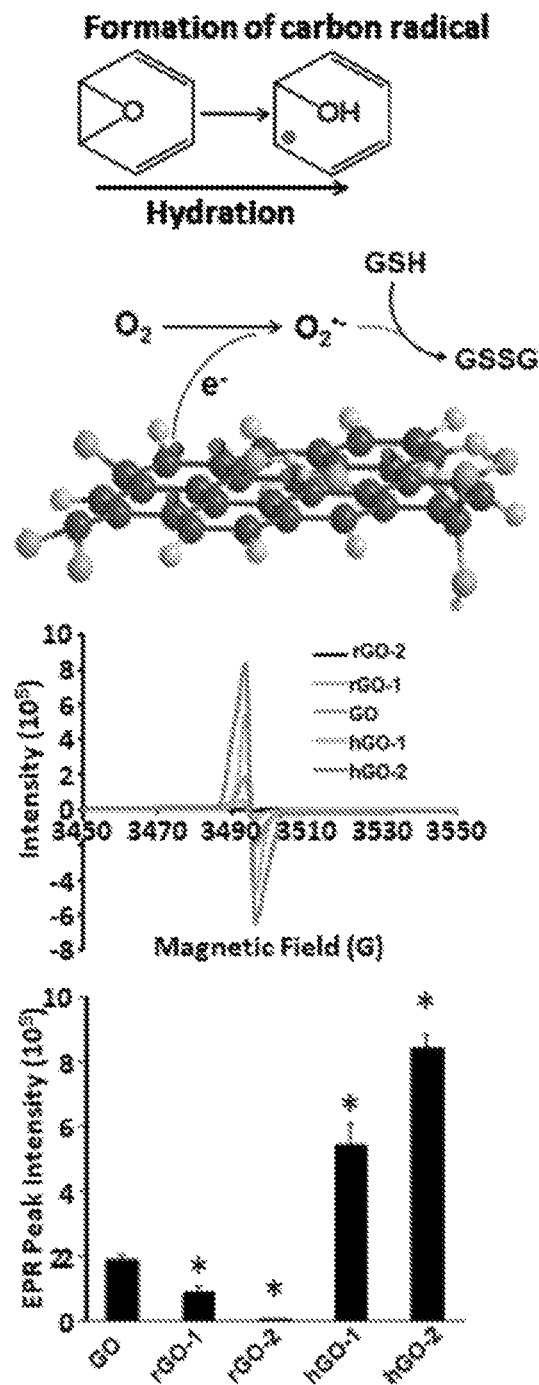
Figure 18D:
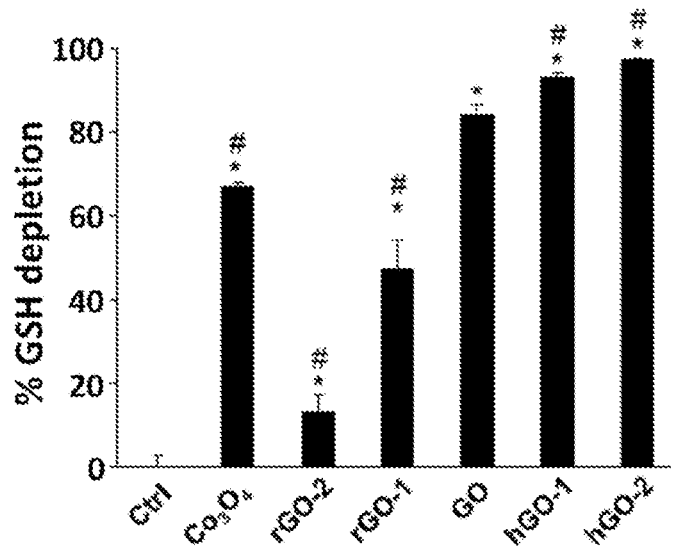

We also performed extensive characterization of the surface functional groups. X-ray photoelectron spectroscopy (XPS) was used to characterize the oxygen functional groups. As shown in Table 5, the reduction of GO to rGO-2 was accompanied by a significant decrease in oxygen-containing moieties as well as surface defects. The atomic percentages of total oxygen, C—OH, C═O and C—O—C decreased from 36.7 to 16.5%, 6.8 to 4.1%, 9.4 to 8.3%, and 20.5 to 4.1%, respectively. During the hydration process, epoxy rings react with nucleophiles in aqueous solution, generating C—OH groups and carbon radicals (Li et al. (2016) *ACS Nano,* 10: 10966-10980) (FIG. 18C). We used electron paramagnetic resonance (EPR) to assess the presence of surface carbon radicals (.C), as demonstrated in FIG. 18C. GO samples that contain π-conjugated carbon radicals, showed EPR peaks at g=2.0029 (Id.). For rGO-2, the .C peak intensity is reduced from $1.85 \times 10^5$ for pristine GO to extremely low level ($0.01 \times 10^5$) (Table 5). In contrast, the hydration reaction increases carbon radical density ($8.38 \times 10^5$ for hGO-2), accompanied by a decrease in C—O—C and an increase in C—OH groups (Table 5, FIG. 18C). Carbon radicals are typically considered more reactive than other surface functionalities due to the presence of unpaired electrons. These electrons are capable of reacting with molecular dioxygen to generate superoxide radicals, which are capable of oxidizing unsaturated lipids and thiol groups on proteins or glutathione (GSH) (FIG. 18C) (Zhao et al. (2015) Env. Sci.: Nano. 2: 136-142). GSH also plays a major role in maintaining redox equilibrium in cells, whether ratio of reduced to oxidized glutathione (GSSG) is important in cellular homeostasis, with the potential to trigger a series of hierarchical oxidative stress responses (Xia et al. (2016) Nat. Sci. Rev. 3: 416-429; Nel et al. (2009) Nat. Mat., 8: 543-557; Nel et al. (2013) Acc. Chem. Res. 46: 607-621; Nel et al. (2006) Sci. 311: 622-627). Thus, we chose GSH as a model system to test the pro-oxidative potential of GO, using an abiotic GSH-Glo™ assay (FIG. 18D). While hGO-2 could deplete GSH by 96%, the respective values for pristine GO and rGO-2 were 80% and 16%, respectively. In summary, there is good agreement between the carbon radical density on the GO surface, the degree of pro-oxidant activity and the extent of GSH depletion (Li et al. (2016) ACS Nano, 10: 10966-10980).

TABLE 5

GO surface functional groups, carbon radical density and defect levels

| | | rGO-2 | rGO-1 | GO | hGO-1 | hGO-2 |
|---|---|---|---|---|---|---|
| XPS (atomic %) | Total oxygen | 16.5 | 21.2 | 36.7 | 30.2 | 27.8 |
| | C—OH | 4.1 | 5.3 | 6.8 | 11.3 | 14.5 |
| | C=O | 8.3 | 8.8 | 9.4 | 10.7 | 12.2 |
| | C—O—C | 4.1 | 7.4 | 20.5 | 9.2 | 1.1 |
| EPR ($10^5$) | •C | 0.01 | 0.84 | 1.85 | 5.38 | 8.38 |
| Raman ($I_D/I_G$) | Defects | 1.07 | 1.13 | 1.17 | 1.05 | 0.95 |

Plasma Membrane Association and Cellular Uptake of GO

Figure 19A:
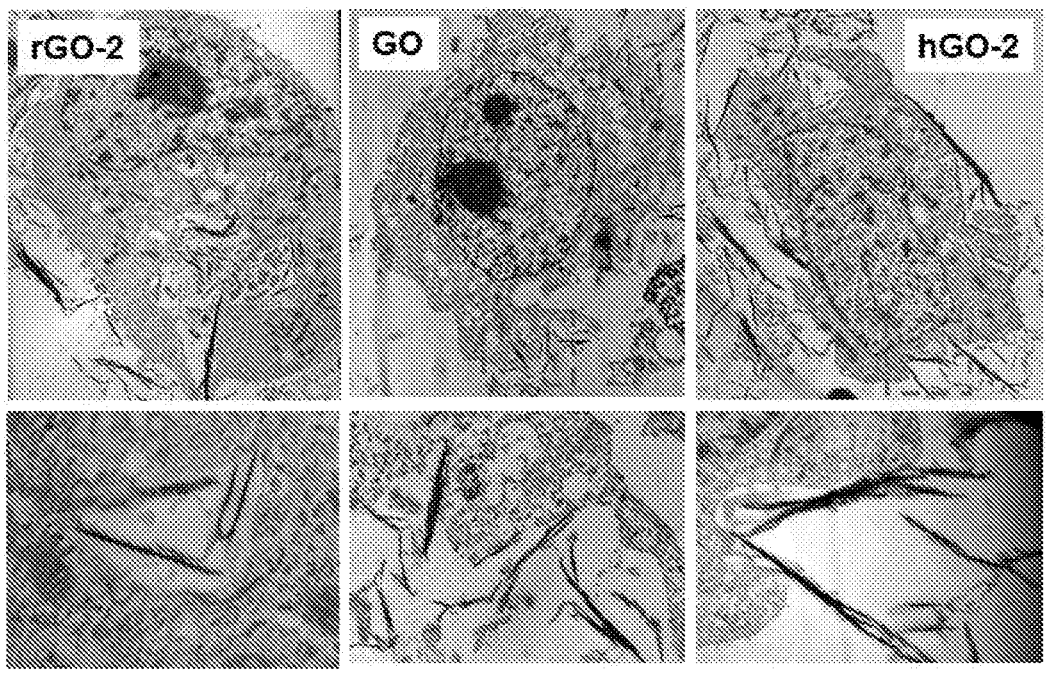
FIGS. 19A and 19B illustrate determination of the cellular interactions with the functionalized GO nanosheets.
Figure 19B:
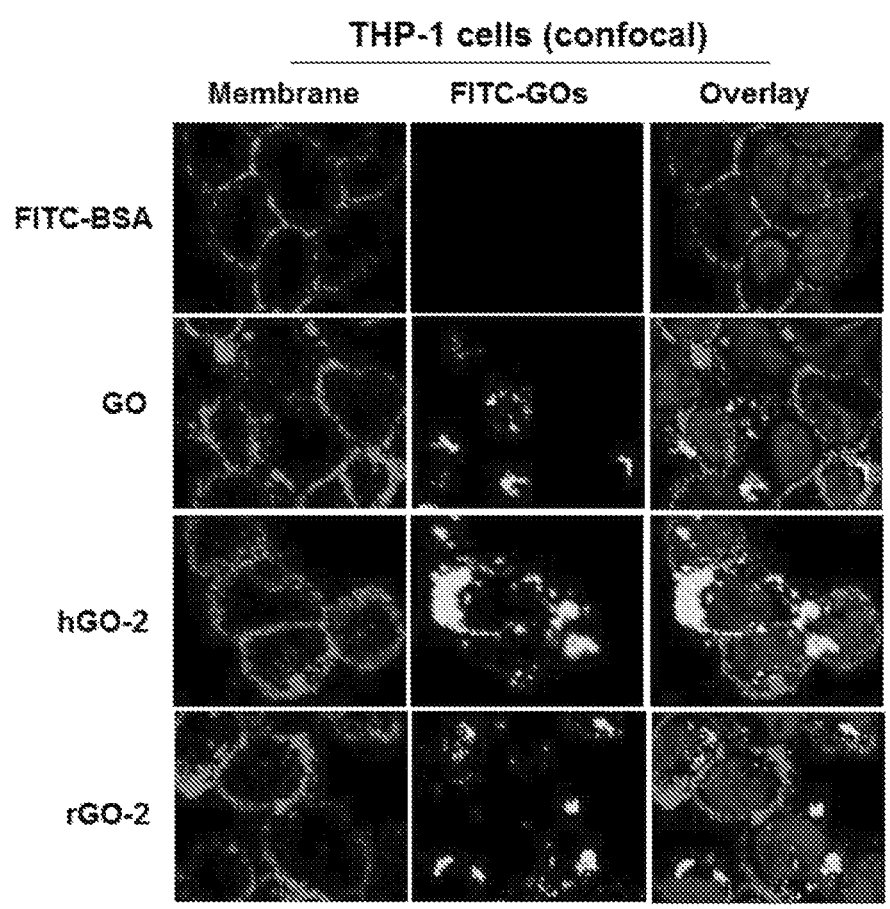
Figure 25:
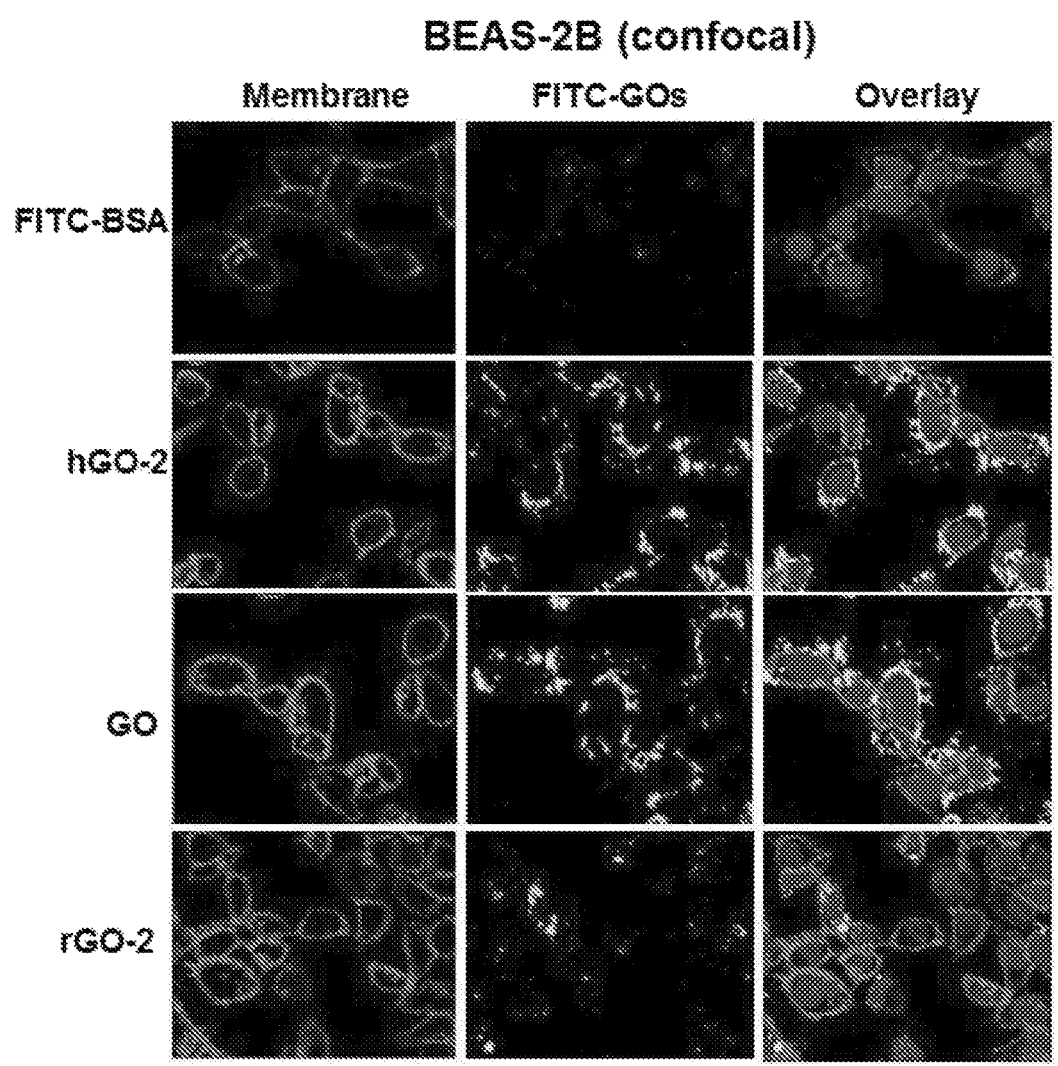
FIG. 25 illustrates the determination of the cellular interactions with the functionalized GO nanosheets. Use of confocal microscopy to visualize the interaction of FITC-BSA labeled GO samples with BEAS-2B cells. After exposure to rGO-2, GO or hGO-2 for 16 h, the cells were washed, fixed and stained for confocal imaging of FITC-BSA labeled GO. The nucleus was stained with Hoechst 33342 dye (blue) and Alexa fluor 594-labeled WGA antibody was used to identify cell membrane.

Cellular responses to GO are dependent on physical interactions with the plasma membrane, following which there is the possibility of cellular uptake and the potential to interact with subcellular structures (Zhang et al. (2016) Adv. Drug Deliv. Rev. 105: 145-162). Previous studies have demonstrated that the lateral GO flake size may determine cellular interactions to the extent that a large lateral size may restrict the ability to be taken up by cells (Ma et al. (2015) ACS Nano, 9: 10498-10515). In accordance with this view, smaller GO flakes were more readily taken up into the cell without significant interaction with the plasma membrane Id.). The study did not take into consideration the impact of surface functionality and the oxidation status of GO. To clarify this point, THP-1 cells were incubated with pristine, reduced and hydrated GO samples for 16 h, before TEM analysis (FIG. 19A). And limitation of this technique is that the low electron density of GO, only allows visualization of the suspended GO when vertically positioned but for nanosheets that are horizontally aligned with the grid. Nonetheless, in spite of the shortcoming it was possible to demonstrate that GO or hGO-2 nanosheets insert or attach to the surface membrane of THP-1 cells (FIG. 19A). This interaction with the mammalian cell lipid bilayer is likely premised on the amphiphilic nature of these materials, which display a hydrophobic planar structure with hydrophilic edges (Kim et al. (2010) J. Am. Chem. Soc. 132: 8180-8186). In contrast, rGO-2 has a reduced number of hydrophilic edge groups, is more hydrophobic in nature and is principally internalized by phagocytic uptake in THP-1 cells. The TEM observations were further substantiated by visualizing the cellular processing of FITC-BSA labeled GO samples in THP-1 (FIG. 19B) and BEAS-2B cells (FIG. 25). Confocal microscopy demonstrated that while hGO and GO showed extensive accumulation in proximity to the surface membrane, without much cellular uptake, rGO did not localize at the surface membrane and could be visualized inside cells.

Pristine and hGO Induce Lipid Peroxidation of the Surface Membrane

Figure 20A:
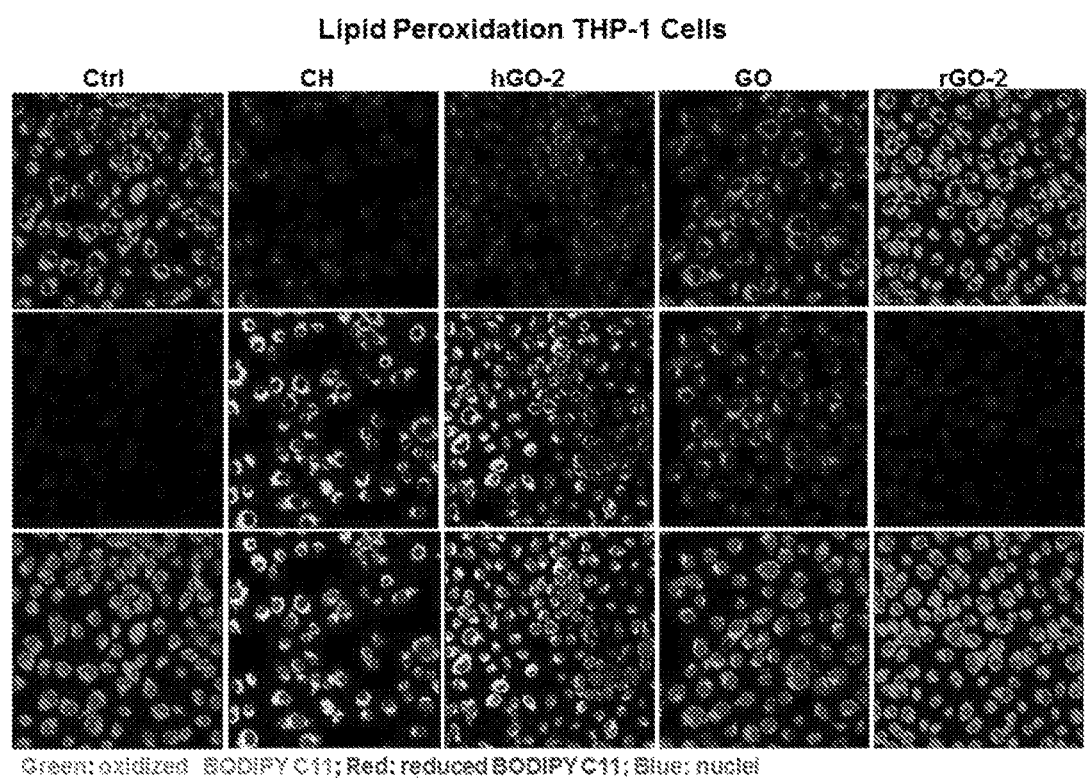
FIGS. 20A-20C illustrate an assessment of the lipid peroxidation and hemolygis by GO nanosheets.
Figure 20B:
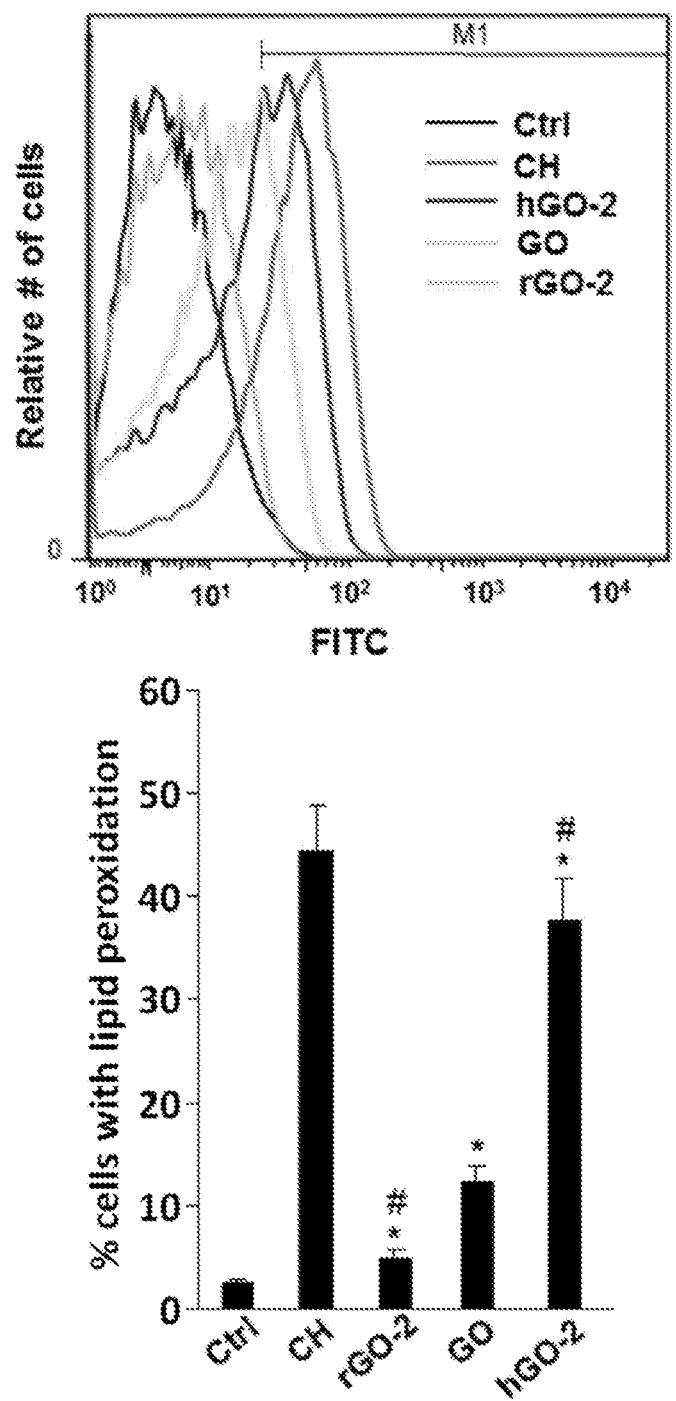
Figure 20C:
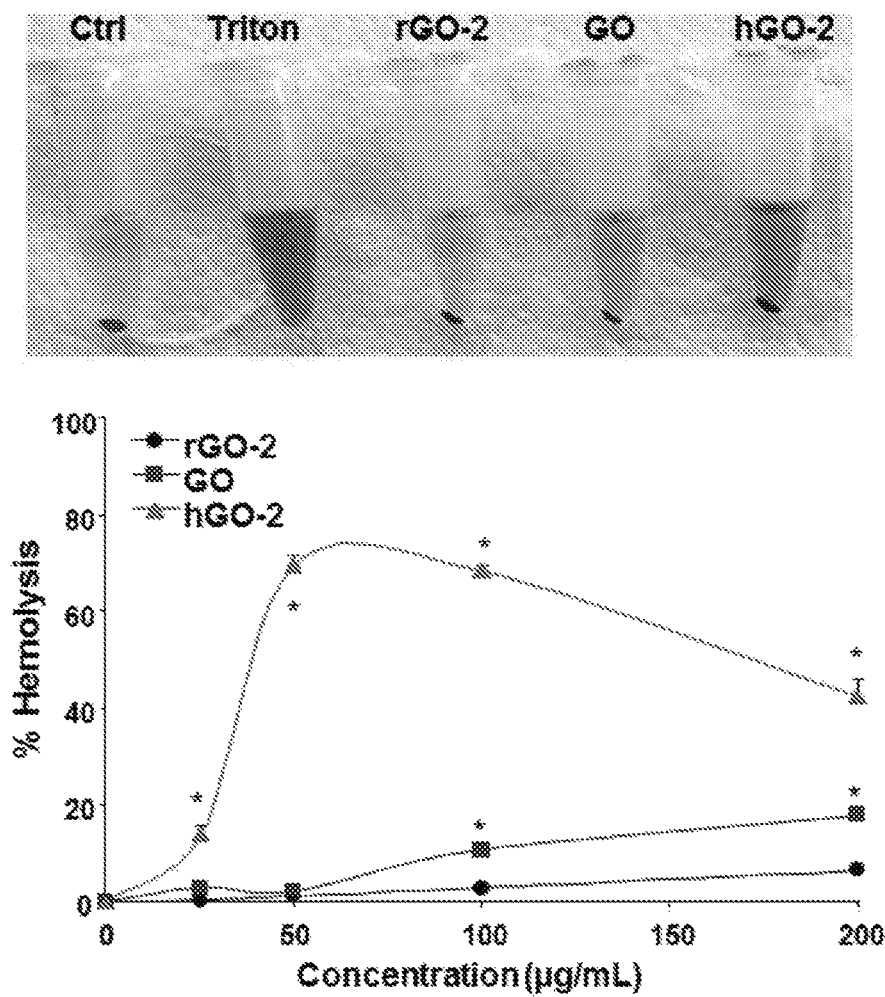

Since pristine GO and hGO-2 are capable of GSH depletion (FIG. 18D), we were interested to see if this leads to lipid peroxidation during the accumulation of these materials at the surface membrane. Lipid peroxidation was studied by using the BODIPY® 581/591 C11 reagent to visualize the green shift (~510 nm) in fluorescence activity (from red at ~590 nm) in the presence of lipid peroxides. As shown in the confocal microscopy images in FIG. 20A, cumene hydroperoxide (CH), used as a positive control reagent, induced a substantial switch to green fluorescence at the expense of the red fluorescence in the plasma membrane of THP-1 cells. While pristine GO also the ship to faint red fluorescence, hGO-2 had a pronounced effect, while the effect of rGO-2 was limited. The data was also quantitatively expressed by conducting flow cytometry and calculating the percentage of cells exhibiting increased fluorescence intensity at 510 nm (FIG. 20B). This showed that relative abundance of lipid peroxidation in THP-1 amounts to 13, 37 and 5% of cells in the population in response to pristine GO, hGO-2 and rGO-2, respectively. Lipid peroxidation can lead to a failure in membrane integrity. Direct evidence of membrane damage was provided by using a hemolysis assay in red blood cells (RBC). RBC lack fluid phase or receptor-mediated endocytosis, and is widely used to study nanomaterial interactions with the membrane (. Li et al. (2014) ACS Nano, 8: 1771-1783; Zhang et al. (2012) J. Am. Chem. Soc. 134: 15790-15804). While the hemolysis assay demonstrated little or no RBC lysis during rGO-2 treatment, pristine GO showed dose-dependent hemolysis, which amounted to 20% of cells being lysed at 200 jag/ml (FIG. 20C). In contrast, the hemolytic potential of hGO-2 amounted to 68% of RBCs lysed at 50 jag/ml (FIG. 20C). These results are in good agreement with the change in membrane peroxidation.

Induction of Cytotoxicity by GO Nanosheets

Figure 21A:
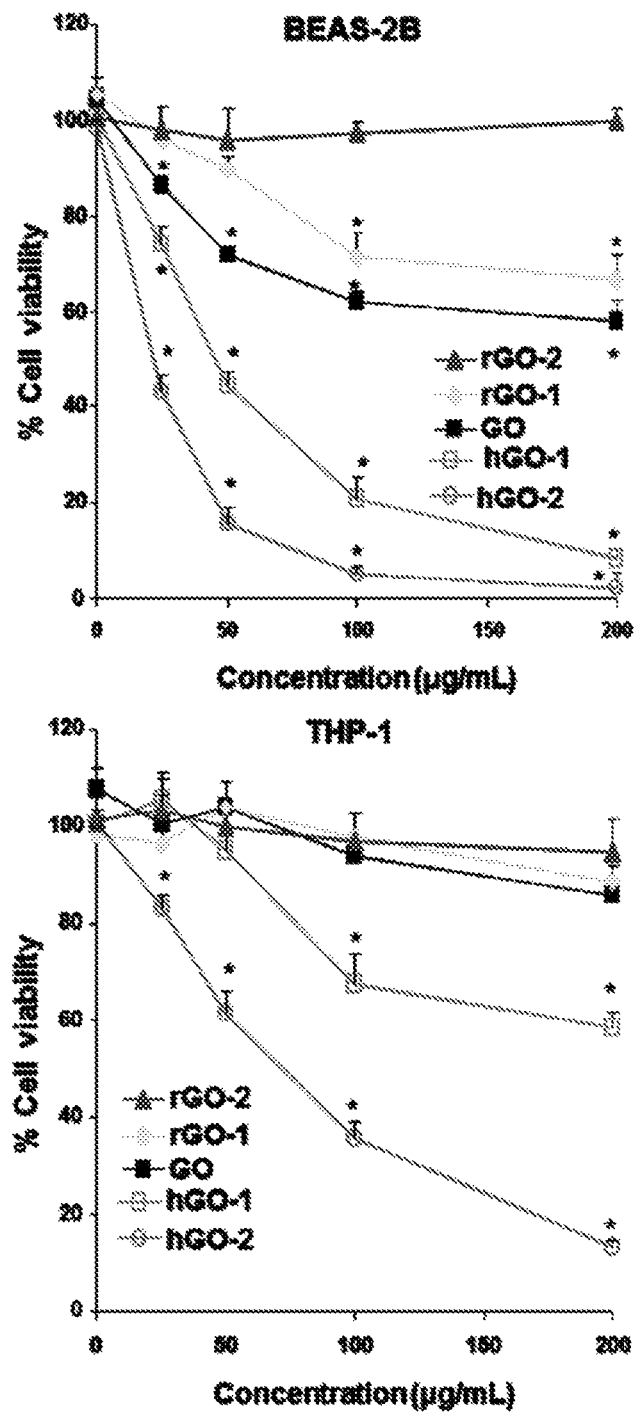
FIGS. 21A-21C illustrate the assessment of the cytotoxicity of the library of GO materials.
Figure 21B:
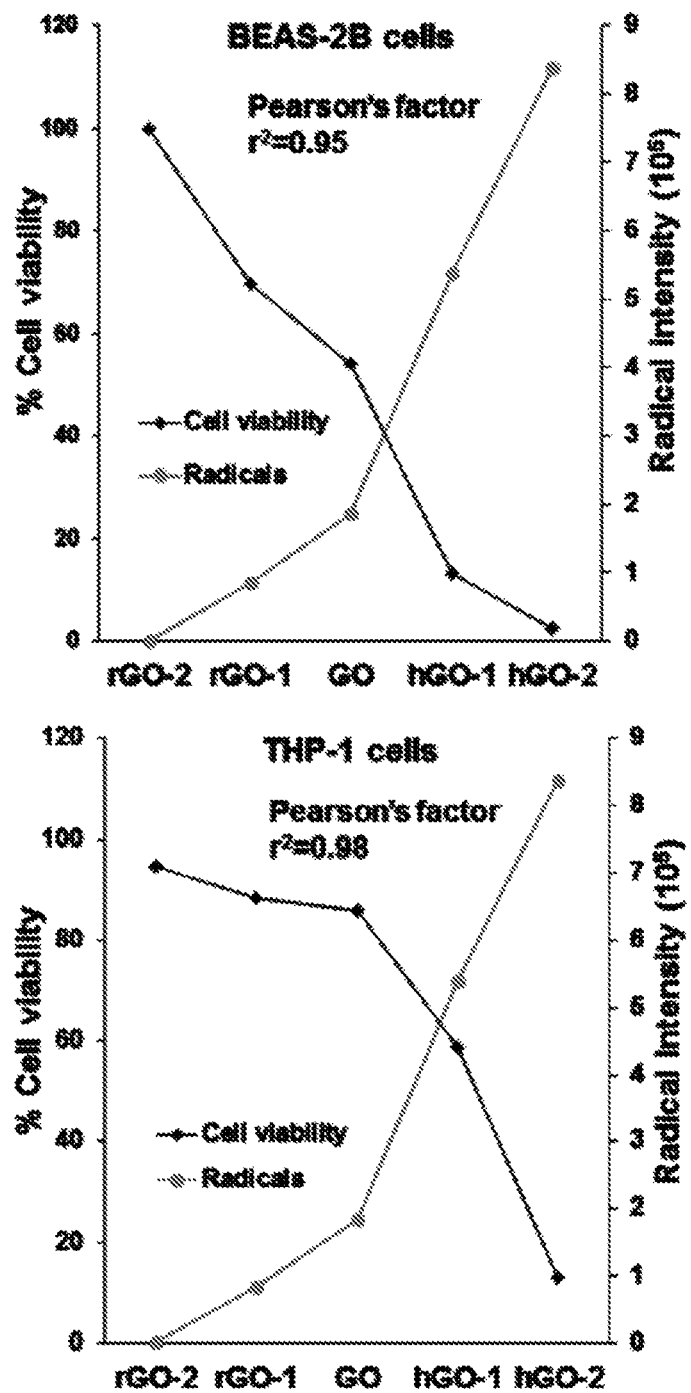
Figure 21C:
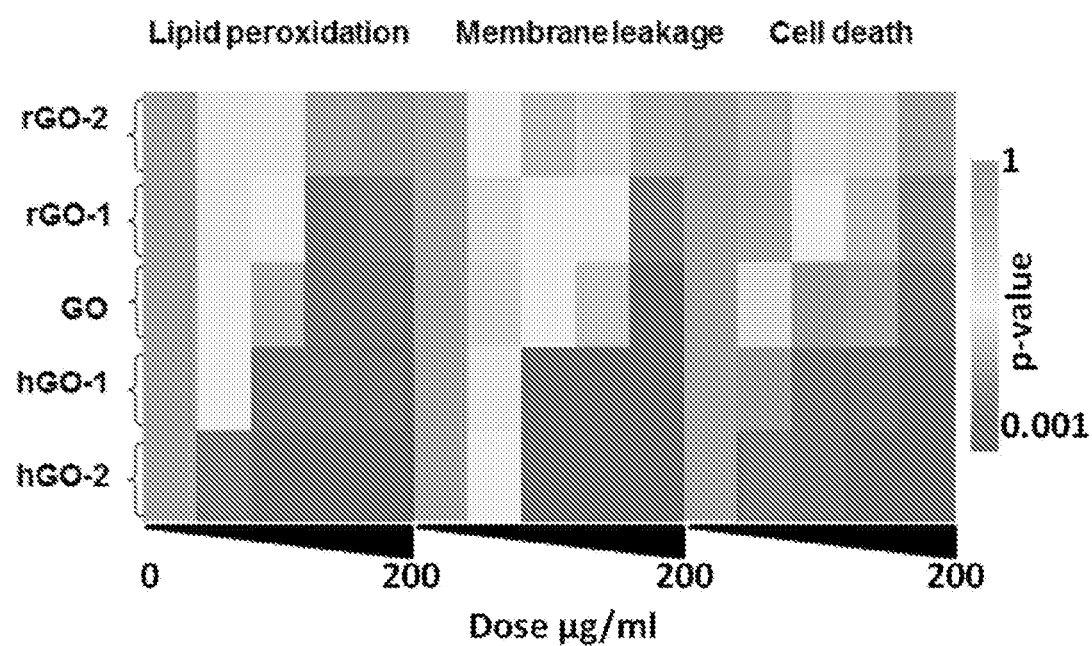
Figure 26:
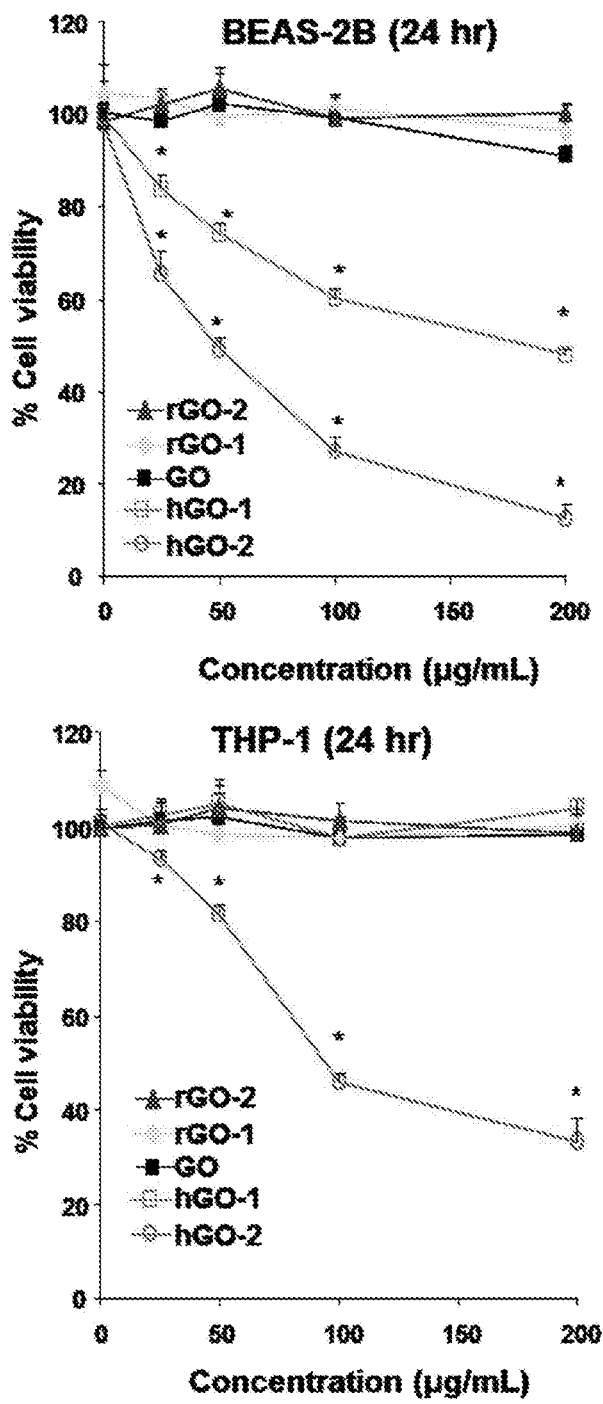
FIG. 26 shows THP-1 and BEAS-2B viability assessed by the MTS assay after 24 h. THP-1 or BEAS-2B cells were exposed to 0-200 µg/mL GO suspensions for 24 h. An MTS was performed as described in FIG. 21A.

Because lipid peroxidation can trigger cell death, we evaluated the cytotoxic potential GO nanosheets in THP-1 and BEAS-2B cells. After 48 h exposure most GO samples show significant cytotoxicity in THP-1 and BEAS-2B cells in the ranking order: hGO-2>hGO-1>GO>rGO-1>rGO-2 (FIG. 21A). Interestingly BEAS-2B cells were more sensitive to the cytotoxic effects of hGO than THP-1 cells. These effects are time-dependent, as demonstrated by the fact that only hGO-2 shows toxicity in THP-1 cells after 24 h of exposure (FIG. 26). The cytotoxicity ranking of the various types of GO correlates well with the carbon radical density, yielding correlation coefficients of 0.95 in BEAS-2B cells and 0.98 in THP-1 cells (FIG. 21B). These data confirm the importance of carbon radicals on the GO in promoting toxicity in mammalian cells. Heat maps were used to integrate the data sets for lipid peroxidation, membrane leakage and cell death, using a one-way ANOVA statistical method (FIG. 21D). Visual data display, where red indicates significant toxicity and green represents absence of toxicity, demonstrates excellent correlation among the cellular response parameters, confirming a hazard ranking of hGO-2>hGO-1>GO>rGO-1>rGO-2. While hGO-2 induces significantly higher toxicity than pristine GO, rGO-2 had the least hazardous potential.

Induction of Acute Lung Inflammation by GO Nanosheets

Figure 22A:
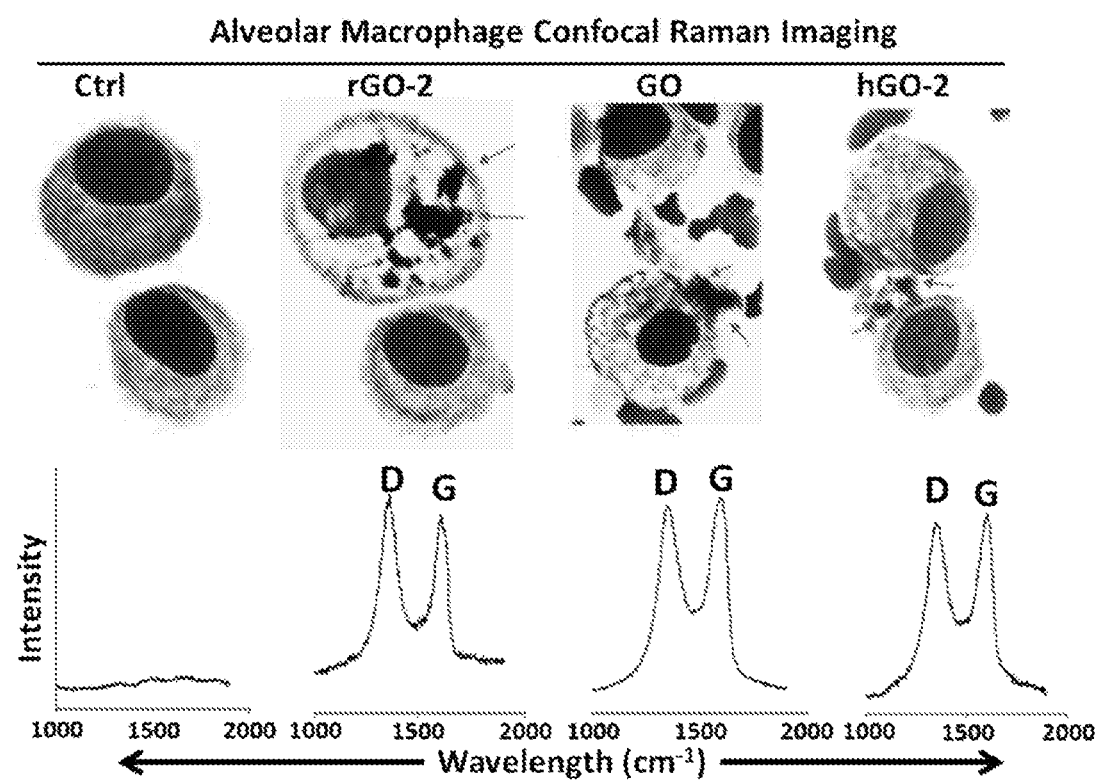
FIGS. 22A-22D show lipid peroxidation and cell death of primary macrophages in the BALF after GO exposure by oropharyngeal aspiration.
Figure 22B:
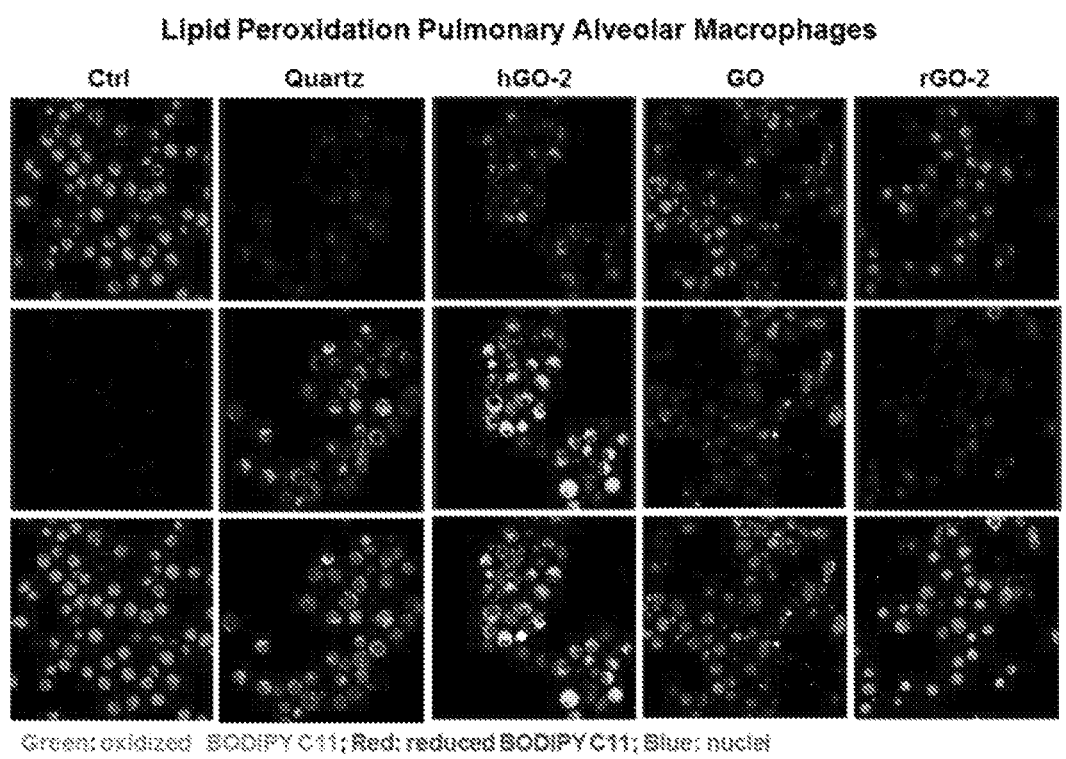
Figure 22C:
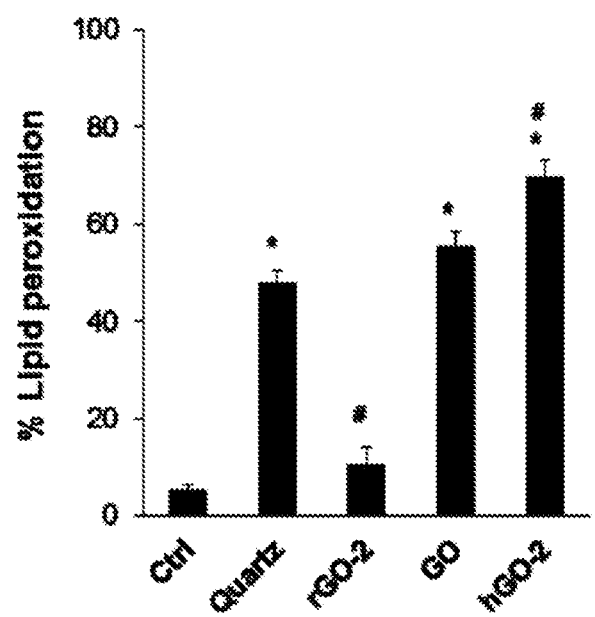
Figure 22D:
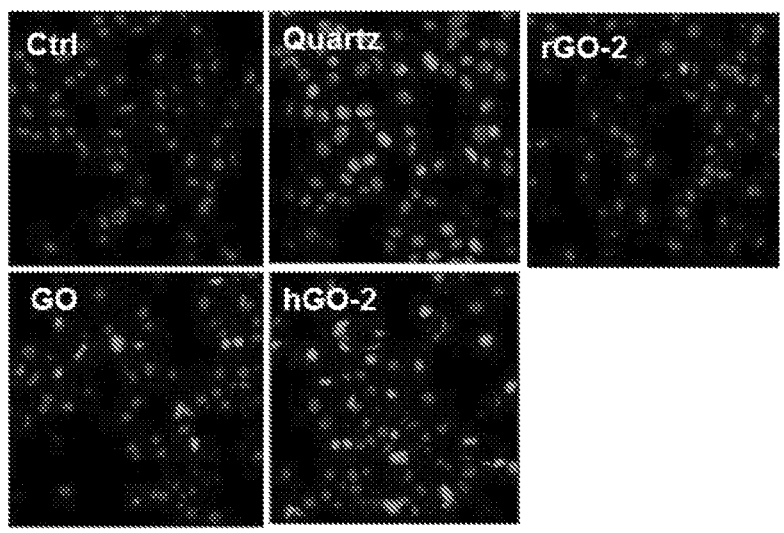
Figure 22D:
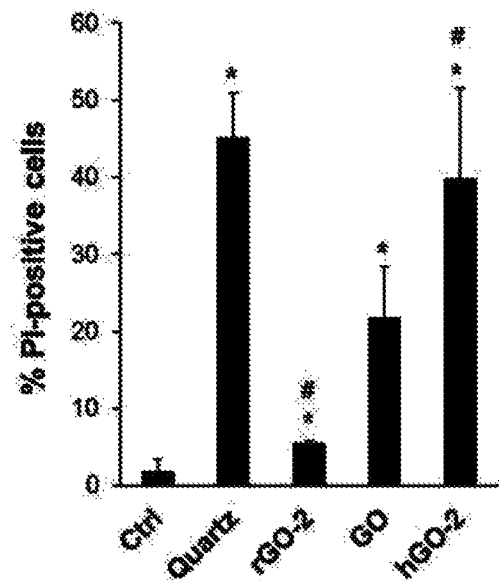

To see if the in vitro hazard profiling is predictive of in vivo toxicological outcome, we used an oropharyngeal aspiration approach, according to which mice were exposed to 2 mg/kg hGO-2, GO, and rGO-2. This dose was selected based on prior dose-response studies, where a dose of 2 mg/kg for graphene and GO falls on the linear part of the dose response curve (Wang et al. (2015) *ACS Nano*, 9: 3032-3043). Following exposure for 40 h, animals were sacrificed and bronchoalveolar lavage fluid (BALF) obtained to examine the effects of go on cells and cytokines. Raman microscopy was used to assess GO uptake in pulmonary macrophages (FIG. 22A). Characteristics D and G bands were obtained for all GO materials, demonstrating that GO and hGO-2 are largely associated with the cell membrane, while rGO-2 was taken up into the cell. These results are with the cellular TEM and confocal data (FIG. 19). We also demonstrated the presence of lipid peroxidation in alveolar macrophages, by using IMAGE-IT® lipid peroxidation kit for confocal viewing (FIG. 22B). This demonstrated that the % of cells undergoing lipid peroxidation (green fluorescence) amounted to 69% and 55% in animals exposed to GO and hGO-2, respectively (FIG. 22C). Quartz was used as a positive control and resulted in lipid peroxidation in 50% of the cells. In contrast, the percent lipid peroxidation was 11% in the BALF cells of rGO-2 exposed animals. We also assessed permeability of the BALF cells, using propidium iodide (PI) staining (Cevik et al. (2003) *Cell Death and Differentiation*, 10: 928-929). As demonstrated in FIG. 22D, BAL cells from hGO-2 exposed animals showed ~40% PI-positive cells, 22% for GO and 5% for rGO-2. These data show that the impact of the GO-materials on pulmonary alveolar macrophages duplicate the results seen in tissue culture cells.

Figure 23A:
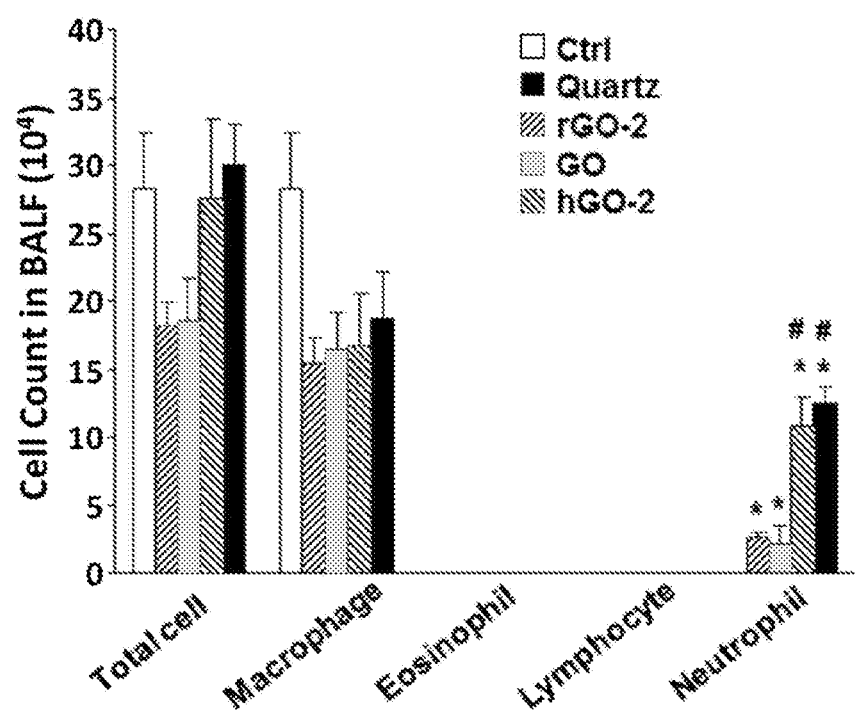
FIGS. 23A-23C show induction of acute lung inflammation induced by the various GO materials.
Figure 23B:
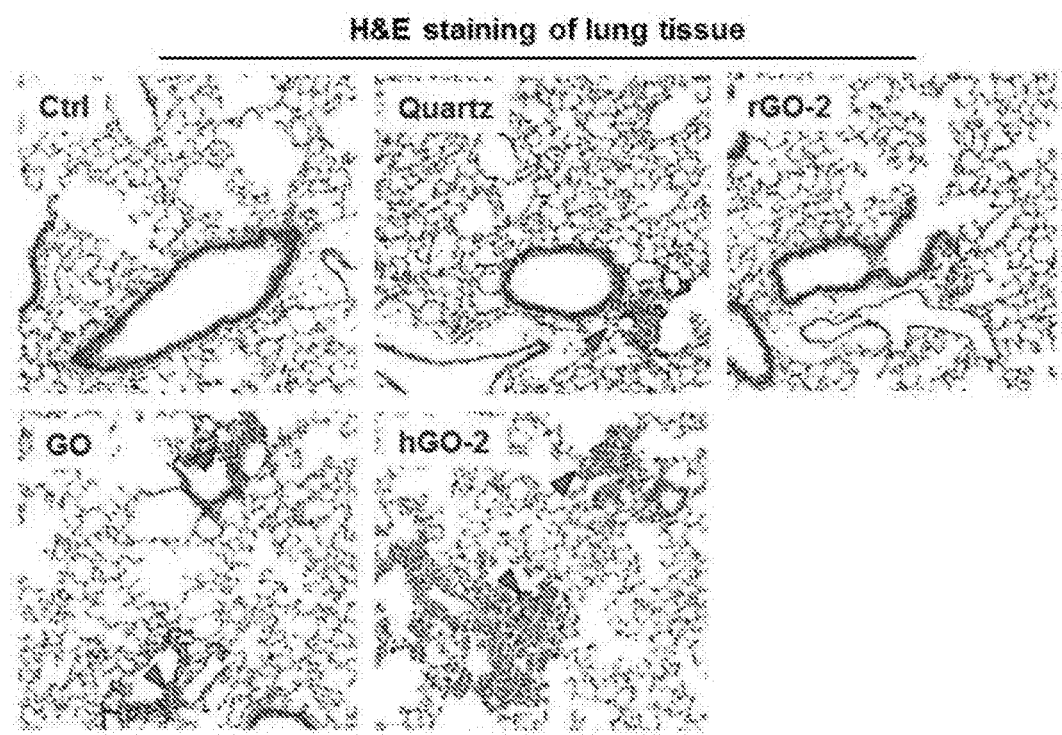
Figure 23C:
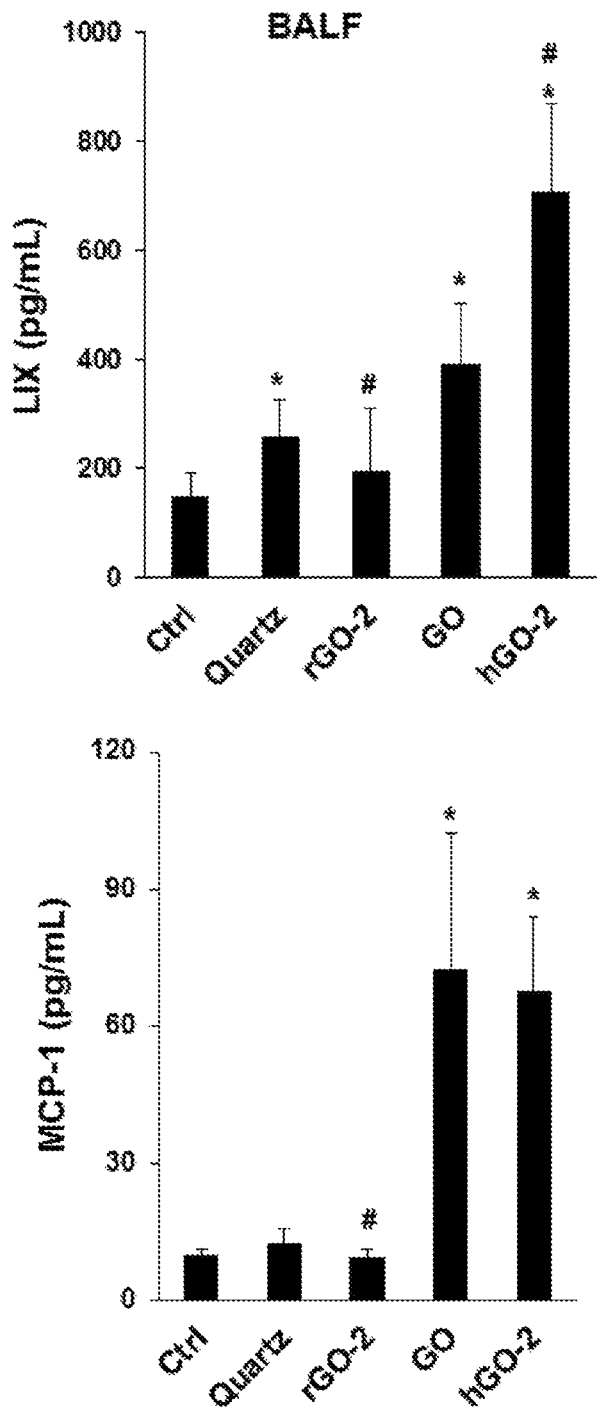
Figure 27A:
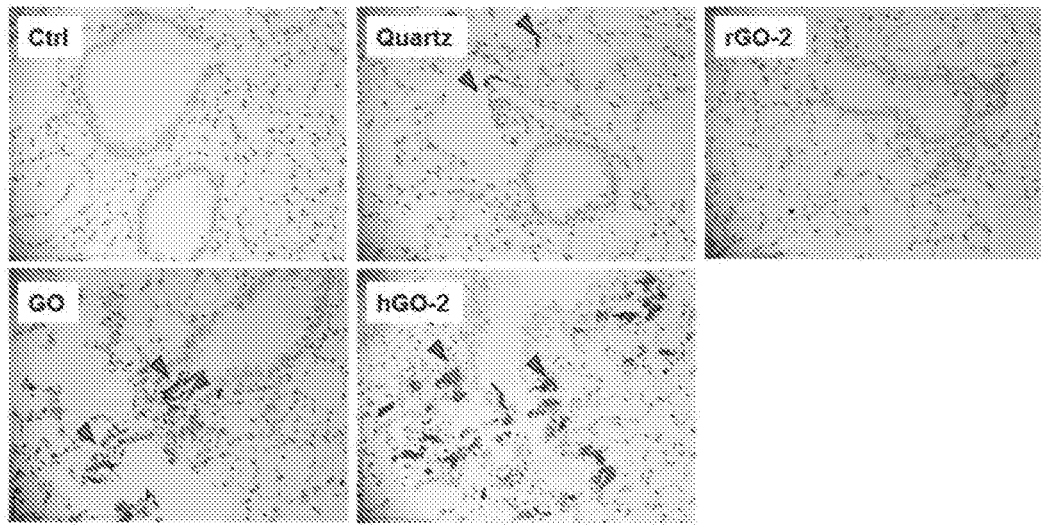
FIGS. 27A and 27B illustrate immunocytochemistry (ICC) staining to determine the presence of apoptotic cells in the lung.
Figure 27B:
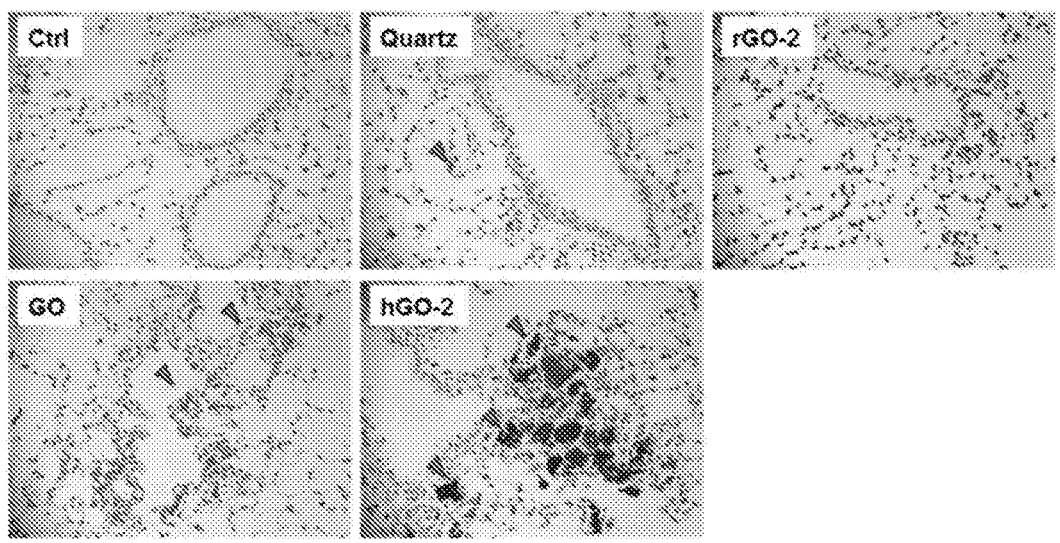
Figure 28:
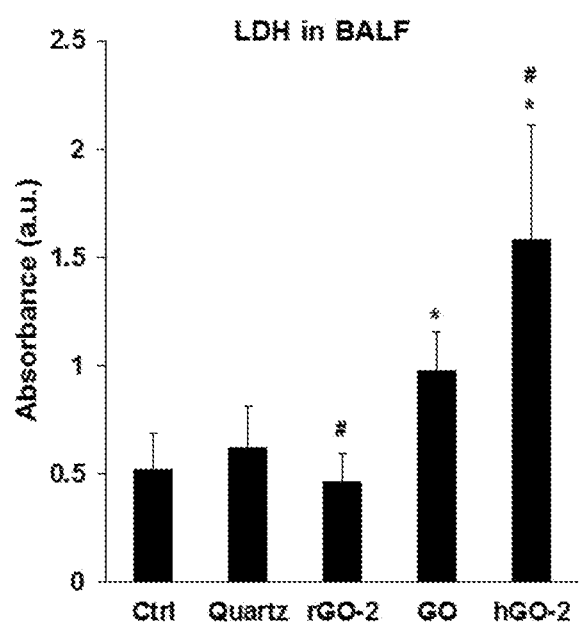
FIG. 28 illustrates detection of LDH in BALF. The LDH release in BALF of animals exposed to 2 mg/kg rGO-2, GO and hGO-2 was measured by a CYTOTOX 96® Non-Radioactive Cytotoxicity Assay kit from Promega.

We also assessed pro-inflammatory effects in the lung. Quartz and hGO-2 induced significantly higher levels of neutrophil recruitment to the BALF, compared to exposure to pristine GO and rGO-2 (FIG. 23A). The pro-inflammatory response in the BALF was also reflected in the intensity of focal pulmonary infiltrates, as demonstrated by hematoxylin and eosin (H&E) staining (FIG. 23B). Moreover, GO and hGO also induced significantly higher levels of the pro-inflammatory cytokines, LIX and MCP-1, in the BALF (FIG. 23C). Assessment of lung cell death by TUNEL staining or immunohistochemistry analysis of the expression of activated caspase-3, showed significantly more cytotoxicity in the lungs of animals exposed to GO and hGO compared to rGO (FIGS. 27A and 27B), Pulmonary cytotoxicity was further confirmed by assessment of lactate dehydrogenase (LDH) release in the BALF, which confirmed higher levels in GO and hGO exposed animals than mice aspirating rGO (FIG. 28).

Discussion

In this study, we used a GO library with different GO surface functionalities to determine the hazard potential in pulmonary cell types and the lung. We demonstrated that pristine GO and hydrated GO samples, which express the highest .C densities, exhibit the highest pro-oxidative effects in vitro and in vivo, as evidenced by the tracking of lipid peroxidation, membrane leakage and cell death, compared to reduced GO. The in vitro results were confirmed in mice exposed to GO by oropharyngeal aspiration. GO and hGO-2 induce significantly higher BALF cell counts, production of pro-inflammatory cytokines (including MCP-1 and LIX), lipid peroxidation in macrophage membranes and death of the cells than rGO. Moreover, these pro-inflammatory effects were also duplicated in the appearance of pulmonary infiltrates in the lung and in situ staining for cytotoxicity. Collectively, these data demonstrate that the in vitro and in vivo hazard potential of GO is determined, in part, by low surface functionalization, in particular, the density of .C on the material surfaces. This information is considerable importance in understanding the hazard potential of GO in mammalian tissues, and provide structure-activity relationships that can be used for safer designed materials.

The most significant finding in this communication is that the level of oxidative modification of the GO surface as well as the presence of carbon radicals determine the in vitro and in vivo hazard potential, as reflected by lipid peroxidation of the surface membrane, membrane damage, subcellular processing, cytotoxicity, and the generation of acute pro-inflammatory effects in small airways of the lung. This indicates that the structure-activity relationships related to the oxidation status and expression of surface OH, COOH, COC groups and carbon radicals, needs to be included with physicochemical properties such as edge size and colloidal behavior, which depends on the relative degree of hydrophobicity of the planar surface and charged edges (Hu et al. (2010) *ACS Nano*, 4: 4317-4323; Zhao et al. (2015) *Env. Sci.: Nano.* 2: 136-142). Collectively, these properties determine the hazard potential of GO, which can dynamically differ from material to material (Zhang et al. (2016) *Adv. Drug Deliv. Rev.* 105: 145-162; Sydlik et al. (2015) *ACS Nano*, 9: 3866-3874). This complexity may also explain the apparent discrepancies in the data on GO toxicity, which could vary as a result of the experimental approach and different exposure routes (Zhang et al. (2016) *Adv. Drug Deliv. Rev.* 105: 145-162; Wang et al. (2015) *ACS Nano*, 9: 3032-3043; Sydlik et al. (2015) *ACS Nano*, 9: 3866-3874). While some in vitro and in vivo studies clearly show that GO pose no particular risks and can be of beneficial biological use (Nishida et al. (2016) *Int. J. Nanomed.* 11: 2265-2277; Vera-Sanchez et al. (2016) *Stem Cells and Dev.* 25: 1742-1754; Garcia-Alegria et al. (2016) *Sci. Rep.*, 6: 25917; Jasim et al. (2016) *ACS Nano*, 10: 10753-10767), others have indicated that GO nanosheets can be hazardous (Wang et al. (2015) *ACS Nano*, 9: 3032-3043). Recently, Jasim et al. found that GO exhibited negligible liver and renal toxicity following intravenous injection of GO in mice, at doses up to 10 mg/kg (Jasim et al. (2016) *ACS Nano*, 10: 10753-10767). However, this stands in contrast to studies showing that intravenously injected GO could induce significant inflammation and fibrosis in the liver or kidney (Sasidharan et al. (2015) *Carbon*, 95: 511-524; Roberts et al. (2016) *Part. Fibre Toxicol.* 13(1): 34; Wen et al. (2015) *J. Appl. Toxicol.* 35: 1211-1218). It has also been shown that GO could provoke fibrogenic effects in the lungs following oropharyngeal aspiration (Wang et al. (2015) *ACS Nano*, 9: 3032-3043; Duch et al. 92011) *Nano Letts.* 11: 5201-5207). Moreover, the pulmonary effects are dependent on the GO surface functionalities and can be reduced by Pluronic coating (Wang et al. (2015) *ACS Nano*, 9: 3032-3043). Sydlik et al. have also suggested that the oxidation level of GO may determine its toxicity (Sydlik et al. (2015) *ACS Nano*, 9: 3866-3874). However, due to the complexity of the surface functional groups, including the presence of .C, it is unclear what the role of each functionality is in terms of potential hazardous impact (Li et al. (2016) *ACS Nano*, 10:

10966-10980). Through the establishment of a well-characterized GO library that systematically varied the level of surface expression, we demonstrate that the most proximate indicator of pulmonary toxicity is correlated to the surface .C densities. Hydration enhances density and expression of these radicals by opening the epoxy groups on GO surface (Id.). Reduction has the opposite effect. The carbon radicals are embedded in the π-network plane, allowing single unconjugated electrons to associate with the electronic structure of the neighboring double bonds, and ability to travel through the linked C=C network.[4] Thus, the entire GO nanosheet could function as "super porphyrin" structure with embedded carbon radicals (Samuel et al. (2016) *Proc. Natl. Acad. Sci. USA,* 112: 2343-2348). With the ability of .C to donate electrons resulting in the formation of the superoxide radical, it is possible that unsaturated lipids in contact with the GO basal plane can be oxidized, leading to the formation of lipoperoxides (Li et al. (2016) *ACS Nano,* 10: 10966-10980).

Another interesting aspect of our study relates to the different sites of cellular localization of pristine, hydrated and reduced GO. While most GO and hGO nanosheets associated with the surface membrane in THP-1 and BEAS-2B cells, rGO was principally taken up into the cell. These results are in agreement with the data of Mari et al., who demonstrated that while large amounts of GO could be seen to be located principally in the plasma membrane, graphene was taken up into the cytoplasm of a neuroblastoid cellline, SK—N—BE(2) (Mari et al. (2016) *Int. J. Mol. Sci.* 17(12): 1995). The differences we observed may depend on differences in the amphiphilic properties of the materials. Thus, while GO and hGO exhibit hydrophilic edges and hydrophobic planar surfaces that may affect membrane association, the hydrophobicity of the rGO nanosheets may be involved in increased propensity for cellular uptake. The issue is complicated, however, because some reports show that pristine GO could be internalized into the cytoplasm (Mu et al. (2012) *ACS Appl. Mater. Interfaces,* 4: 2259-2266; Huang et al. 92012) Small, 8: 2577-2584; Zhang et al. (2013) *ACS Appl. Mater. Interfaces,* 5: 1761-1767). Could this be due to differences between cell types (e.g, phagocytic versus non-phagocytic cells or different stages of cell differentiation) or is the cellular association principally determined by physicochemical properties? Mu et al. reported a size-dependent contribution to cellular uptake of GO nanosheets that exhibit a protein corona (Mu et al. (2012) *ACS Appl. Mater. Interfaces,* 4: 2259-2266). Their study suggested that small GO sheets are taken up principally by clathrin-mediated endocytosis while larger sheets are internalized by a process of phagocytosis (Id.). This stands in contrast with the work of Ma et al., who showed that the majority of BSA-FITC-labeled GO nanosheets of the larger size were associated with the cell membrane while small GO sheets were internalized by the macrophage cell line, J774A.1 (Ma et al. (2015) *ACS Nano,* 9: 10498-10515). These are not the only parameters, however, that determine cellular uptake, and one also have to consider the impact of GO surface charge and functionalization, similar to what we show (Lammel et al. (2013) *Part Fibre Toxicol.,* 10: 27). This complexity can only be addressed by considering a further extension of the combinatorial library concept, where in addition to control over the surface functionality, one would also introduce additional parameters and other cell types to reach a final conclusion.

Our study focused on the pulmonary toxicity because some GOs is prepared in powder form and used in applications such as coatings, conductive inks or paints, additives in polymeric composites or absorbents, which can readily can be aerosolized and inhaled (Zhu et al. (2010) *Adv. Mat.* 22: 3906-3924; Georgakilas et al. (2012) *Chem. Rev.* 112: 6156-6214). However, GO has been explored for use in medical devices, tissue engineering, and drug delivery, which introduces new exposure scenarios and potential risks (Sydlik et al. (2015) *ACS Nano,* 9: 3866-3874). Langer et al have shown that GO is moderately biocompatible at the subcutaneous and intraperitoneal injection sites, where an inflammatory reaction may develop that is consistent with a typical foreign body reaction (Id.). Chemical reduction of GO resulted in accelerated immune cell infiltration, uptake, and clearance at these injection sites (Id.). In another study, it was demonstrated that GO-coated substrates could significantly enhance the differentiation of mouse embryonic stem (ES) cells to both primitive and differentiated hematopoietic cells (Garcia-Alegria et al. (2016) *Sci. Rep.* 6: 25917). All considered, the collective body of work would seem to suggest that differences in GO usage could change the exposure scenarios and types of tissues and organs that could be impacted. The responses in the lung are not necessarily indicative of effects elsewhere. Our study demonstrates the importance of considering all the variables at play in contemplating the use of GO for biological experimentation or assessment of its potential adverse health effects for different exposure scenarios.

Conclusions

In this study, we prepared a library of GO nanomaterials with different levels of surface functionalities to explore the potential to induce acute lung inflammation. Carbon radicals were found to be the dominant surface functionality that induces cytotoxicity in THP-1 and BEAS-2B cells. This toxicity pathway involves plasma membrane adsorption, lipid peroxidation, membrane damage, and cell death. These in vitro toxicological pathways are also responsible for acute inflammation in the murine lung following local exposure. hGO-2, representative of a material with high carbon radical density, induced significantly more lipid peroxidation and membrane damage in tissue culture cells than rGO. These results also accurately predict similar effects in primary alveolar macrophages, along with inducing acute pro-inflammatory responses in the lung. Pristine GO showed moderate effects, while rGO-2 induced low levels of lung inflammation. The study provides valuable information on how to structure the toxicological profiling of GO nanosheets exhibiting different levels of surface functionality.

Materials and Methods

Chemicals.

The BETA-GLO® Assay System, CYTOTOX 96® Non-Radioactive Cytotoxicity Assay, GSH-GLO™ Glutathione Assay, CELLTITER-GLO® Luminescent Cell Viability Assay (ATP) and CellTiter 96® AQueous One Solution Cell Proliferation Assay (MTS) were purchased from Promega (Madison, Wis., USA); graphite flakes were provided by Asbury Graphite Mills; Hoechst 33342, FITC labeled Bovine Serum Albumin (BSA), Alexa Fluor 594-conjugated wheat germ agglutinin (WGA), Propidium iodide and IMAGE-IT® Lipid Peroxidation Kit were purchased from Life Technologies (Grand Island, N.Y., USA). Min-U-Sil was obtained from U.S. Silica (Frederick, Md., USA). Bronchial epithelial growth medium (BEGM) was obtained from Lonza (Mapleton, Ill., USA): this medium is supplemented with a number of growth factors, including bovine pituitary extract (BPE), insulin, hydrocortisone, hEGF, epinephrine, triiodothyronine, transferrin, gentamicin/amphotericin-B and retinoic acid. Roswell Park Memorial Institute medium 1640 (RPMI 1640) was purchased from Invitrogen (Carlsbad, Calif., USA). Low-endotoxin bovine serum albumin (BSA) and fetal bovine serum (FBS) were purchased from Gemini Bio-Products (West Sacramento, Calif., USA).

Acquisition and Synthesis of a Surface Functionalized GO Library.

The GO library was established using methods reported previously.[4] Pristine GO was prepared by a modified Hummers' method. To prepare reduced GO, pristine GO was dispersed in NMP by ultrasonication for 1 h at 50% power (~55 W). The solution was heated to 150° C. with constant stirring in a silicone oil bath for 1 hour (rGO-1) or 5 h (rGO-2). For the preparation of hydrated GO, 10 mL pristine GO suspension (5 mg/mL) was diluted with 90 mL deionized (DI) water and mixed with 80 mg NaOH (0.02 M), using dispersal by a sonication probe (Sonics & Materials, USA) at 32 W for 10 s. The GO mixture was transferred into a round flask and refluxed at 50 or 100° C. in an oil bath with constant magnetic stirring for 24 h. 1 M HCl solutions were used to neutralize the reaction. The mixture was centrifuged at 50,000 rpm for 30 min to collect the hydrated GO pellets. After washing with DI water three times, the hydrated GO samples were dispersed in DI water and stored at 4° C.

Physicochemical Characterization of GO Samples.

To obtain AFM images, Si wafers were pretreated by 2.5 mM (3-aminopropyl) triethoxysilane (APTES) aqueous solution for 30 min to functionalize the surface with a monolayer. The wafers were rinsed twice with DI water and dried under $N_2$. A drop of 10 μg/mL GO solution was placed on the wafer, followed by washing twice with DI water (~5 s) and drying under $N_2$. The GO sample then underwent heat treatment for 30 min at 250° C. AFM images were obtained by an Asylum Research Cypher ES AFM. Images were taken at random locations on the sample and showed little variation. All images were obtained with the same tip and scanning conditions.

X-ray photoelectron spectroscopy (XPS, AXIS Ultra DLD, Kratos, UK) has been used to investigate the chemical state and calculate the atomic concentration of oxidized groups on the GO surface with monochromatic Al Kα at 15 kV and 10 mA. For sample preparation, suspensions of GO samples were dropped on the silicon substrate and dried at room temperature. The data analysis and curve fitting were performed with the CasaXPS program (Casa Software Ltd., UK).

TEM images of GO samples were obtained by dropping GO suspensions (25 g/mL) on Cu grids. After drying at room temperature, the images were taken on a JEOL 1200 EX TEM with accelerating voltage 80 kV.

The molecular structure of all GO samples was characterized using Raman spectroscopy (Renishaw inVia Reflex, Wotton under Edge, UK) with a 785 nm near-infrared diode and a 50× objective lens. Spectra were obtained using 10 seconds exposure to obtain two scans 1000-2000 $cm^{-1}$ in the wave number region.

The EPR measurements were obtained with an X-band Bruker ELEXYS 580 spectrometer. 5 mg GO nanosheets were dried under vacuum, and allowed to settle on the bottom of 2 mm ID quartz EPR tubes prior to data collection. The field was calibrated using a standard sample with a known g-factor (2,2-diphenyl-1-picrylhydrazyl, DPPH). The EPR spectra were detected at room temperature with frequency at 9.785845 GHz, center field at 3480 G, attenuator at 13.0 dB and g value at 2.0029.

Zeta-potential and hydrodynamic size measurements of the GO suspensions were performed using a ZetaSizer Nano-ZS instrument (Malvern Instruments, Worcestershire WR, UK).

Assessing the Pro-Oxidative Potential of GO, Using a GSH Assay.

Assessment of the GSH content was obtained by using a GSH-Glo™ Glutathione Assay. This is a luminescence-based assay for detecting and quantifying glutathione (GSH). The assay is based on the conversion of a luciferin derivative to luciferin by glutathione S-transferase (GST). The signal generated in a coupled reaction with firefly luciferase is proportional to the amount of glutathione present in the sample. The assay was performed under abiotic conditions by adding 10 μL aliquots of $Co_3O_4$ or GO at 5 mg/mL to a 96-well plate together with 90 μL GSH-Glo agent for 30 min. The luciferin detection agent was added to each well (100 μL/well) and the luminescence was detected by on a SpectraMax M5 microplate spectrophotometer (Molecular Devices, Sunnyvale, Calif.).

Assessment of Cellular Viability by a MTS Assay.

BEAS-2B and THP-1 cells were obtained from ATCC (Manassas, Va.), and cultured were cultured in BEGM or complete RPMI 1640 (supplemented with 10% fetal bovine serum), respectively, at 5% $CO_2$ and 37° C. Before exposure to GO samples, BEAS-2B cells were seeded at a density of $1\times10^4$/well in 96-well plates (Corning, N.Y., USA) overnight at 37° C. All the GO solutions were freshly prepared in BEGM containing 0.2% BSA or in complete RPMI 1640. These suspensions were dispersed by sonication (Sonics & Materials, USA) at 32 W for 10 s at the desired final concentration, before addition to the cells. Aliquots of $3\times10^4$ THP-1 cells were seeded overnight in 0.1 mL complete RPMI medium into 96-well plates (Corning, N.Y., USA), receiving 1 μg/mL phorbol 12-myristate acetate (PMA), while BEAS-2B cells were suspended in BEGM media at a density at $1\times10^4$ cells per well. After exposure to 0-200 μg/mL of each of the GO suspensions for 24 or 48 h, the cell culture medium was removed, followed by the addition of 120 μL culture medium containing 10% MTS stock solution for 1-2 hour at 37° C. in a humidified 5% $CO_2$ incubator (Li et al. (2014) ACS Nano, 8: 1771-1783). The supernatants were transferred to a new 96-multiwell plate and centrifuged at 2000 g for 10 min in NI Eppendorf 5430 to spin down the cell debris and nanoparticles. 100 μL of the supernatant was removed from each well and transferred into a new 96-well plate. The absorbance of formed formazan was read at 490 nm on a SpectraMax M5 microplate spectrophotometer.

Confocal Imaging of BSA-FITC Labeled GO Samples in Cells.

BSA-FITC labeled GO samples were prepared by a diimide-activated amidation reaction as described before. Briefly, 5 mg EDC and 10 mg NHS were dissolved in 2 mL rGO-2, GO or hGO-2 suspensions (100 μg/mL) in water and the mixtures stirred for 2 hr at room temperature. The GO pellets were collected by centrifugation at 20,000 rpm for 10 min, and reacted with 1 mL of a suspension containing 0.1 mg/mL of the BSA-FITC solution while stirring for 2 h. The FITC labeled GO samples were collected by centrifugation at 20,000 rpm for 10 min, suspended in 400 μL DI water and stored at 4° C. for further use. For confocal imaging, 300 μL aliquots of THP-1 and BEAS-2B cell suspensions, at densities at $3\times10^5$/mL and $1\times10^5$/mL, respectively, were seeded into 8 well chambers (NUNC® LAB-TEK® II chambered coverglass, Sigma-Aldrich) for overnight incubation. The cells were exposed to 25 μg/mL of the various GO suspensions for 16 h, followed by 3 washes in PBS. Cell membranes and nuclei were stained with Alexa Fluor 594-conjugated WGA and Hoechst 33342, respectively, at room temperature for 1 h. The cells were visualized under a confocal microscope (Leica Confocal SP2 1P/FCS). High magnification images were obtained under the 63× objective.

Assessment of Cell Membrane Lipid Peroxidation.

THP-1 cells were treated with 100 µg/mL of each of the GO samples for 16 h or 10 µM cumene hydroperoxide (positive control) for 1 h. Aveolar macrophages were obtained from the BALF of mice exposed to 5 mg/kg quartz or 2 mg/kg rGO-2, GO or hGO-2 for 40 h, and allowed to adhere to the bottom of 8-well chambers. After washing, the cells were incubated with 10 µM Image-iT® Lipid Peroxidation Sensor and Hoechst 33342 in culture media for 30 min (Li et al. (2016) ACS Nano, 10: 10966-10980). The stained cells were washed three times in PBS, and used for confocal microscopy under a TCSSP2 confocal laser scanning microscope (Leica, Wetzlar, Germany) for visualization of the reduced and oxidized fluorescent dye at excitation/emission wavelengths of 581/591 nm (Texas Red® filter set) and 488/510 nm (traditional FITC filter), respectively. We also performed flow cytometry analysis on a FACS Vantage SE flow cytometer from BD (Franklin Lakes, N.J.), using FlowJo® Software (Ashland, Oreg.) to calculate the ratio of the emission fluorescence intensities at 590 nm to 510 nm.

RBC Hemolysis Assay.

Heparinized mouse blood was washed with saline, following which the RBCs were diluted to $1 \times 10^8$ cell/mL in PBS. 490 µL of the diluted RBC suspension was mixed with 10 µL of GO nanoparticles to achieve final concentrations of 0-200 µg/ml. The addition of saline was used as a negative control while 0.25% Triton X-100, served as positive control. The mixtures were gently stirred and incubated for 3 h at 37° C. The samples were centrifuged and the absorbance of the supernatants measured at 541 nm in a SpectraMax M5 microplate spectrophotometer. The percent hemolysis in each sample was calculated as previously described (Li et al. (2014) ACS Nano, 8: 1771-1783).

Use of TEM to Detect of Cellular Uptake of GO.

After exposure to 100 µg/mL rGO-2, GO or hGO-2 for 16 h, the cells were washed and fixed with 2% glutaraldehyde in PBS. Following post-fixation in 1% osmium tetroxide in PBS for 1 h, the cells were dehydrated in a graded series of ethanol, and then treated with propylene oxide before embedding in Epon. Approximately 50-70 nm thick sections were cut on a Reichert-Jung Ultracut E ultramicrotome and picked up on Formvar-coated copper grids. The sections were stained with uranyl acetate and Reynolds lead citrate and examined on a JEOL transmission electron microscope at 80 kV in the UCLA BRI Electron Microscopy Core, as previously reported.

Animal Treatment and Assessment of Exposure Outcomes.

Eight-week-old male C57Bl/6 mice purchased from Charles River Laboratories (Hollister, Calif.) were used for exposure studies. All animals were housed under standard laboratory conditions according to UCLA guidelines for care and treatment of laboratory animals as well as conforming to the NIH Guide for the Care and Use of Laboratory Animals in Research (DHEW78-23). These conditions are approved by the Chancellor's Animal Research Committee at UCLA and include standard operating procedures for animal housing (filter-topped cages; room temperature at 23±2° C.; 60% relative humidity; 12 h light, 12 h dark cycle) and hygiene status (autoclaved food and acidified water). Animal exposure to GO materials was carried out by an oropharyngeal aspiration method as described by us. Animals were anesthetized by intraperitoneal injection of ketamine (100 mg/kg)/xylazine (10 mg/kg) in a volume of 100 µL. What the animals being held in a vertical position, 50 µL aliquots, containing 2 mg/kg of each of the GO suspensions in PBS, were instilled at the back of the tongue for pulmonary aspiration. Control animals received the same volume of PBS. The positive control group in each experiment received 5 mg/kg quartz particles (Min-U-Sil). The mice were sacrificed after 40 h exposure. BALF and lung tissue were collected as previously described. The BALF was used for performance of total and differential cell counts and measurement of LIX and MCP-1 levels. Lung tissue was stained with hematoxylin/eosin, or used for TUNEL staining or used for immunohistochemistry (ICC) analysis of activated caspase 3.

Confocal Raman Microscopy.

Raman analysis was performed using backscattering geometry in a confocal configuration at room temperature in a Renishaw inVia Raman microscope system, equipped with a 514.5 nm Ar laser. Laser power and beam size were approximately 2.5 mW and 1 m, respectively, while the integration time was adjusted to 15 s. Primary alveolar macrophages obtained from the BALF of sacrificed animals, were suspended in c-RPMI 1640 medium and seeded onto sterile glass cover slips. After 2 h incubation, cells were washed, fixed in 4% paraformaldehyde and examined under the Raman microscope.

Statistical Analysis.

Mean and standard deviation (SD) were calculated for each parameter. Results were expressed as mean±SD of multiple determinations. Comparisons between groups were evaluated by two-side Student's t-test or one-way ANOVA. A statistically significant difference was assumed with p was <0.05.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A hydrated graphene oxide (hGO) film disposed on a glass, metal, or polymer solid surface, where said hydrated graphene oxide film has increased carbon radical (.C) density as compared to pristine graphene oxide (GO), wherein said increased carbon radical density is characterized by:
   i) an EPR spectrum showing a single symmetric resonance peak of π-conjugated carbon radical;
   ii) an atomic percent concentration of epoxide (C—O—C) groups lower than pristine graphene oxide; and
   iii) an atomic percent concentration of C—OH groups for said hGO at least twice the atomic percent concentration of C—OH groups on pristine graphene oxide as determined by X-ray photoelectron spectroscopy (XPS);
   wherein said hydrated graphene oxide film disposed on said surface has increased antimicrobial activity as compared to a pristine graphene oxide film.

2. The graphene oxide of claim 1, wherein the antimicrobial activity of said hydrated graphene oxide film is proportional to the carbon radical density.

3. The graphene oxide of claim 1, wherein said hydrated graphene oxide film shows increased lipid membrane binding and/or induction of lipid peroxidation as compared to pristine graphene oxide.

4. The hydrated graphene oxide film of claim 1, wherein:
said graphene oxide shows a carbon radical content as determined by electron paramagnetic resonance (EPR) with an absorbance peak area greater than about $15 \times 10^6$; and/or
said graphene oxide has an atomic % concentration of oxidized groups (C—OH) on the graphene oxide surface of about 9.9 or greater as determined by XPS.

5. The hydrated graphene oxide film of claim 1, wherein:
said hydrated graphene oxide film is effective to kill gram negative bacteria; and/or
said hydrated graphene oxide film is effective to kill gram positive bacteria; and/or
said hydrated graphene oxide film is effective to kill *E. coli*.

6. The hydrated graphene oxide film of claim 1, wherein:
said hydrated graphene oxide film is adsorbed to said solid surface; and/or
said hydrated graphene oxide film is spin-coated on said solid surface; and/or
said hydrated graphene oxide film is covalently attached to said solid surface.

7. The hydrated graphene oxide film of claim 6, wherein said hydrated graphene oxide film ranges in thickness from about 1 nm up to about 50 nm.

8. The graphene oxide of claim 6, wherein:
said hydrated graphene oxide film is attached to a surface that comprises a surface of a catheter; and/or
said hydrated graphene oxide film is attached to a surface of biological implant; and/or
said hydrated graphene oxide film is attached to a surface that comprises a surface of a biological implant selected from the group consisting of a dental implant, an encapsulated implantable drug delivery system, an implanted canula, and an orthopedic implant; and/or
said hydrated graphene oxide film is attached to a surface of an orthopedic implant; and/or
said hydrated graphene oxide film is attached to a surface of an orthopedic implant selected from the group consisting of an artificial joint, a bone screw, and a bone nail; and/or
said hydrated graphene oxide film is attached to a surface of an implant selected from the group consisting of an Austin-Moore prosthesis, Baksi's prosthesis, Charnley prosthesis, Condylar blade plate, Ender's nail, Grosse-Kempf (GK) nail, Harrington rod, Hartshill rectangle, Insall Burstein prosthesis, Richard N. W. Wohns interspinous implant, Kirschner wire, Kuntscher nail, Luque rod, Moore's pin, Neer's prosthesis, Rush nail, Smith Peterson (SP) nail, Smith Peterson nail with McLaughlin's plate, Seidel nail, Souter's prosthesis, Steffee plate, Steinmann pin, Swanson prosthesis, Talwalkar nail, and a Thompson prosthesis.

9. The hydrated graphene oxide film of claim 1, wherein:
said hydrated graphene oxide film is a component of a composite or nanocomposite; and/or
said hydrated graphene oxide film is a component of a composite or nanocomposite selected from the group consisting of a metal composite or nanocomposite, metal oxide composite or nanocomposite, a polymer composite or nanocomposite, a quaternary phosphonium salt composite or nanocomposite, and a chelator composite or nanocomposite; and/or
said hydrated graphene oxide film is a component of a composite or nanocomposite that comprises a metal; and/or
said hydrated graphene oxide film is a component of a composite or nanocomposite that comprises a metal composite selected from group consisting of graphene oxide and silver, graphene oxide and copper, graphene oxide and gold, graphene oxide, and lanthanum; and/or
said hydrated graphene oxide film is a component of a composite or nanocomposite that comprises a metal oxide; and/or
said hydrated graphene oxide film is a component of a composite or nanocomposite that comprises a metal oxide selected from the group consisting of $TiO_2$, ZnO, $Fe_3O_4$, and $SnO_2$; and/or
said hydrated graphene oxide film is a component of a composite or nanocomposite that comprises a polymer; and/or
said hydrated graphene oxide film is a component of a composite or nanocomposite that comprises a polymer selected from the group consisting of poly-N-vinyl carbazole (PVK), chitosan, and PVK.

10. The hydrated graphene oxide film of claim 1, wherein said graphene oxide is additionally functionalized with polyethylenimine (PEI) and/or PEG, and/or PVA, and/or polydopamine.

11. The hydrated graphene oxide film of claim 1, wherein said graphene oxide is attached to fibers or to nanofibers.

12. The hydrated graphene oxide film of claim 1, wherein:
said hydrated graphene oxide film is a component of a three-component nanohybrid; and/or
said hydrated graphene oxide film is a component of a three-component nanohybrid that comprises a dimensional GO-Au@Ag nanohybrid; and/or
said hydrated graphene oxide film is a component of a three-component nanohybrid that comprises a GO-poly (acrylic acid)-Ag nanohybrid; and/or
said hydrated graphene oxide film is a component of a three-component nanohybrid that comprises a GO-polydopamine-Ag nanohybrid.

13. The hydrated graphene oxide film of claim 1, wherein:
said hydrated graphene oxide film is a component of a tissue engineering scaffold; and/or
said hydrated graphene oxide film is a component of a tissue engineering scaffold that comprises a protein or carbohydrate scaffold; and/or
said hydrated graphene oxide film is a component of a tissue engineering scaffold that comprises one or more materials selected from the group consisting of collagen, chitosan, hyaluronic acid, fibrin, and gelatin; and/or
said hydrated graphene oxide film is a component of a tissue engineering scaffold that comprises a synthetic scaffold; and/or
said hydrated graphene oxide film is a component of a tissue engineering scaffold that comprises one or more materials selected from the group consisting of glycolic acid derivatives, lactic acid derivatives, and other polyester derivatives; and/or
said hydrated graphene oxide film is a component of a tissue engineering scaffold that comprises a copolymer of 1-lactide and epsilon-caprolactone; and/or
said hydrated graphene oxide film is a component of a tissue engineering scaffold that comprises a polyglycolic acid mesh coated with a copolymer of poly[epsilon-caprolactone-1-lactide].

14. The hydrated graphene oxide film of claim 1, wherein:
said hydrated graphene oxide film is incorporated into a bandage and/or wound dressing; or
said hydrated graphene oxide film is incorporated into a water filter.

15. The hydrated graphene oxide film of claim 1, wherein said hydrated graphene oxide film has a carbon radical content as determined by electron paramagnetic resonance (EPR) with an absorbance peak area about $20 \times 10^6$ or greater.

16. The hydrated graphene oxide film of claim 1, wherein said hydrated graphene oxide film has an atomic percent concentration of oxidized groups (C—OH) greater than about 13.6 as determined by XPS.

17. The hydrated graphene oxide film of claim 6, wherein said hydrated graphene oxide film ranges in thickness from about 5 nm up to about 30 nm.

18. The hydrated graphene oxide film of claim 1, wherein said hydrated graphene oxide film is disposed on a surface of a silicone catheter.

19. The hydrated graphene oxide film of claim 1, wherein said hydrated graphene oxide film consists of hydrated graphene oxide.

* * * * *